US009309497B2

(12) United States Patent
Silva et al.

(10) Patent No.: US 9,309,497 B2
(45) Date of Patent: Apr. 12, 2016

(54) ISOLATED NUCLEIC ACID MOLECULES FROM THE GENOME OF CITRUS SUDDEN DEATH VIRUS AND USES THEREOF

(75) Inventors: Ana Claudia R. Silva, Campinas (BR); Walter Maccheroni, Jr., Campinas (BR)

(73) Assignee: MONSANTO DO BRASIL LTDA., São Paulo (BR)

( * ) Notice: Subject to any disclaimer, the term of this patent is extended or adjusted under 35 U.S.C. 154(b) by 1695 days.

(21) Appl. No.: 10/572,442

(22) PCT Filed: Sep. 20, 2004

(86) PCT No.: PCT/BR2004/000179
§ 371 (c)(1),
(2), (4) Date: Oct. 18, 2006

(87) PCT Pub. No.: WO2005/030943
PCT Pub. Date: Apr. 7, 2005

(65) Prior Publication Data
US 2007/0199102 A1    Aug. 23, 2007

Related U.S. Application Data

(60) Provisional application No. 60/506,520, filed on Sep. 26, 2003, provisional application No. 60/508,979, filed on Oct. 6, 2003, provisional application No. 60/529,246, filed on Dec. 12, 2003, provisional application No. 60/560,466, filed on Apr. 7, 2004.

(51) Int. Cl.
*C12N 15/82*    (2006.01)
*C12N 15/87*    (2006.01)
*A01H 1/00*     (2006.01)
*C12N 7/00*     (2006.01)
*C07K 14/005*   (2006.01)
*C12Q 1/70*     (2006.01)

(52) U.S. Cl.
CPC .............. *C12N 7/00* (2013.01); *C07K 14/005* (2013.01); *C12N 15/8283* (2013.01); *C12Q 1/701* (2013.01); *C12N 2770/40022* (2013.01); *C12N 2770/40051* (2013.01)

(58) Field of Classification Search
CPC ............... C12N 7/00; C12N 15/8283; C12N 2770/4022; C12N 2770/40051; C07K 14/005; C12Q 1/701
See application file for complete search history.

(56) References Cited

PUBLICATIONS

Genbank Accession No. NC_001793, 2000.*
Database EMBL [Online] Sep. 30, 2000, "Grapevine asteroid mosaic-associated virus partial replicase-associated polyprotein, genomic RNA" retrieved from EBI Database accession No. AJ249357.
Database UniProt [Online] Mar. 1, 2001, retrieved from EBI Database accession No. Q9DWU5_9VIRU.
Database UniProt [Online] May 1, 1997, retrieved from EBI Database accession No. P89920_9VIRU.
Michael C. Edwards et al., "Oat Blue Dwarf Marafivirus Resembles the Tymoviruses in Sequence, Genome Organization, and Expression Strategy", Virology 232, 217-227 (1997) Article No. VY978555.
Nina Abou Ghanem-Sabanadzovic et al., "Sequence Analysis of the 3' end of Three *Grapevine Fleck Virus*-like Viruses from Grapevine", Virus Genes 27:1, 11-16, 2003.
M.A. Ayllon et al., "Polymorphism of the 5' terminal region of *Citris tristeza virus* (CTV) RNA: Incidence of three sequence types in isolates of different origin and pathogenicity", Arch Virol. (2001) 146: 27-40.

* cited by examiner

*Primary Examiner* — Li Zheng
(74) *Attorney, Agent, or Firm* — Lowe Hauptman & Ham, LLP

(57) ABSTRACT

The present disclosure relates to nucleic acid molecules comprising the genome of the Citrus Sudden Death Virus (CSDV), the causative agent of Citrus Sudden Death (CSD) disease. The cloned CSDV nucleic acid molecules can be used as probes or can be used to design oligonucleotide primers useful in assays, such as a polymerase chain reaction, for detecting the presence of CSDV in biological samples, particularly leaves, roots and other tissues or organs of plants, such as plants from the genera *Citrus* and *Poncirus*. The disclosure also comprises the nucleic CSDV nucleic acid molecules, in whole or part, as well as transgenic plants, such as monocots and dicots, containing the CSDV nucleic acid molecules, in any kind of combination, so that expression increases resistance to CSD disease.

8 Claims, 19 Drawing Sheets

Figure 1

Comparison of genome sequence of CSDV with the genome sequence of the Oat Blue Dwarf Virus (OBDV)

```
OBDV       ------------------------------------------------------------
CSDV       GTCCCCTGTGATCGTCTCTCCCGCCCTCCAGCCGGAAAGATATTTTTGCTTTAACTTTTC 1                                                          60

OBDV       ------------------------------------------------------------
CSDV       TTTGCACTCTTACGCTCAGATCTACGTGCCTTAGGTCATCTAAGCCGCTATGGATCGCAT 61                                                        120

OBDV       ------------------------------------------------------------
CSDV       CTCTGCCCGCATTCCCGTCGCGCCCGCTTCCGCCGGCCCGACCGAGTACACTCCATACCC 121                                                       180

OBDV       ---------------GTGTCCCA--GTGTCATTAT-TCCGCTCAGTTTCAGATCTGCCG
CSDV       ACACACTCACCCACTCCTACCCCGAGGTGTCTTCACCTCCGGGCCTATTCAACCCTGTCT
                           *  ***   ***** * *  ****  *   ****   *** *
           181                                                       240

OBDV       GAATTCTCCAAG-CATCCCGCCCCAAAAGCCGGCTGCTTAAAATCTGATCTTCTCCATCT
CSDV       CCACTTTCTTCCTCACCATGCCCAAGATGCCCCCATCCGCTGCTACAGACCCCTCACCTT
             * * **      ** *  **** * * ***  *  *         *  *  ***     *
           241                                                       300

OBDV       TGTCAAGTGTC---GTTATGACCACATACGCCTT-CCACCCGCTGCTCCCCACCCCGACC
CSDV       CGCCAACCATCTCCGCTATGACCGT-TCCGCCTCATCGCTCAAGACTCCGCCCGTCAAAC
            *  ***    **      * *******   *  *****     *   *     ****  *    *  *
           301                                                       360

OBDV       TCCTTCGCCACTATCACTGGGGGTGGTTTGAAGGATGTTATCGAAACCCTCTCGTCCACC
CSDV       TCC-----CACTG--ACCGGTGGTACCCTTGCCGATGCCATCCTTTCCTTGGCACCCACC
           ***      ****   **  ** ***    *     ****  ***   ** *    *     *****
           361                                                       420

OBDV       ATCCACAGAGACACGATCGCAGCACCCCTCATGGAGACCCTCGCCTCGCCTTACCGAGAC
CSDV       ACTCACCGCGACACCATCGCCACCCCCCTCATGGAAGCCCTTGCTGAACCTTACCGCCAA
            *   ***  *  *****  *****    *  ** *************   ****   **       ********   *
           421                                                       480

OBDV       TCCCTTCGCGACTTCCCTTGGGCCGTCCCCGCCTCCGCCCTGCCCTTCCTCCAGGAATGT
CSDV       TCCTTGAGCACCTACCCATGGCACATTCCAACCAATCTTCAGCCCTTCCTCACCTCTTGC
           ***  *   **    **   ***    *** ***   *  *       *  *  ** ***********   **
           481                                                       540

OBDV       GGCATCACGGTCGCCGGCCACGGTTTCAAAGCTCATCCCCACCCTGTCCACAAAACCATC
CSDV       GGAATCACCACTGCTGGCCAAGGCTTCAAGGCCCACCCCTCACCCAGTGCACAAGACCATC
           **  *****   **  *****   **  *****   **   ** ** **  *****   ** *****  ******
           541                                                       600

OBDV       GAGACCCACCTCCTCCACAAGGTTTGGCCTCACTATGCCCAAGTCCCTTCTTCCGTCCTC
CSDV       GAGACCAATCTCCTCACTAATGTCTGGCCCCACTACGCCACCACTCCTAGTGGCGTCATG
           ******     ******    **  **   ****** ****   *  ***     * *    *****  *
           601                                                       660

OBDV       TTCATGAAGCCCTCGAAGTTCGCCAAACTCCAGCGGGGCAACGCCAACTTCTCCGCACTC
CSDV       TTCATGAAACCATCAAAGTTTGAGAAGCTCAAAATCAAACAGCCCAACTTCTCCAAGCTC
           ********  ** **  ******   ** **  *      **  *************     *    * **
           661                                                       720

OBDV       CACAACTATCGCCTCACCGCCAAAGACACCCCGCGGTATCCTAACACTTCAACCTCTCTC
CSDV       TACAACTACCGCATCACAGCCAAGGACACCACCCGTTACCCCTCCACTTCCCCAGACTTG
            *******  ***  ****  *****  ******    **  *****   **   *   *  *******    *  *
           721                                                       780
```

Figure 1 (continued)

```
OBDV    CCCGACACCGAGACCGCCTTCATGCATGACGCCCTCATGTATTACACCCCCGCTCAAATT
CSDV    CCCACCGAGGACACCTGCTTCATGCACGATGCCCTCATGTACTATTCCCCTGGACAGATC
        *** *  ** *** ******** ** ************ *  ****  *  ** **
        781                                                          840

OBDV    GTTGACCTGTTCCTTTCCTGCCCGAAGCTCGAGAAACTGTACGCCTCCCTTGTCGTCCCC
CSDV    TGTGACCTCTTCCTCTCCCGCCCCAGCCTCCAAAAGCTCTATGCTTCCCTTGTTGTTCCT
        ****** ***** ***  **** *  *** ** ** ** ** ******** ** **
        841                                                          900

OBDV    CCCGAGTCCTCCTTCACCTCTATCTCTCTCCATCCAGATCTTTACCGCTTTCGCTTTGAC
CSDV    CCGGAGAGCGACTTCACCACCATCTCCCTCTTCCCAGATCTCTACCGCTACCGGATCGAG
        ** ***  *  ******* *  ***** ***  ******** ******   * *  **
        901                                                          960

OBDV    GGGGACCGTTTGATTTATGAGTTGGAGGGCAACCCCGCCCACAACTACACCCAACCTCGA
CSDV    AAAGATCAGCTCATCTACGAGCTCGAGCAGAACCCCGCCCACAACTACATCCAGCCTCGC
        ** *    *  ** ** *** *  *  ** ******************* *** *****
        961                                                          1020

OBDV    TCCGCCCTCGACTGGCTCCGCACAACCACCATCCGCGGACCAGGCCGTTTCTCTCACCGTG
CSDV    TCTGCCATCGACTGGCTCAAGACCACCACCATCCGCTGCCAGGACCTCACTCTCACCATC
        ** *** *********** **  *********** * **** *   **  *********
        1021                                                         1080

OBDV    TCCAGGCTCGACTCGTGGGGTCCCTGCCATTCCCTCCTCATCCAGCGCGGCATTCCCCCC
CSDV    TCCCGCCTAGATTCCTGGGGCCCAGTCCACTCTCTCCTGATCCAAAGAGGCAAGCCCCCT
        ***  * ** **  * ***** ** * ***  *** ***** ****  * ***   ****

1081                                                         1140

OBDV    ATGCACGCCGAGCACGACTCCATCTCGTTCAGGGGTCCACGCGCCGTCGCCATTCCCGAG
CSDV    ATCCATCTTGAGGAGGACTCCATCAGCTTCCGTGCCCCAAAAGCAGTCCTCCTGCCTGAG
        ** **   *  *** * ********    *** **  *** ****  *  *  * * ***
        1141                                                         1200

OBDV    CCCTCCTCCCTCCACCAGGATCTGCGCCACCGTCTCGTTCCAGAGGACGTGTATAACGCC
CSDV    CCAGCTTCACTCTCCCAATCAGTCCGCGACCGCCTGGTCCCTGCTGATGTTTACCAGGCT
        **  *  ** ** ***  *  * ****** ** ** ** *  **  *** ***  ** *
        1201                                                         1260

OBDV    CTCTTCCTCTACGTCCGCGCTGTCCGCACGCTCCGCGTAACCGATCCCGCCGGCTTTGTC
CSDV    CTCTTCATCTATGTCCGGGCTGTCCGCACCCTCCGTGTGACCGACCCGGCTGGCTTCGTT
        ****** **** ***** ***********  *****  *  ****   **   **** **
        1261                                                         1320

OBDV    CGCACCCAGTGCTCTAAGCCCGAGTACGCTTGGGTCACTTCCTCCGCTTGGGACAACTTG
CSDV    CGCACTCAGATCTCTAAGCCCGAGTACTCTTGGGTCACTTCCTCCGCCTGGGACAATCTG
        ***** ***   *************** * *****************  ******* **
        1321                                                         1380

OBDV    GCCCACTTCGCCCTCCTCACCGCTCCACACCGGCCCCGCACCTCGTTCTACCTATTCTCC
CSDV    GCCCACTTTGCCTTGGCCACAGCTCCGCACAGACCCCACACCACCTACTTCCTGTTCAAC
        ********  *** *  * ***  * *** **  **** **** *** * * ** *  *
        1381                                                         1440

OBDV    TCTACCTTCCAGCGCCTTGAGCACTGGGTCCGCCATCACACCTT---CCTCCTCGCCGGC
CSDV    TCAACCGCTGCTCGGGTGCCCATTGGTTCCGCACTCATACCCTGGCTCCGCTCTCTGGC
        ** ***    **   *    *   ** *  ** ** ** **** *  *  *** * ***
        1441                                                         1500

OBDV    CTCACCACAGCCTTTGC------TCTC----CCGCCGTCTG-----CCTGGCTCGCGA--
CSDV    GCCACTGCTGCCGCCGCGAGCCTTCTCATGACCGCCAGCTGGGGATTCCGTGCCATGATC
        *** *  *** **                 *****  ***      **  *** ***
        1501                                                         1560

OBDV    -------ACCTCGTCGCCC-------------GCGC----------CTCCGCTTCACAC-
CSDV    TCCTCTCATCTTGTCTCCCTCTCCATCTGCAAGCGCTGGCTCAAAGCTCCTCCTCATCTC
        *  **  ***  ***                ****          **** * *  ***
        1561                                                         1620

OBDV    -----ATCCAAGG------CCTCGCGCTAGCCCGCCG-GTGGCTCA---TCACT--CCCC
CSDV    CTCTGGCCCGAGAAAGCTCCCTGGTTCCAGCTCACCCTGAGGCCCAAAGTCACTGGCCCT
        ** **         *** *  *** ** *  ***  *  *** *** *** **
        1621                                                         1680
```

Figure 1 (continued)

```
OBDV   CTCATCTCTTCCGCCCCCCTCCACCCCC--AAGCTTCGCTCTTCTTCTCCAGCGCAACT-
CSDV   CTGATTGACCTGCCCATTCTCCGACCCTTTAGGCTGTTCCCTTCCACATGCGCCAAACTG
       ** **         **    ****  ***   * ***    * ****  *     **  ****
       1681                                                      1740

OBDV   -----CCACCGGCCCGGTCCTTCTCCGTGGCTCCC----GCCTCGAG-------------
CSDV   GGCGCCAAGCACCCTGCTCTTGCCACATTGCTTCCTGCTGCTCCCAGGCCCACATGGCCC
            *  *    **  *  ** * *      *  *  *** **         **   *  **           *
       1741                                                      1800

OBDV   TTTGAGGCCTTCCCTTCTCTCGCC----CCACAACTCGCCCGTCGCTTTCC-----ATTC
CSDV   CTAAAGGTTGGCCTCGCACTCGCTGCTGTCCCAGTCTGCCTGTTCTTGTGGCGGAAATTC
          *  ***     **   *  *****       *  **      ***  **    *   *       ****
       1801                                                      1860

OBDV   CTCGCTCGCCTTCTCCCCCAGAA----------ACCCATCGACCCCTGGGTCGTC----G
CSDV   ATTGGTCCCGATTCTCCACAGGACATGCATGACAGCTATCATGCCATGTTTCATCCACAG
         *  * **  *   *   ** ***  *          *  ***   ** **   ** **         *
       1861                                                      1920

OBDV   C----GAGCCTCGCTGTCGC-CGTTGCTATACCCGCCGCCTCC---CTCGCCGTTCGCTG
CSDV   CCTTGGGGCCTCACTCTCACTCGCAAGGCTATCTGCTGCGATAGGGCCCCCTTTCTGCCC
       *    * *****  ** **  * **       ** ** **           *   * *  **
       1921                                                      1980

OBDV   GTTCTT--CGGCCCCGACAC---CCCCAAGCCATGC--ACGACCGATACCACACCATG-
CSDV   ATCCCTGTTGTTCCCAGCTCTGACTTCAAGGCCCCGCCAACACCTGCCACCCCACTATTG
         * *     *   ***    * *    *     * ****   **   **  *   *      *** ***  **
       1981                                                      2040

OBDV   --TTCCACCCC-----AGAGAGTGGCGCCTCACCCTGCCC----AGGGGCCCCATCTCAT
CSDV   ACTTCCATCCCTATTAAGGGTGTGGAGCCTCAAGTTTCTGGAGAAGGAGTACCTCCGCAG
         *****  ***          **  *  **** ******   * *         *** *   **   *  **
       2041                                                      2100

OBDV   GTGGC---------CGCTCCAGCTTC----TCCCCCCTTCCCC---ACCCACCTTCGCCC
CSDV   TCGGCTTCATCAACCGGCCCGGCATCGGACTCCCGTCGTGCCCCGCAACCAGCTTCATCA
        ***               **  **  ** **    ****   *  ***     * ***  * ***  ****  *
       2101                                                      2160

OBDV   ACT--CCCGCTCCCGACTCCCGAGC-------TGAACCCCTCCAGCCACCC---------
CSDV   ACTGGTCCGGATCCGCCCACCCAGAACACGAGTGCTGCCCCCAACCTCCCATCGAATCC
       ***    ***    ***   *  **   **          **   *** ***  **  ***
       2161                                                      2220

OBDV   ---------TCCGCTCCACCC-------------------TCGACCCACGAGC-------
CSDV   AAAGTTACCTTTGCCCAACCCATTGAGAGTGTGGCACCTGTAGTTCCAGGAGCAGGAGAA
                *  **   ****                             *  *   ***  ****
       2221                                                      2280

OBDV   ---------CGGCTCC--------------CGCCGATCTC-------GAGCCCCAAGCT
CSDV   CCTCCGCAGTCGGCTTCATCAACCGGCCCGGCATCGGTCTCCCGTCGTGACCCGCAAGTG
                *****  *            * ** ****       ** **  ****
       2281                                                      2340

OBDV   CCTCCGGC--CCACGCC------CCCCAGACCGAGCCTCCGAGT--CCCGTG--------
CSDV   GCTTCATCAACCACTCCGGATGCTCCCACCCTGGACGTCAGCGTGACCCCTCCAAAGACT
       **  *   *   ****  **    ****  *  *  **. *  **   *** *
       2341                                                      2400

OBDV   ATCGAGC--AAGAAGCGCGTCCGAATCCCCTTC-----CCGCTCCTGCCCCGCTT-----
CSDV   ATCTATCCTATTGACCACCTCCAGAACGACTTCGGCCCTTGCCGTTGCTCCGTCTGTGAA
       *** * *  *   * *   *   *** **  * ****     **   *** ***  *
       2401                                                      2460

OBDV   --------TCTGCTCCCACCCCCTCCGCTTC-CGCGCCTTCACTTGCCCCAAC--ACCC
CSDV   CCACTTCAGCCTGCCCCCGTCCCCTCCACTCCTCTCACCGTCTCGGATCATAAAGAAGCC
               ****  ***   ******* **  * *  * **  ** *     *  **   * **
       2461                                                      2520

OBDV   TCGGCCCCCGAGCCTCCCTCGCCGACC------GCTTCCGAGCAGGCCGCGTCCCTCATC
CSDV   CAGGACGCCGAAGCTCTTTCCTCGGCCCTCCAAGCCCTCGGGCTCGCTCCCACCCCACCA
       ** * ***** ** ***    **  **  **                **  ** ** **  *     ***
       2521                                                      2580
```

Figure 1 (continued)

```
OBDV    CCTGCTCCCTCTTCCGCCCTCGTCGTGGAGCCATCCGGCGTCGTCTCTGCCTCATCTTGG
CSDV    GCTCCACAGTCTCAGAACCTCACTGTAGAGTCCTCAGGAGCCATGCATGCCTCATCTTGG
        ** * * ***    ****  ** ***  * **  **  *  * *   ****************
        2581                                                    2640

OBDV    GGCGCCACCAACCAGCCGGCCGATCAAGTCG-ATGACTCCCCTCTCGCTCGCGATCCCAG
CSDV    GAT-CAGCTCTCCTCCCCATCATCTGACTGGGATCCTTCCCCTCTGGCCCGTGATAGCTC
        *  *  *   **  **   *    * *  **  ******** ** **  ***   *
        2641                                                    2700

OBDV    CGCCTCCGGCCCCGTCCGCTTCTATCGAGACCTCTTCCCCGCCAACTACGCGGGTGATTC
CSDV    CGCCTCTGGTCCCCCAGGCATGTACTCAGATCTCTTTCCAGCTCCCTACCTTCCAGGCAC
        ******  **  ***     **  *  **   *** ***** ** ****     *    *
        2701                                                    2760

OBDV    CGGCACCTTCGACTTCCGCGCCCGCGCCTCAGGCCGCTCTCCCACCCCATACCCCGCCAT
CSDV    CGGTCAGTTCATCTTCCGCTCCAGGGCCAATGGTCGGGCCAACATCCCTTATCCCGACAT
        ***   *** ******** ** * ***  ** **   *   ** *** ** ****  ***
        2761                                                    2820

OBDV    GGATTGCCTCCTCGTCGCCACCGAGCAAGCCACCCGCATCTCTCGAGAGGCCCTCTGGGA
CSDV    GGATTGCCTCTTGCTTTCCATCGAGCAAGCCACCCGCCTTCCCAAGGAGGCTCTCTGGGA
        **********  *  *   * ******************  * *   ***** ********
        2821                                                    2880

OBDV    CTGCCTCACAGCCACCTGCCCCGACTCATTCCTCGACCCCAAGAGCATCGCCCAGCATGG
CSDV    CACCCTCTGTGCCACATGCCCCGACTCTCTCCTTGATCCTGATACCATTCGCCGAGTCGG
        *  ****  *******  *********  **  **  **  *  ****  ****    **
        2881                                                    2940

OBDV    CCTCAGCACCGATCACTTCGTCATCCTCGCTCATCGCTTTTCCCT-ATGTGCCAACTTCC
CSDV    ATTGTCCACTGACCACTTTGCCATCCTGGCCCACCACTACTCCCTCAGGTGCCG-CTTTC
        *  ***  ** **** *  * * ****** ** ** **   **   *****   *
        2941                                                    3000

OBDV    ACTCCGCCGAGCACGTCATTCAGCTCGGGATGGCCGATGCCACCTCCATTTTCATGATCA
CSDV    ACACCGCCCATGGTGTCATTGAGCTCGGCATGGCTGATGCCACCTCCTCATTCGACATCG
        ** *****        ******* ***** ****** ************  ***  ***
        3001                                                    3060

OBDV    ACCACACGGCTGGCTCCGCGGGCCTCCCGGGCCACTTCTCCCTCCGCCTGGGTGACCAGC
CSDV    ACCACACTGCTGGCAAC--------CCCGGCCACTTCTCCCTCCGGCAATCTG-CCACT
        ****** * ******  *       ** ******************   *  **  * ***
        3061                                                    3120

OBDV    CCCGTGCCCTCAACGGTGGCCTCGCTCAGGACCTCGCCGTCGCCGCCCTCCGATTCAACA
CSDV    CCGAGGC--TAAATGGAGGGAATTGCTCAAGATCTCGCTGTGGCCGCTCTCAGGTTCAACA
        **  **    * **  **  **   * **  *    ****** **   *** **** *******
        3121                                                    3180

OBDV    TCTCCGGTGATCTCCTCCCAACCCGATCCGTTCACACTTACAGGTCTTGGCCAAAGCGCG
CSDV    TTGATGGCACTCTCCTCCCAATCCGCTCAGTTCATGTCTATTCCACTTGGCCAAAGAGAG
        *  **   ** ********** ***  *** ****  ** ***  ** ************ *
        3181                                                    3240

OBDV    CCAAGAACCTTGTGTCCAACATGAAGAACGGCTTTGACGGAGTCATGGCCAGCATCAACC
CSDV    CAAAGAACCTGTCGTCGAACATGAAGAACGGCTTTGACGGCATCATGGCCAACATCCACC
        * ******** ** *** ************************** ******** *** ***
        3241                                                    3300

OBDV    CGATCCGACCCAGCGATGCTCGCGAGAAGATCGTCGCCCTCGACGGTCTCCTAGACATTG
CSDV    CCACCAAGACCAATGAATCGAGAGAGAAGATCTTGGCACTCGATTCGCAGCTGGACATCG
        *  *   *** **    *  * * *  ********   *** ***    *    ****** *
        3301                                                    3360

OBDV    CCCGACCCCGATCCGTCCGCCTCATCCACATTGCTGGTTTCCCAGGCTGCGGAAAAACAC
CSDV    CTGTCAGGAGATCCGTCCGTCTGATCCATATTGCCGGGTTCCCAGGGTGCGGCAAGTCCT
        *           ************ ** ***** ****   **********  *****  **    *
        3361                                                    3420
```

Figure 1 (continued)

```
OBDV   ATCCGATCACCAAGCTCCTCCACACCGCCGCCTTCCGCGACTTCAAACTCGCCGTCCCGA
CSDV   TTCCCATCTCCCGCCTCCTCCGCACTCCAACCTTCAGGAACTTTAAGGTGGCAGTTCCCA
       *** *** **  ******* ***  * *****  *  ****  **  *  ** **  ** *
       3421                                                      3480

OBDV   CCACCGAGCTCCGGTCTGAGTGGAAAGAGCTCATGAAGCTCTCACCCTCTCAGGCCTGGC
CSDV   CTGTTGAGCTCCGAGCCGAGTGGAAAAACCATTACTGGTCTCCCGGCCTCAGAAGCCTGGC
       *   ********  *  **********  *  *   ***  ****  *  *******
       3481                                                      3540

OBDV   GCTTCGGCACCTGGGAGTCCTCCCTTCTCAAGAGCGCCAGGATCCTCGTGATCGATGAGA
CSDV   GCATCGGCACCTGGGAATCCTCTCTCCTCAAGTCTGCCCGGGTCCTGGTCATTGATGAAA
       ** ************* *****   ** ******    ***  ** **** ** ***** *
       3541                                                      3600

OBDV   TCTACAAGTTGCCCCGAGGGTACCTCGACCTAGCCATCCACTCCGACTCGTCCATCGAGT
CSDV   TCTACAAGATGCCAAGAGGCTACATTGATCTCGCCATCCACTCTGATCCCACCATTGAAA
       ********  ****  **** ***  *   ** ********** **  *  ****  **
       3601                                                      3660

OBDV   TTGTTATCGCCCTGGGAGATCCTCTGCAAGGCGAGTATCACTCCACTCATCCCAGCTCCT
CSDV   TGGTCATTGCTCTCGGTGATCCACTCCAAGGAGAGTACCACTCCACTCATCCTTCCTCTA
       *  ** **  ** ** ** ****  ** ***** ***** ************  ** *** ***
       3661                                                      3720

OBDV   CCAACTCTCGCCTCATTCCCGAAGTCAGCCATCTCGCTCCCTACCTCGACTACTACTGCC
CSDV   CCAACTCCCGCCTTCTCTCTGAGCCCCAGCATCTCTCCATGTACCTTGACTTCTACTGCT
       *******  *****  *  * **    ******* *     *****  ****  ****** *
       3721                                                      3780

OBDV   TCTGGAGTTACCGCGTCCCCCAAGACGTCGCCGCTTTCTTCCAGGTTCAGAGCCACAACC
CSDV   TGTGGTCCCACCGCGTTCCGCAGAACGTGGCCGCCTTCTTCCATGT-CAAGACCACCTCC
       *  ***       *******   *  **   ***** ********  **  * ***  * **
       3781                                                      3840

OBDV   CTGCTCTCGGGTTTGC-CCGTCTCTCGAAGCAGTTTCCCACGACCGGGCGCGTCCTCACC
CSDV   AAACAGCCTGGCTTCTGCCGCTACCAGAGAGAGCTGCCGAACTCCAGA---ATCCTGGCC
       *  *  **  **   ***   *  **  **  * **  *   ** *      **** **
       3841                                                      3900

OBDV   AACTCACAGAACTCGATGCTTACCATGACGCAGTGCGGCTACTCTGCCGTCACCATTGCC
CSDV   AACTCTCAGAATGCAGGCCATACCCTCCAGCAGTGTGGCTACGCTGCCGTCACCATTGCC
       ***** *****  *   *  *  ****  *  ***** ***** * ****************
       3901                                                      3960

OBDV   TCAAGCCAGGGTTCCACCTACAGCGGCGCCACGCACATCCACCTTGACCGCAACTCATCG
CSDV   TCCAGTCAGGGCTCCACCTATGAAAATGCGGCCTGCATTCACCTGGACCGAAACAGCTCC
       ** **  **** ******** *   **  ***  *** ***** * ****** *** **  **
       3961                                                      4020

OBDV   CTCCTCTCCCCTTCGAACTCCCTCGTCGCCCTCACTCGCTCGAGAACCGGCGTGTTCTTC
CSDV   TTGCTCTCCCCTGCTCACTCCATGGTTGCTCTCACTCGCTCAAAGGTTGGTGTCATCTTC
       *  ********** *  ***** *  ** ** **  ********  *  ** **  * ****
       4021                                                      4080

OBDV   TCCGGGGACCCTGCTCTTCTCAACGGTGGTCCCAACTCCAACCTCATGTTCTCTGCCTTC
CSDV   ACCGGCGATCCCGCCCAGCTCTCCAATGCTCCAAGCTCCAACCGAATGTTCTCAGAGTTC
       *****  **  **  *   ***  *   *  *  *** * ******** ********    ** *
       4081                                                      4140

OBDV   TTTCAGGGCAAGTCTCGCCACATTCGCGCCTGGTTCCCCACCCTTTTCCCTACGGCCACT
CSDV   TTCTCAGGCCGCACCCGCCCTCTTCATGACTGGTTCCACAATGAGTTCCCAAAGGCCACT
       **   ****  *    **** *  *   ** *********  *       ******  ** ******
       4141                                                      4200

OBDV   CTCCTCTTCTCCCCCCTCCGCCAACGCCACAACCGCCTCACTGGCGCCCTCGCTCCCGCC
CSDV   GTCCTCACCGAGCCCCTCAAGACTCGGGGGCCCCGCCTCACCGGTGCT-----------
       ***** *  *   *******    **  *  *********** ** **
       4201                                                      4260

OBDV   CAACCTTCCCACCTCCTGCTCCCTGACCTTCCGAGCCTCCCTCCTCTCCCCGCCTCCGGT
CSDV   --GCCTCACCA-----TACTCCAAGGCTGTCCCAATCCGCCA---------------AGC
       *** ***     * *****  *  *** *  *   **
       4261                                                      4320
```

Figure 1 (continued)

```
OBDV  CCCTACTCCCGCTCATTCCCAGTTCGATCTCGCTTCGCCGCGGCCGTCAAGCCTTCCGAC
CSDV  CTCCACCCCAGCTC-------------------------TCAAGCCTGATTTC
      * * ** ** ****                         ******** *
      4321                                                      4380

OBDV  CGGTCAGACGTCCTCTCGTGGGCCCCTATCGCCGTCGGTGACGGGGAAACCAACGCCCCT
CSDV  CAAGGGGACGTCATAATCTCAGCACCCATAGTTCTCGGCTCCGGCGAGCTCAATGCCCCT
      *   ****** *    *  ** ** ** *   ****   ***  **   *** ******
      4381                                                      4440

OBDV  CGCATTGACACCTCCTTCCTGCCCGAAACTCGCCGCCCCGCCTTCATTTTGATCTTCCCTCG
CSDV  CAAGTCTCCTCTCACTTCCTCCCCGAGACTCGCCGTCCTCTCCACTGGGACATTCCATCT
      *   *   *  *  ****** ***** ******** **   **  *  **  **** **
      4441                                                      4500

OBDV  TTCCGCCCCCA-AGCCCCACCGCCTCCCTCTGACCCAGCCCCTTCTGGGACCGCCTTTGA
CSDV  GCCATCCCTGAGAGTGCCACCAGACCGGACTCCACTGAGCCCACCACCTCCCATCCA-GA
      * ***  *  ** *****     *     ** *  *  *  **  *   *  ****  **
      4501                                                      4560

OBDV  GCCCGTTTACCCCGGCGAAACCTTCGAAAATTTGGTCGCCCACTTCCTTCCGGCTCACGA
CSDV  GCCAGTCTACCCCGGGGAAACTTTTGAGAATCTTGCTGCCCACTTTCTCCCTGCCCACGA
      *** ** ******** ***** ** ** *** *** ********* ** ** ** ****
      4561                                                      4620

OBDV  CCCCACTGACCGCGAAATCCACTGGCGTCGGCAGCTTTCCAACCAGTTTCCCCATGTCGA
CSDV  CCCCAACCGATCGTGAGATCTACTGGCAGGGTCAGCTGTCCAACCAGTTCCCACACATGCA
      ***   **  *  **  ** ****** *   ****** *********** ** *  * **
      4621                                                      4680

OBDV  TAAGGAGTACCACCTCGCGGCTCAGCCAATGACGCTCCTCGCTCCCATCCACGACTCCAA
CSDV  CAAGGAATTCCATTTGGCTGCACAACCCATGAGTCTCCTGGCTGCCGTTCATCAAGAGAA
      ***** *  *** *  * ** ** ** ** ***  ***** *** ** * *  *   **
      4681                                                      4740

OBDV  GCACGACCCCACCCTCCTTGCCGCCTCCATCCAGAAACGACTTCGATTTCGACCCTCCGC
CSDV  GCAAGATCCCACTCTACTGCCAGCTTCAATCCAAAAGAGACTCCGCTTCCGCCCCTCCGA
      *** ** ***** ** ** * ***** ** *****   ** **  * ***** *** ***
      4741                                                      4800

OBDV  CTCTCCCTACCGAATCTCCCCTCGTGACGAGCTGCTTGGCCAGCTCCTCTACGAGAGTCT
CSDV  CAAGCCCTACCAGATCACCCCAAAAGATGAAATCCTGGGCCAGCTCCTCTTTGAAGGCCT
      *  ******* *** ****  * **   *  * * ************** **  ** **
      4801                                                      4860

OBDV  CTGCCGCGCGTATCATCGTTCCCCAACCACCACCCACCCTTTCGATGAGGCCCTCTTCGT
CSDV  CTGCCGAGCCTACCACAGATCTCCATTTCACACTGAGGCCTTTGATCCCGTGCTTTTCGC
      ****** ** ** ** *  * ** ***     * *  * **  *** * ** ** ****
      4861                                                      4920

OBDV  CGAGTGTATCGACCTGAACGAATTCGCTCAACTCACCAGCAAAACTCAGGCCGTCATCAT
CSDV  CGAGTGCATCAATCTCAATGAGTTCGCCCAGCTCTCGTCCAAGACCCAGCCTACTATTAT
      ****** *** * **  ** ** ***** ** *** *  ** ***  *** ***  ** *
      4921                                                      4980

OBDV  GGGCAACGCCCGCCGCTCTGACCCAGACTGGCGCTGGTCCGCCGTCCCGGATCTTCAGCAA
CSDV  GGGCAATGCTCGCCGCTCAGACCCTGATTGGCGGTGGAGCGCAGTTCGCATCTTCTCCAA
      ****** ** ******** *****  * *****  **   *** *  * *****  ***
      4981                                                      5040

OBDV  AACCCAGCACAAGGTCAACGAAGGTTCGATCTTTGGAGCCTGGAAAGCTTGCCAGACCCT
CSDV  GACCCAACACAAGGTGAATGAAGGGTCCATTTTTCCGCTCCTGGAAGGCCTGCCAAACTTT
      *****  ******** ** ***** ** ** ***   *  *****  ** *****  * *
      5041                                                      5100

OBDV  CGCTCTCATGCACGACGCCGTCGTTCTGCTCCTTGGCCCCGTCAAGAAGTATCAACGCGT
CSDV  GGCTCTCATGCATGATGCTGTTGTTCTAATCCTGGGCCCTGTCAAGAAGTACCAGCGAGT
      ************  ** ** ** *****  ***  ***** ********** ** **  *
      5101                                                      5160

OBDV  CTTCGATGCTCGAGACCGCCCCGCCCACCTCTACATCCACGCCGGCCAGACGCCCTCTTC
CSDV  CTTTGATCAGAGAGACCGACCCCGACACCTTTACATCCATGCAGGCAACACTCCATCACA
      *** ***   ** *****  ***  ***** ********  * ***  *** *** ** *
      5161                                                      5220
```

Figure 1 (continued)

```
OBDV   CATGAGCCTGTGGTGCCAGACCCACCTCACCCCCGCTGTCAAGCTCGCGAACGACTACAC
CSDV   AATGAGCAACTGGTGTCAACAGCATCTCACTACTGCCGTCAAGTTGGCCAATGACTACAC
       ******  ***** **   ** *****  *  ** ****** *  ** ** *********
       5221                                                     5280

OBDV   CGCTTTCGACCAGTCTCAGCATGGCGAGGCCGTCGTCCTCGAGAGAAAGAAGATGGAACG
CSDV   TGCCTTCGACCAGTCTCAGCATGGTGAGGCGGTCGTCCTTGAAAGAAAGAAAATGGAAAG
       ** ********************* ***** ******** ** ******* ****** *
       5281                                                     5340

OBDV   CCTTTCCATCCCGGATCACCTCATCTCCCTCCACGTTCACCTTAAGACCCCATGTCGAAAC
CSDV   ACTCTCCATCCCCCAGGCTCTCATTGATCTTCACATCCATCTCAAAACCCATGTTTCCAC
       ** ********   *    ** *****  ** *** ** ** ** *******  **
       5341                                                     5400

OBDV   CCAGTTTGGCCCTCTCACCTGCATGCGCCTAACCGGCGAGCCTGGCACCTACGACGACAA
CSDV   CCAGTTTGGCCCCTCACATGCATGCGCCTGACTGGGGAGCCTGGCACTTATGATGATAA
       ************  ****  ************ **  ************ ** ** **
       5401                                                     5460

OBDV   CACTGACTATAACCTCGCCGTCATCAACCTCGAGTACGCGGCTGCCCACGTCCCGACCAT
CSDV   CTCTGACTACAATCTTGCAGTTGTCAACTGTGAGTACATGGCTGCCAACACTCCCACTAT
       * ******* ** ** ** **  ** ***  ******   ****** ** ** ** **
       5461                                                     5520

OBDV   GGTCTCGGGCGACGATTCACTCCTTGACTTCGAGCCCCCACGCCGCCCAGAGTGGGTCGC
CSDV   GGTCTCAGGCGACGACTCCCTCCTGGATCGTGAGCCTCCCACTCGCCCTGAATGGGTCAT
       ****** ********  ** ***** **   ***** **   ***** ** ******
       5521                                                     5580

OBDV   CATCGAACCTCTTTTAGCCCTCCGCTTCAAGAAGGAGCGCGGTCTGTATGCCACCTTCTG
CSDV   CCTCCAGCCTCTTCTCAGTCTCCGCTTCAAGAAAGAAAGGGGTCGGTACGCCACCTTCTG
       * ** * ******  *    ************** **  *** ** *** *********
       5581                                                     5640

OBDV   CGGCTACTACGCCTCGCGAGTTGGCTGCGTCCGATCTCCCATCGCCCTCTTCGCTAAGCT
CSDV   TGGCTACTACGCCTCCCATGTCGGCTGTGTCCGCTCCCCCGTGGCTCTCTTTGCCAAGCT
       ************** *  ** ***** ***** **  ***  **  ***** ** ****
       5641                                                     5700

OBDV   CGCCATCGCCGTCGACGACTCATCCATCTCCGACAAGCTCGCCGCATACCTCATGGAGTT
CSDV   GGCCATAGCTGTCGATGACGGCTCCATCTCTGACAAAATGGCCTATACCTCTCTGAATT
       ***** ** ***** ***   ****** **** *** * ** ****** ** **

5701                                                     5760
OBDV   CGCGGTCGGTCACTCTCTCGGCGACTCTCTTTGGTCCGCCCTCCCCCCTGTCCGCCGTCCC
CSDV   TGCTCTTGGCCACTCCCTTGGAGACCATCTCTGGGAAGCTTTGCCCCTCGAGGCCGTTCC
       **  *  ***** ** ** **     *** *** *** ** ** ***  ** ***** **
       5761                                                     5820

OBDV   CTTTCAGTCAGCCTGTTTCGATTTCTTCTGCCGCCGCGCTCCCCGCGATCTAAAGCTCGC
CSDV   CTTCCAATCTGCCTGCTTTGACTTCTTCTGCCGCCGGGCCCCCAGACACCTCAAACTCTC
       *** ** **  ***** **  ** ********** ***  ***   * ** *** *** *
       5821                                                     5880

OBDV   CCTTCACCTGGGCGAAGTCCCTGAAACCATCATCCAACGCCTC---TCCCACCTCTCCTG
CSDV   TCTCATGCTCGGCGAGGTCCCAGAATCCATCATTGCCCGCATCGGGTCATCCTTGAAGTG
       ** *   ** ***** ***** ***  ****** **  ***  ***  ** * * *
       5881                                                     5940

OBDV   GCTATCCCACGCCGTCTACAGCCTCCTCCCATCTCGCCTTCGCCTCGCCATCCTTCACAG
CSDV   GGCCTCTCATGCCATCTACACCACACTCTCCTCTGCCGCTCGAGTGGCCATTCTGAGATC
       *   **  ** *** *****  *  ***  ***** * * **    ***** **
       5941                                                     6000

OBDV   CTCACGCCAGCACCCGTTCCCTCCCCGAAGACCCAGCCGTTTCTTCGCTTCAGGGTGAATT
CSDV   CTCCCGCAACAGCAGATCCATGCCAGATGACCCCGACACCACTCTGCTACAAGGTGAATT
       *** ***  * *  *** *   ** ** **** ** ** **  ** ** * *********
       6001                                                     6060

OBDV   GCTTCAGACGTTCCATGCTCCA---ATGCCCTCTCTCCCTTCACTCCCACTCTTCGGCGG
CSDV   GCTTCAGCACTTTCAAGTACCATTCATGCAATCTGACACTCTCCTGCCTCTCACTGGTGG
       *******  **  ** *   ***  *  ** *** ** ** **  ** ** **
       6061                                                     6120
```

Figure 1 (continued)

```
OBDV    TCTATCTCCCGACAACATCCTCACTCCCCACGAGTTCCGCACCGCCCTCTACGAAAGCTC
CSDV    T---TCCTCTGCTCCCATCCTCACACCAGAAGCCTTCTCCACCTCCCTC----------
        *   **  *  *   ********  **  *  *  ***  ****  *****
        6121                                                       6180

OBDV    CGCCTACCCTACTCCTCCCAACTCTCCGACCTCCATGTCAGGAATCCATGCCTCGCAAGT
CSDV    -GCCT--------------------TCTCCATGGCCAG---CGATGCC---CAAGC
         ****                     ******* *  *  * *****    ****
        6181                                                       6240

OBDV    TGGTCCGCCCCCCGCCAGCGATGATCGCACTGACCGCCAGCCTTCTCTTCCTCTTGCTCC
CSDV    AGGTCCGGCCCCCAGTCGCGATGATCGCGTTGACCGCCAGCCTCGCCTTCCTGCTGCTCC
         ***** ***** *   **********  ************  ****** ** ** ****
        6241                                                       6300

OBDV    TCGTATTGTGGAGAGCTCTCTCGCCGTGCCGCACGTCGACGTCCCGTTCCAATGGGCCGT
CSDV    TCGCGTTGCTGAAGTTGGTCTCAATGCCCGTCGGTCGACTACCCGTTCCAGTGGGTCGT
        ***  ***  **     *  ***       *  ******  ********* **** ***
        6301                                                       6360

OBDV    CGCCGTCGTACGCCGGAGACTCCGCCAAGTTCCTCACCGACGACCTCTCAGGATCCTCTCA
CSDV    CGCCTCCTACGACGGATCAGAAGCCAAGAACCTAAGTGATGATCTCTCTGGCTCTGCCAC
        ****  *  **** ***       ****** **   *  **  *****  *  *  *
        6361                                                       6420

OBDV    CCTGAGCCGCCTCACCATCGGCTATCGCCACGCCGAGCTCATCTCCGCCGAGCTCGAGTT
CSDV    TCTCACCAAAGTCATGGCCAACTACCGACATGCTGAGCTCACATCTGTTGAGCTGGAGGT
         ** *  *     ***     *  *** ** ** *******  ** *  ***** *** *
        6421                                                       6480

OBDV    CGCCCCCCTTGCCGCCGCCTTCGCCAAGCCCATCTCCGTCACCGCCGTCTGGACCATAGC
CSDV    CTGCCCTCTTGCTGCAGCCTTCTCCAAGCCCATCTCTGTGTCGGCCGTCTGGACCATTGC
        *   ***   ***  ** ****** ***********  **   ************  **
        6481                                                       6540

OBDV    CTCCATCGCCCCAGCCACCACCACCGAGCTCCAGTACTACGGTGGCCGACTCCTCACCCT
CSDV    CTCCATCTCTCCAGCTTCCGCCTCTGAAACCTCCTACTATGGCGGTCGACTCTTCACTGT
        *******  * *****   * **    ***    ********* ** ****** ****
        6541                                                       6600

OBDV    CGGAGGCCCCGTCCTCATGGGCTCCGTCACCCGCATCCCAGCCGACCTCACCCGCCTCAA
CSDV    TGGCGGTCCTGTCCTCATGTCCAGCACCACCCATCTCCCTGCTGATCTCACCCGCCTCAA
        *  **  ** *********   *     * * **** *** **  ** *********
        6601                                                       6660

OBDV    CCCCGTCATCAAGACCGCCGTGGGCTTCACTGACTGCCCCCGCTTCACCTACTCCGTCTA
CSDV    TCCTGTGCTCAAGGGCCCCGTCAAGTACACAGACTGCCCCAGATTCTCCTACTCCGTCTA
         **  **  ****    ****  *   *** *********   **   ************
        6661                                                       6720

OBDV    TGCCAACGGCGGGTCCGCCAACACTCCTCTCATCACCGTCATGGTGCGAGGAGTTATCCG
CSDV    CTCCAATGGCGGGAACCAAGGGCACCAATCTCTGCACCATCATCCTCCGGGGAGTTGTCCG
        ****  ***** **  *  ***  ****  *** * ****  **
        6721                                                       6780

OBDV    CCTCTCCGGCCCTTCGGGCAACACCGTCACCGCCACCTAAGCCCTCTCACCGGTTTCAAC
CSDV    CCTCAGCGGCCCCTCCGGTAATCTTCTCGCT--TAGGCGAGCCTCTTCA--GGT---GAA
        ****  ****** ** ** ** ** ** **    * * ***** ****  ***    *
        6781                                                       6840

OBDV    AGGAGTTTCTTCCTCGTTCTTCTCCTGACGACCAATGAACGTTGCTTATCCCCCCTTCAC
CSDV    GGAAAACACCTCCTGGTCT--------CAGCCAGGTAATGATGCTAAACCTCCCC---C
         *  *   * **** **            *  **   ** * *** * ** ****    *
        6841                                                       6900

OBDV    ATCCCTCCGTTTCCCCCTCCGTTTTCCTCTCTGTTCCATTCCCCCTCTCCCTCCCCGTCT
CSDV    GCTCAAGCAGCAATGCCTAGGGTTGCCGGTCGATCCAAAGACCGTTTTTCTTTATTATTT
          *    *    *   ** ** **   * ** * *          ** *  **     *
        6901                                                       6960

OBDV    CAGCAATGAGTAAGGTTCCAGGTCGATTCAAAGACCTGATGGGATTTTCCTCGG
CSDV    AATAAAAAAAAAAAAAAA------------------------------------
         *    ** *  **
```

Figure 2

Comparison of CSDV polypeptide domains with those from others *Tymoviridae* virus (OBDV, GAMaV and GFkV)

a) Methyltransferase/Protease/Helicase/RNA-dependent RNA polymerase)

```
OBDV    ------------------MTTY-AFHPLLP------------------------------
CSDV    MDRISARIPVAPASAGPTEYTPYPHTHPLLPRGVFTSGPIQPCLHFLPHHAQDAPIRCYR
                          *.*  *****
        1                                                          60

OBDV    ------------------TPTSFATITGGGLKDVIETLSSTIHRDTIAAPLMETLASPYR
CSDV    PLTFANHLRYDRSASSLKTPPVKLPLTGGTLADAILSLAPTTHRDTIATPLMEALAEPYR
                          **.  .:*** * *.* :*:.* ******:****:**.***
        61                                                        120

OBDV    DSLRDFPWAVPASALPFLQECGITVAGHGFKAHPHPVHKTIETHLLHKVWPHYAQVPSSV
CSDV    QSLSTYPWHIPTNLQPFLTSCGITTAGQGFKAHPHPVHKTIETNLLTNVWPHYATTPSGV
        :**  :** :*:.  *** .****.**:*************:**  :****** .**.*
        121                                                       180

OBDV    LFMKPSKFAKLQRGNANFSALHNYRLTAKDTPRYPNTSTSLPDTETAFMHDALMYYTPAQ
CSDV    MFMKPSKFEKLKIKQPNFSKLYNYRITAKDTTRYPSTSPDLPTEDTCFMHDALMYYSPGQ
        :******* **:  :.*** *:***:***** ***.**..**  :*.********:*.*
        181                                                       240

OBDV    IVDLFLSCPKLEKLYASLVVPPESSFTSISLHPDLYRFRFDGDRLIYELEGNPAHNYTQP
CSDV    ICDLFLSRPSLQKLYASLVVPPESDFTTISLFPDLYRYRIEKDQLIYELEQNPAHNYIQP
        * ****.* *.*:***********.**:***.*****:*  *:*:****** ***** **
        241                                                       300

OBDV    RSALDWLRTTTIRGPGVSLTVSRLDSWGPCHSLLIQRGIPPMHAEHDSISFRGPRAVAIP
CSDV    RSAIDWLKTTTIRCQDLTLTISRLDSWGPVHSLLIQRGKPPIHLEEDSISFRAPKAVLLP
        ***:***:*****  ::**:******** ********  **:* *:******.*:**  :*
        301                                                       360

OBDV    EPSSLHQDLRHRLVPEDVYNALFLYVRAVRTLRVTDPAGFVRTQCSKPEYAWVTSSAWDN
CSDV    EPASLSQSVRDRLVPADVYQALFIYVRAVRTLRVTDPAGFVRTQISKPEYSWVTSSAWDN
        **:**  *.:*.****  *:*:*** :***:************ *****.*********
        361                                                       420

OBDV    LAHFALLTAPHRPRTSFYLFSSTFQRLEHWVRHHTFLLAGLTTAFALPPSAWLANLVARA
CSDV    LAHFALATAPHRPHTTYFLFNSTAARVAHWFRTHTLAPLSGATAAAASLLMTASWGFRAM
        ****** ******:*::**.** *: **.* **:     .:** *    :  _
        421                                                       480

OBDV    SASHIQGLALARRWLITPPHLFRPPPPPSFALLLQRNSTGPVLLRGSRLEFEAFPSLAPQ
CSDV    ISSHLVSLSICKRWLKAPPHLLWPEKAPWFQLTLRPKVTGPLIDLPILRPFRLFPSTCAK
        :*:  .*::. :*** :****  *    .*  * *  *:  ***::    *.  *** ..:
        481                                                       540

OBDV    LARRFPFLARLLPQKPIDPWVVASLAVAVAIPAASLAVRWFFGPDTPQAMHDRYHTMFHP
CSDV    LGAKHPALATLLPAAPRPTWPLKVGLALAAVPVCLFLWRKFIGPDSPQDMHDSYHAMFHP
        *. :.* ** *** *   .* :     . ..*:*.. :  * *:***:** *** **:****
        541                                                       600

OBDV    REWRLTLPRGPISCGRSSFSPLPHPPSP-TPAPDSRAEPLQ---------------PP
CSDV    QPWGLTLTRKAICCDRAPFLPIPVVPSSDFKAPPTPATPLLTSIPIKGVEPQVSGEGVPP
        : * ***.* .*.*.*:.*  *:*  **.   **  : * **                **
        601                                                       660

OBDV    SAPPST-------HEPAPADLEPQAPPAHAPQTEPPSPVIEQEARPNPLPAPAPLS----
CSDV    QSASSTGPASDSRRAPQPASSTGPDPPTQNTSAAPQPPIESKVTFAQPIESVAPVVPGAG
        .:..**       : * **.   **::  ..:  * .*: .: :   ..:*: : **:
        661                                                       720

OBDV    --------------------APTPSASAPSLAPTP--------------------
CSDV    EPPQSASSTGPASVSRRDPQVASSTTPDAPTLDVSVTPPKTIYPIDHLQNDFGPCRCSVC
                            :.**.*.: ..:: **
        721                                                       780
```

Figure 2 (continued)

```
OBDV    ----SAPEPPSP--------------TASEQAASLIPAP----SSALVVEPSGVVSASS
CSDV    EPLQPAPVPSTPLTVSDHKEAQDAEALSSALQALGLAPTPPAPQSQNLTVESSGAMHASS
         .**  *.:*              :::  ** .* *:*      *. *.**.**.: ***
        781                                                       840

OBDV    WGATNQPADQVDDSPLARDPSASGPVRFYRDLFPANYAGDSGTFDFRARASGRSPTPYPA
CSDV    WDQLSSPSSDWDPSPLARDSSASGPPGMYSDLFPAPYLPGTGQFIFRSRANGRANIPYPD
        *.  ..*:.: * ******.*****  :* ***** *  .:* * **:**.**:  ***
        841                                                       900

OBDV    MDCLLVATEQATRISREALWDCLTATCPDSFLDPKSIAQHGLSTDHFVILAHRFSLCANF
CSDV    MDCLLLSIEQATRLPKEALWDTLCATCPDSLLDPDTIRRVGLSTDHFAILAHHYSLRCRF
        *****::  *****: .***** * ******:***.:* : *******.****::** ..*
        901                                                       960

OBDV    HSAEHVIQLGMADATSIFMINHTAGSAGLPGHFSLRLGDQPRALNGGLAQDLAVAALRFN
CSDV    HTAHGVIELGMADATSSFDIDHTAGN---PGHFSLRQSATPR-LNGGIAQDLAVAALRFN
        *:*. **:******** * *:****.   *******  .   **  ****:*********
        961                                                       1020

OBDV    ISGDLLPTRSVHTYRSWPKRAKNLVSNMKNGFDGVMASINPIRPSDAREKIVALDGLLDI
CSDV    IDGTLLPIRSVHVYSTWPKRAKNLSSNMKNGFDGIMANIHPTKTNESREKILALDSQLDI
        *.* *** ****.*  :******** ********:**.*:*   ..::****:***. ***
        1021                                                      1080

OBDV    ARPRSVRLIHIAGFPGCGKTHPITKLLHTAAFRDFKLAVPTTELRSEWKELMKLSPSQAW
CSDV    AVRRSVRLIHIAGFPGCGKSFPISRLLRTPTFRNFKVAVPTVELRAEWKTITGLPASEAW
        * .****************..**::**:*.*:**:**:***.****.***: :  *.:**
        1081                                                      1140

OBDV    RFGTWESSLLKSARILVIDEIYKLPRGYLDLAIHSDSSIEFVIALGDPLQGEYHSTHPSS
CSDV    RIGTWESSLLKSARVLVIDEIYKMPRGYIDLAIHSDPTIEMVIALGDPLQGEYHSTHPSS
        *:************:*******:****:*******..:**:*******************
        1141                                                      1200

OBDV    SNSRLIPEVSHLAPYLDYYCLWSYRVPQDVAAFFQVQSHNPALGFARLSKQFPTTGRVLT
CSDV    TNSRLLSEPQHLSMYLDFYCLWSHRVPQNVAAFFHVKTTSKQPGFCRYQRELPNS-RILA
        :****:.*  .**: ***:*****:****:******:*:..  *.** :: .  *:*:
        1201                                                      1260

OBDV    NSQNSMLTMTQCGYSAVTIASSQGSTYSGATHIHLDRNSSLLSPSNSLVALTRSRTGVFF
CSDV    NSQNAGHTLQQCGYAAVTIASSQGSTYENAACIHLDRNSSLLSPAHSMVALTRSKVGVIF
        ****:  *: ****:************...*:* :************.:*.******:..**:*
        1261                                                      1320

OBDV    SGDPALLNGGPNSNLMFSAFFQGKSRHIRAWFPTLFPTATLLFSPLRQRHNRLTGALAPA
CSDV    TGDPAQLSNAPSSNRMFSEFFSGRTRPLHDWFHNEFPKATVLTEPLKTRGPRLTGAAS--
        :**** *...*.** *** **.*::* ** . **.**:* .**: * *****  :
        1321                                                      1380

OBDV    QPSHLLLPDLPSLPPLPASGPYSRSFPVRSRFAAAVKPSDRSDVLSWAPIAVGDGETNAP
CSDV    -------------------PYSKAVPIRQASTPALKPDFQGDVIISAPIVLGSGELNAP
                           ***:. *:*. .:.*:**. .**:  ****:** * **
        1381                                                      1440

OBDV    RIDTSFLPETRRPLHFDLPSFRPQAPPPPSDPAPSGTAFEPVYPGETFENLVAHFLPAHD
CSDV    QVSSHFLPETRRPLHWDIPSAIPESATRPDSTEPTTSHPEPVYPGETFENLAAHFLPAHD
        :::.: **********:*:** *:.. *... *:  :. *************.*******
        1441                                                      1500

OBDV    PTDREIHWRRQLSNQFPHVDKEYHLAAQPMTLLAPIHDSKHDPTLLAASIQKRLRFRPSA
CSDV    PTDREIYWQGQLSNQFPHMDKEFHLAAQPMSLLAAVHQEKQDPTLLPASIQKRLRFRPSD
        ******:*: .*******:***:******:**:.:*..*:*****.:************.
        1501                                                      1560

OBDV    SPYRISPRDELLGQLLYESLCRAYHRSPTTTHPFDEALFVECIDLNEFAQLTSKTQAVIM
CSDV    KPYQITPKDEILGQLLFEGLCRAYHRSPFHTEAFDPVLFAECINLNEFAQLSSKTQATIM
        .**:*.*:**:*****:*.********  *..** .**.***:********:*****.**
        1561                                                      1620

OBDV    GNARRSDPDWRWSAVRIFSKTQHKVNEGSIFGAWKACQTLALMHDAVVLLLGPVKKYQRV
CSDV    GNARRSDPDWRWSAVRIFSKTQHKVNEGSIFRSWKACQTLALMHDAVVLILGPVKKYQRV
        ******************************:.******************:********
        1621                                                      1680
```

Figure 2 (continued)

```
OBDV    FDARDRPAHLYIHAGQTPSSMSLWCQTHLTPAVKLANDYTAFDQSQHGEAVVLERKKMER
CSDV    FDQRDRPRHLYIHAGNTPSQMSNWCQQHLTTAVKLANDYTAFDQSQHGEAVVLERKKMER
        ** **** *******:*** ** *** ***.****************************
        1681                                                    1740

OBDV    LSIPDHLISLHVHLKTHVETQFGPLTCMRLTGEPGTYDDNTDYNLAVINLEYAAAHVPTM
CSDV    LSIPQALIDLHIHLKTHVSTQFGPLTCMRLTGEPGTYDDNSDYNLAVVNCEYMAANTPTM
        ****: **.**:****** .********************:****.:* ** **:.***
        1741                                                    1800

OBDV    VSGDDSLLDFEPPRRPEWVAIEPLLALRFKKERGLYATFCGYYASRVGCVRSPIALFAKL
CSDV    VSGDDSLLDREPPTRPEWVILQPLLSLRFKKERGRYATFCGYYASHVGCVRSPVALFAKL
        ********* *** ***** ;:***.:******** ********:*******:******
        1801                                                    1860

OBDV    AIAVDDSSISDKLAAYLMEFAVGHSLGDSLWSALPLSAVPFQSACFDFFCRRAPRDLKLA
CSDV    AIAVDDGSISDKMASYLSEFALGHSLGDHLWEALPLEAVPFQSACFDFFCRRAPRHLKLS
        ******.*****:*:** ***:****** **.**** ******************.***:
        1861                                                    1920

OBDV    LHLGEVPETIIQRL-SHLSWLSHAVYSLLPSRLRLAILHSSRQHRSLPEDPAVSSLQGEL
CSDV    LMLGEVPESIIARIGSSLKWASHAIYTTLSSAARVAILRSSRNSRSMPDDPDTTLLQGEL
        * ******:** *: * *.* ***:*; *.*  *;***;***: **:*:** .: *****
        1921                                                    1980

OBDV    LQTFHAPMPSLPSLPLFGGLSPDNILTPHEFRTALYESSAYPTPPNSPTSMSGIHASQVG
CSDV    LQHFQVPFMQSDTLLPLTGGSSAPILTPEAFSTSLAFSMAS-------------DAQAG
        ** *;.*;.   ;*   ; * * *. ****.* * *;* * *             :*.*
        1981                                                    2040

OBDV    PPPASDDRTDRQPSLPLAPRIVESSLAVPHVDVPFQWAVASYAGDSAKFLTDDLSGSSHL
CSDV    PAPSRDDRVDRQPRLPAAPRVAEVGLNAPSVDYPFQWVVASYDGSEAKNLSDDLSGSATL
        *.*: ***.**** ** ***:.* .* .* ** ****.****  **..** *:******: *
        2041                                                    2100

OBDV    SRLTIGYRHAELISAELEFAPLAAAFAKPISVTAVWTIASIAPATTTELQYYGGRLLTLG
CSDV    TKVMANYRHAELTSVELEVCPLAAAFSKPISVSAVWTIASISPASASETSYYGGRLFTVG
        ::: .****** *.***..****** :****:.******:;*:: * .*****.*:.*
        2101                                                    2160

OBDV    GPVLMGSVTRIPADLTRLNPVIKTAVGFTDCPRFTYSVYANGGSANTPLITVMVRGVIRL
CSDV    GPVLMSSTTHLPADLTRLNPVLKGPVKYTDCPRFSYSVYSNGGTKGTNLCTIILRGVVRL
        *****.*.*:;;:**********:* .* ;******;****:***:  .* * *;::***:**
        2161                                                    2220

OBDV    SGPSGNTVTAT
CSDV    SGPSGNLLA--
        ****** ::
```

(b) Coat Protein 1

```
GAMaV    SSAPQLTSEAFSLTLAQSMASPNVQAGPPPPSDDRTDRQPPLPRAPRLVEDASAIPFVDY
CSDV     SSAPILTPEAFSTSLAFSMAS-DAQAGPAPSRDDRVDRQPRLPAAPRVAEVGLNAPSVDY
         **** **.**** :** **** :.****.*. ***.**** ** ***:;.*  .  * ***
         1                                                          60

GAMaV    PFQWVVASYDGSTAKNLTDVLSGSKTLSTITANYRHAELLSVELEFAPLAGSFSKPITLS
CSDV     PFQWVVASYDGSEAKNLSDDLSGSATLTKVMANYRHAELTSVELEVCPLAAAFSKPISVS
         ************ *****:*.**** **:;;  .*******.*****.*  ***.*****:;*
         61                                                        120

GAMaV    AVWTVGSITPATTTETSYYGGRVITIGGPVLMNSTTAVPADLRRLNPIIKDQISYTDCPR
CSDV     AVWTIASISPASASETSYYGGRLFTVGGPVLMSSTTHLPADLTRLNPVLKGPVKYTDCPR
         ****; .**:**:;:******.: *.******;***  **** ****:;*.  :*****
         121                                                       180

GAMaV    FSYSVYANGGTAGTNLVTVLIRGVVRLRSPSGNLLA
CSDV     FSYSVYSNGGTKGTNLCTIILRGVVRLSGPSGNLLA
         ******:****.**** *:;******** .******
```

Figure 2 (continued)

(c) Coat Protein 2

```
GAMaV      MASPNVQAGPPPPSDDRTDRQPPLPRAPRLVEDASAIPFVDYPFQWVVASYDGSTAKNLT
CSDV       MAS-DAQAGPAPSRDDRVDRQPRLPAAPRVAEVGLNAPSVDYPFQWVVASYDGSEAKNLS
           *** :.****.*. ***.**** ** ***:.*  . * ****************.****:
           1                                                          60

GAMaV      DVLSGSKTLSTITANYRHAELLSVELEFAPLAGSFSKPITLSAVWTVGSITPATTTETSY
CSDV       DDLSGSATLTKVMANYRHAELTSVELEVCPLAAAFSKPISVSAVWTIASISPASASETSY
           * **** **:.: ******** ***** ..***.:*****::*****:.**:**::****
           61                                                         120

GAMaV      YGGRVITIGGPVLMNSTTAVPADLRRLNPIIKDQISYTDCPRFSYSVYANGGTAGTNLVT
CSDV       YGGRLFTVGGPVLMSSTTHLPADLTRLNPVLKGPVKYTDCPRFSYSVYSNGGTKGTNLCT
           ****::*:******.*** :**** ****::*. :.************:**** **** *
           121                                                        180

GAMaV      VLIRGVVRLRSPSGNLLA
CSDV       IILRGVVRLSGPSGNLLA
           :::****** .*******
```

(d) Putative Movement Protein

```
GFkV       MTSRAPSPPTPPCPSPPALKSSPSPVPTATPASPPLKPLSNPLPPPPPTPRPSTSAGPST
CSDV       MISLALPLSPKSWPTTDMLSSHLLSWRSALLLQP--------SPSPSLCRPSGPLPPSL
           * * *  .. . *:.  *.*   . :*   .*       .*.*. ***  .  **
           1                                                          60

GFkV       PLPPPALRSSPSSALNASRGAPSTSPPPSSSPPSSPASTPPSRTPSPTPTAPASPVASTA
CSDV       QLPP--LKPPTMAVDSSLLAVLSSCPAPPISLLISPASILCSRAPSSTQTAPDSPTPSTP
            ***  *:... :. .:   .. *:.*.*. *    ****   **:**.* *** **..**.
           61                                                         120

GFkV       MTPASPSVPPPPSAAPSSSAALSSAPPPSTAPLPRHEPRPPPPLPPPLQPPPGVRVPRSV
CSDV       MAEPRAPISAPSSSGELS----ASAAPPVIFSLRRASSGEGKHLLVSAR-----------
           *: .  ..:..*.*:..   *     :**.**     .* *  ..     *   . :
           121                                                        180

GFkV       AFPLPLARELPPLRLPPAPYLHPLLARLAPLRLRPPPDLPSPPLSPPLSPPLSPISPLHA
CSDV       ------------------------------------------------------------
           181                                                        240

GFkV       PAPPPHPDPVLLPALSLAISRAAPDLLRLLSLLSPPSLFLLFTLLSIHFSPFPIFILLSL
CSDV       ------------------------------------------------------------
           241                                                        300

GFkV       LLLLQFPRT
CSDV       ---------
```

Figure 3

Agarose gel electrophoresis of DNA fragments amplified with primers based on the CSDV nucleic acid sequences M a b c d e f g h i j k l m n o p q r s t u v x z RNA gel blot analysis of RNA samples from CSD-symptomatic and -asymptomatic plants

Figure 5

Agarose gel electrophoresis of PCR products of a DNA fragment amplified with primers based on the CSDV nucleic acid sequences 1 2 3 4 5 6 7 8    9 10 11 12 13 14  15 16 17 18 19 20 21 22

Figure 6

Western blot detection of the CSDV Coat Proteins in the crude protein extracts of CSD-affected and unaffected citrus trees

Figure 7

Electron microscopy of CSDV purified from infected citrus tissues

Figure 8

Northern blot hybridization of total nucleic acids extracted from purified CSDV preparation gRNA → — 7.46 kb sgRNA → — 1.35 kb Drawing of TDNA insert fragment correspondent to pTYMO-AS vector

ISOLATED NUCLEIC ACID MOLECULES FROM THE GENOME OF CITRUS SUDDEN DEATH VIRUS AND USES THEREOF

RELATED APPLICATIONS

This application claims priority of PCT International Application PCT/BR2004/000179, filed Sep. 20, 2004, which designated the United States, and is a continuation in part of provisional application Ser. No. 60/506,520, filed Sep. 26, 2003, provisional application Ser. No. 60/508,979, filed Oct. 6, 2003, provisional application Ser. No. 60/529,246, filed Dec. 12, 2003, and provisional application Ser. No. 60/560,466, filed Apr. 7, 2004, all of which are incorporated by reference in their entirety.

SEQUENCE LISTING

The instant application contains a Sequence Listing which has been submitted in ASCII format via EFS-Web and is hereby incorporated by reference in its entirety. Said ASCII copy, created on May 4, 2011, is named 05999401.txt and is 93,350 bytes in size.

FIELD OF THE INVENTION

The invention relates generally to the fields of molecular biology, biochemistry, plant pathology, and agriculture. More particularly, the invention relates to polynucleotides and proteins from a phytopathogenic virus, suitable for disease diagnosis and generation of transgenic plants with resistance to infectious viruses strains.

BACKGROUND OF THE INVENTION

Several Citrus diseases have been shown to be caused by infection with pathogenic viruses (Derrick, K. S. and Timmer, L. W., *Annu. Rev. Phytopathol.*, 38. 181-205 (2000)). One of the most important of these viruses is Citrus Tristeza Virus (CTV), a member of the Closterovirus group which induces serious disease syndromes in citrus. For example, CTV induces quick decline that causes the death of trees grafted on sour orange rootstock, and stem pitting of scion cultivars regardless of the rootstock used (Bar-Joseph et al., *Annu. Rev. Phytopathol.*, 27. 291-316 (1989)). These diseases cause significant losses in the citrus industry worldwide.

In Brazil, citrus tristeza, first detected in 1937, destroyed millions of trees of sweet orange grafted on sour orange rootstocks. The problem was solved by exchanging sour orange rootstock with Rangpur lime rootstock. Today, more than 85% of the 200 million citrus trees in Brazil are grafted on Rangpur lime rootstock (Gimenes-Fernandes, N. and Bassanezi, R. B., *Summa Phytopathologica.*, 27. 93 (2001)).

In 1999, a new citrus disease, named Citrus Sudden Death (CSD) was discovered in Brazil (Gimenes-Fernandes, N. and Bassanezi, R. B. *Summa Phytopathologica.*, 27. 93 (2001)). This disease affects sweet orange (*Citrus sinensis*) grafted on Rangpur lime rootstock (*Citrus limonia*), and causes the death of trees within a few months after the symptoms manifest (Gimenes-Fernandes, N. and Bassanezi, R. B. *Summa Phytopathologca.*, 27. 93 (2001)). Although the disease was first observed in the sweet orange/Rangpur lime scion/rootstock combination, it has also been observed in orange trees cvs. Hamlin, Natal, Valencia, Pera, and Rubi, all grafted onto Rangpur lime (Bassanezi et al., *Phytopathol.*, 93. 4. 502-512 (2003)).

Plants with CSD symptoms present generalized leaf discoloration, partial defoliation, decreased number of young shoots and absence of internal shoots (Bassanezi et al., *Phytopathol.*, 93. 4. 502-512 (2003)). As the symptoms become more pronounced, the disease progresses rapidly and leads ultimately, to the death of the plant. The physiological status of the plant is important for the disease progression, since the severity of the symptoms increase at high water demand (Gimenes-Fernandes, N. and Bassanezi, R. B. *Summa Phytopathologica.*, 27. 93 (2001)). The root system of the symptomatic plants is severely damaged and dies quickly as the disease progresses. CSD is also characterized by the development of a strong yellow stain in the phloem of the Rangpur lime rootstock (Gimenes-Fernandes, N. and Bassanezi, R. B. *Summa Phytopathologica.*, 27. 93 (2001)). The time between the appearance of the first visible symptoms in the canopy and the death of the plant ranges from 1 to more than 12 months depending on season and citrus variety (Bassanezi et al., *Phytopathol.*, 93. 4. 502-512 (2003)).

The number of symptomatic trees in one affected area (north of São Paulo State and south of Triângulo Mineiro region, west of Minas Gerais State, Brazil), where the disease was originally found, increased from 500 in 1999 to more than 300,000 in February, 2002, and more than 1 million in June 2003 (Bassanezi, et al., *Phytopathol.*, 93. 4. 502-512 (2003)); (Román et al., *Plant Disease*, 88. 5. 453-467 (2004)). The pattern of CSD dissemination is similar to that of quick-decline, a disease caused by certain CTV isolates that elicit a graft union incompatibility when infected sweet orange scions are grafted onto sour orange rootstocks (Bassanezi et al., supra) however, CSD affects several sweet oranges grafted on Rangpur lime, a rootstock/scion combination that is not affected by the CTV strains that causes quick-decline (Bassanezi et al., supra).

Based on the spatial and temporal patterns of CSD dissemination, it has been hypothesized that CSD may be caused by an insect-vectored pathogen, potentially a new, undescribed strain of CTV (Bassanezi et al., supra.) Alternatively, a new virus could be the causative agent of the CSD disease.

To test if CSD is caused by a variant strain of CTV or is caused by a new virus, a genomic approach using shotgun sequencing of genomic viral RNA that had been randomly reverse transcribed and cloned in a plasmid vector, was used to study the disease described herein. Bioinformatic tools were developed for the identification and assembly of viral sequences. Using this approach, it was possible to obtain a saturated database of viral sequences from individual trees.

Genomic viral RNA isolated from citrus trees symptomatic or asymptomatic for CSD were reverse transcribed and the first strand cDNA was used to construct random-primed cDNA libraries. Around 2,000 cDNA clones from each tree were sequenced and the sequences were analyzed using BLASTX, BLASTN, and TBLASTX searches against public databases. A viral genome assembled consensus sequence of 6820 nucleotides (SEQ ID NO: 1) encoding a viral polyprotein (SEQ ID NO: 2) sufficient to assemble a viral particle, was identified.

The 6820 nucleotides viral genome sequence, when translated in all possible frames, give rise to, at least, the following polypeptides: a Major Capsid Protein (Coat Protein 1) encoded by the Nucleotide Sequence Domain (NSD1) starting at nucleotide position 6028 and ending at nucleotide position 6675 of SEQ ID NO: 1, whose translation product give rise to the Amino Acid Sequence Domain (AASD) of the polypeptide of SEQ ID NO: 2, starting, at amino acid position 1974 and ending at amino acid position 2188; a Minor Capsid Protein (Coat Protein 2) encoded by NSD2 of SEQ ID NO: 1 starting at nucleotide position 6082 and ending at nucleotide position 6675, whose translation product give rise to the AASD of the polypeptide of SEQ ID NO: 2, starting at amino acid position 1992 and ending at amino acid position 2188; a Putative Movement Protein encoded by NSD3 of SEQ ID NO: 1 starting at nucleotide position 6260 and ending at nucleotide position 6724, whose translation product give rise to the AASD of the polypeptide of SEQ ID NO: 3, starting at amino acid position 1 and ending at amino acid position 154; a Methyltransferase Domain encoded by NSD4 of SEQ ID NO: 1 starting at nucleotide position 487 and ending at nucleotide position 1119, whose translation product give rise to the AASD of the polypeptide of SEQ ID NO: 2, starting at amino acid position 127 and ending at amino acid position 337; a Protease Domain encoded by NSD5 of SEQ ID NO: 1 starting at nucleotide position 2797 and ending at nucleotide position 3114, whose translation product give rise to the AASD of the polypeptide of SEQ ID NO: 2, starting at amino acid position 897 and ending at amino acid position 1002; a Helicase Domain encoded by NSD6 of SEQ ID NO: 1 starting at nucleotide position 3358 and ending at nucleotide position 4053, whose translation product give rise to the AASD of the polypeptide of SEQ ID NO: 2, starting at amino acid position 1084 and ending at amino acid position 1315; a RNA-dependent RNA polymerase encoded by NSD7 of SEQ ID NO: 1 starting at nucleotide position 4528 and ending at nucleotide position 5778, whose translation product give rise to the AASD of the polypeptide of SEQ ID NO: 2, starting at amino acid position 1474 and ending at amino acid position 1890.

The viral genome sequence showed strong similarity to several viruses from the Tymoviridae family of plant viruses, especially the oat blue dwarf virus (FIGS. 1 and 2). Analysis of CSD-symptomatic or asymptomatic trees for the presence of these viral sequences revealed that only trees presenting the CSD symptoms contain the viral sequences. It was therefore assumed that these sequences belong to an undescribed virus of the Tymoviridae family which is the causative agent of the CSD disease.

SUMMARY OF THE INVENTION

The present invention relates to nucleic acid molecules of and from the genome of a virus that is the causative agent of CSD disease. Sequence comparison with a number of viral genome sequences revealed that this new virus belongs to the Tymoviridae family. This new virus is herein named "Citrus Sudden Death Virus," or "CSDV". It is hereafter an object of the invention to provide nucleic acid molecules which encode infectious CSDV. Such nucleic acid molecule is referred to throughout the application as "CSDV nucleic acid molecules".

For the purposes of this application, nucleic acid molecules refers to RNA, DNA, cDNA or any variant thereof with functions equivalent to RNA, gDNA, and cDNA, such as the synthesis of CSDV polypeptide domains. Also, the polypeptide domains encoded by CSDV nucleic acid molecules are referred to throughout the application as "CSDV polypeptides" or "CSDV proteins".

The invention relates to the use of the CSDV nucleic acid molecules to produce polypeptides. "Nucleic acid molecules of the invention" refers to, e.g., CSDV nucleic acid molecules, mutations of CSDV nucleic acid molecules, chimeric nucleic acid molecules and so forth.

In one embodiment, polypeptides are produced by cells transfected with nucleic acid molecules of the invention. In another embodiment, the polypeptide or polypeptides are produced recombinantly from a fragment or portion of the nucleic acid molecules of the invention. In yet another embodiment, the polypeptides are chemically synthesized.

Since, in nature, the CSDV proteins are ultimately synthesized from the information contained in the genome sequence of CSDV, the invention also relates to the use of the CSDV particles isolated and purified from infected plants tissues and/or organs. In one embodiment the particles can be used to produce antibodies against the CSDV proteins. In another embodiment the purified CSDV particles can be used to isolate and purify CSDV protein domains that can further be used to produce antibodies against CSDV.

The polypeptides of the invention can serve, e.g., as immunogens in the development of diagnostic assays for detecting the presence of CSDV in biological samples, as they provoke antibody production, and the antibodies can then be used in assays.

The invention also relates to the use of the CSDV nucleic acid molecules for diagnosis purposes, in which oligonucleotide primers containing from 5 to 100 nucleotides presenting from 90 to 100% identity with the CSDV nucleotide sequences can be used in, e.g., RT-PCR reactions, so that parts of the CSDV nucleic acid molecules can be amplified and detected in ordinary agarose gels serving as a diagnostic for the presence of the virus.

The invention also relates to methods of transforming plants, such as monocots or dicots, with constructs containing the CSDV nucleic acid molecules, to produce plants that are resistant to CSDV. Such methods include the introduction of constructs containing at least one CSDV nucleic acid molecule into plant parts, such as scions, rootstock cultivars, and so forth, as well as into citrus germplasm and breeding lines. Transformed CSDV-resistant germplasm and breeding lines can be used in conventional breeding programs, to create new cultivars that carry and express the resistance genes.

Accordingly, the invention features (i) isolated and/or purified CSDV nucleic acid molecules that have at least 65% sequence identity with the nucleotide sequence of SEQ ID NO.: 1; (ii) sequences complementary thereto or nucleotides whose complement hybridizes under high stringency conditions to the nucleotide sequence of SEQ ID NO.: 1; as well as with the coding regions of the domains encoded therein (iii) polypeptides or portions of polypeptides that have at least 70%, more preferably 80% sequence identity with the amino acid sequence of SEQ ID NO.: 2, or with any of the domains within SEQ ID NO:2 as defined herein.

"Stringent conditions" as used herein, refers to parameters with which the art is familiar, i.e., hybridization in 3.5×SSC, 1×Denhardt's solution, 25 mM sodium phosphate buffer (pH 7.0), 0.5% SDS, and 2 mM EDTA for 18 hours at 65° C., followed by 4 washes of the filter at 65° C. for 20 minutes, in 2×SSC, 0.1% SDS, and a final wash for up to 20 minutes in 0.5×SSC, 0.1% SDS, or 0.3×SSC and 0.1% SDS for greater stringency, and 0.1×SSC, 0.1% SDS for even greater stringency. Other conditions may be substituted, as long as the degree of stringency in equal to that provided herein, using a 0.5×SSC final wash.

The invention also features expression vectors or constructs in which the CSDV nucleic acid molecules are operably linked to one or more expression control sequences or promoters.

The invention further features a transgenic plant, such as one of the genera *Citrus* and *Poncirus*, into which a CSDV nucleic acid molecule has been introduced. Exemplary are citrus scions and rootstock cultivars (e.g., from sour orange [*Citrus aurantium*], Rangpur lime [*Citrus limonia*], rough lemon [*Citrus limonia* and *Citrus jambhin*], mandarin "Cleopatra" [*Citrus reshni*], Sunki [*Citrus sunki*], Volkamerian lemon [*Citrus volkameriana*], "Caipira" orange [*Citrus sinensis*]) and intrageneric hybrids (e.g., tangelos [*Citrus paradisi*×*Citrus reticulate*], tangors [*Citrus reticulate*×*Citrus sinensis*], citrumelo [*Poncirus trifoliata*×*Citrus maxima*], and citrange [*Citrus sinensis*×*Poncirus trifoliate*]). The plant can be a breeding line. It can also be one from *Fortunella* and *Citrofortunella* species, including calamondin and kumquat. The nucleic acid molecule in the plant preferably includes a selectable marker such as an herbicide resistance gene.

The invention relates to nucleic acid molecules, and the polypeptides they encode, which were identified using shotgun sequencing of viruses genomes from citrus plants with or without symptoms of CSD. These sequences come from a newly identified virus of the Tymoviridae family which, when it infects a plant, such as a citrus plant, causes CSD disease, leading to the death of the plant. Methods of genetic transformation to produce plants that are resistant to CSDV strains are within the invention. Such methods include the introduction of constructs containing the CSDV nucleic acid molecules into scions and/or rootstocks, so that commercial varieties or any other germplasm useful for breeding programs can be produced and used to create new cultivars resistant to CSDV.

Accordingly, the invention involves purified CSDV nucleic acid molecules, which may be isolated from citrus plants manifesting symptoms of CSD, that when used in appropriate constructs have the ability to confer resistance to pathologies caused by CSDV infection in plants infected with CSDV. The nucleic acid molecule can be a purified portion or a gene present in the complete genome of CSDV, e.g., a nucleic acid molecule whose nucleotide sequence encodes a polypeptide or a portion of a polypeptide that has at least 80% sequence identity to the amino acid sequence of SEQ ID NO.: 2. The nucleotide sequences can be that of SEQ ID NO.: 1 or one that define polynucleotides whose complement hybridizes under high stringency conditions to the nucleotide sequences of SEQ ID NO.: 1.

The invention also features expression vectors, isolated recombinant cells, and plants and plant parts containing the nucleic acid molecule of the invention, e.g., one of the nucleic acid molecules described above. The nucleic acid molecule in the vector, cell, seed or plant can be operably linked to one or more expression control sequences or promoters.

In addition, the invention features the purified proteins encoded by the nucleic acid sequence domains present in the genome sequence of CSDV. The proteins include those with amino acid sequences that (a) share at least 80% sequence identity with SEQ ID NO.: 2 or (b) includes the amino acid sequences of SEQ ID NO.: 2. Proteins of the invention can be expressed in bacteria either as "neat" proteins, or as heterologous or fusion polypeptides. The invention also features antibodies raised against the proteins of the invention, e.g., those described above. The antibodies can further include a detectable label.

The invention also features a plant transfected with one of the nucleic acid molecules of the invention, e.g., any purified CSDV sequence. The plant may be of the genera *Citrus* and *Poncirus* (e.g., sweet orange [*Citris sinensis*], mandarin [*Citrus reticulata*], sour orange [*Citrus aurantium*], Rangpur lime [*Citrus limonia*], rough lemon [*Citrus limonia* and *Citrus jambhin*], mandarin "Cleopatra" [*Citrus reshni*], Sunki [*Citrus sunki*], Volkamerian lemon [*Citrus volkameriana*], "Caipira" orange [*Citrus sinensis*]) and intrageneric hybrids (e.g., tangelos [*Citrus paradisi*×*Citrus reticulata*], tangors [*Citrus reticulate*×*Citrus sinensis*], citrumelo [*Poncirus trifoliata*×*Citrus maxima*], and citrange [*Citrus sinensis*×*Poncirus trifoliate*]). The plant can be a breeding line. It can also be one from *Fortunella* and *Citrofortunella* species, including calamondin and kumquat.

The invention features a method of producing a disease resistant plant by introducing constructs containing purified nucleic molecules under the control of a suitable plant promoter, into the plant, transforming the plant with *Agrobacterium* strains or microprojectile bombardment.

All technical terms used herein are terms commonly used in biochemistry, molecular biology, phytopathology and agriculture, and will be understood by one of ordinary skill in the art to which this invention belongs. Those technical terms can be found in, e.g., Molecular Cloning: A Laboratory Manual, 3rd ed., vol. 1-3, ed. Sambrook and Russel, Cold Spring Harbor Laboratory Press, Cold Spring Harbor, N.Y., 2001; Current Protocols in Molecular Biology, ed. Ausubel et al., Greene Publishing Associates and Wiley-Interscience, New York, 1988 (with periodic updates); Short Protocols in Molecular Biology: A Compendium of Methods from Current Protocols in Molecular Biology, $5^{th}$ ed., vol. 1-2, ed. Ausubel et al., John Wiley & Sons, Inc., 2002; Genome Analysis: A Laboratory Manual, vol. 1-2, ed. Green et al., Cold Spring Harbor Laboratory Press, Cold Spring Harbor, N.Y., 1997. Methods involving plant biology techniques are described herein and are described in detail in methodology treatises such as Methods in Plant Molecular Biology: A Laboratory Course Manual, ed. Maliga et al., Cold Spring Harbor Laboratory Press, Cold Spring Harbor, N.Y., 1995. Various techniques using PCR are described, e.g., in Innis et al., PCR Protocols: A Guide to Methods and Applications, Academic Press, San Diego, 1990 and in Dieffenbach and Dveksler, PCR Primer: A Laboratory Manual, $2^{nd}$ ed., Cold Spring Harbor Laboratory Press, Cold Spring Harbor, N.Y., 2003. PCR-primer pairs can be derived from known sequences by known techniques such as using computer programs intended for that purpose (e.g., Primer, Version 0.5, 1991, Whitehead Institute for Biomedical Research, Cambridge, Mass.). Methods for chemical synthesis of nucleic acids are discussed, for example, in Beaucage and Caruthers (1981) *Tetra. Letts.*, 22:1859-1862 and Matteucci and Caruthers (1981) *J. Am. Chem. Soc.*, 103:3185.

BRIEF DESCRIPTION OF THE DRAWINGS

The invention can be more readily understood by reference to the accompanying drawings, wherein:

FIG. 1 shows the alignment of the nucleotide sequence of the CSDV genome (SEQ ID NO: 1) with that of the Tymoviridae Oat Blue Dwarf Virus/OBDV-GI 9629255 (SEQ ID NO: 13).

FIG. 2 shows the alignments of the amino acid sequence of the polyprotein encoded by the CSDV genome (SEQ ID NO: 2) with those encoded by other Tymoviridae genomes [Oat Blue Dwarf Virus/OBDV—GI 9629255 (SEQ ID NO: 14), Grapevine Fleck Virus/GFkV—GI 18138525 (SEQ ID NO: 19), Grapevine Asteroid Mosaic-Associated Virus/GAMaV—GI 29335718 (SEQ ID NO: 15)]. FIG. 2 (b) discloses SEQ ID NOs: 15-16, respectively, in order of appearance. FIG. 2 (c) discloses SEQ ID NOs: 17-18, respectively, in order of appearance. FIG. 2 (d) discloses SEQ ID NOs: 19 and 3, respectively, in order of appearance.

FIG. 3 shows the PCR amplification of a DNA fragment amplified with primers based on the CSDV nucleotide sequence of SEQ ID NO.: 1. CDNA samples were prepared from symptomatic and asymptomatic citrus trees. Only trees presenting the CSD symptoms contain an amplifiable CSDV sequence of SEQ ID NO.: 1.

FIG. 5 depicts the results of a RT-PCR experiment performed on total RNA taken from insect bodies, to determine the vectors that transmit CSD.

FIG. 6 shows the results of a western blot experiment in which total protein extract from symptomatic and asymptomatic plants where subject to a protein gel blot analysis developed with antibody against the CSDV Coat Proteins 1 and 2, respectively.

FIG. 7 shows an electron micrography of virus particles purified from citrus plants presenting CSD symptoms.

FIG. 8 shows a Northern blot of RNA extract from purified virus particle.

DETAILED DESCRIPTION OF THE INVENTION

Figure 4:
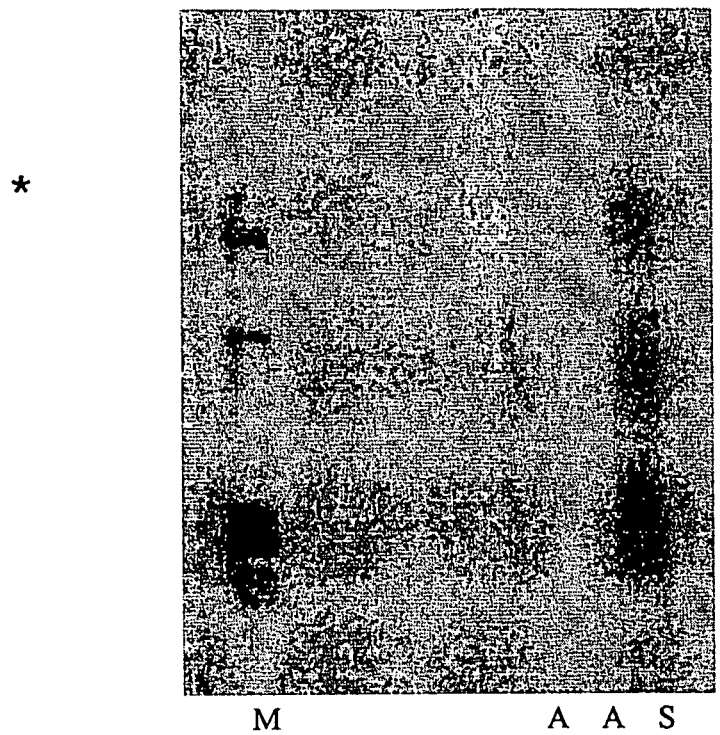
FIG. 4 shows the results of a Northern Blot experiment in which RNA samples from symptomatic and asymptomatic plants were subjected to an RNA gel blot analysis to verify the presence of RNA species able to hybridize with a DNA probe derived from the CSDV sequences. Only lanes containing RNA samples from symptomatic trees possess a band sizing 6.5 kbp representing the complete CSDV viral RNA genome.
Figure 9:
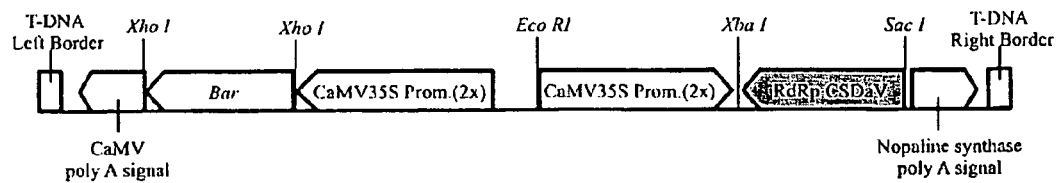
FIG. 9 shows a drawing of the vector pTYMO-AS that contain part of the RNA-dependent RNA polymerase sequence domain (SD7, as defined in SEQ NO.: 1) operably linked to the CaMV 35S promoter. This vector was used to transform citrus plants by *Agrobacterium* mediated transformation.

Nucleic acid molecules from the genome of an undescribed virus that causes Citrus Sudden Death (CSD) have been cloned and sequenced. Such nucleic acid molecules are referred to throughout the application as "CSDV nucleic acid molecules". Polypeptides predicted from CSDV nucleic acid molecules have been analyzed using software programs including BLAST, and have been shown to encode, inter alia, an RNA polymerase, a methyltransferase, a protease and a helicase that are involved in the replication of the CSDV, a movement protein involved in the translocation of the virus throughout the plant, and the capsid proteins responsible for the encapsulation of the virus genome.

The molecular cloning of CSDV nucleic acid molecules provides the means to develop diagnostic methods to detect the presence of CSDV in biological samples, including tissues, cells and organs of plants, such as plants of the genus *Citrus*. The molecular cloning of CSDV nucleic acid molecules also provides the means to create CSD-resistant plants of the genus *Citrus* through genetic transformation. Genetic transformation of plants of the genus *Citrus*, can be obtained using *Agrobacterium* mediated transformation methods. Such methods include cloning constructs containing CSDV nucleic acid molecules operably ligated to promoter and enhancer regions, initiation and termination sequences. These constructs can also contain genes for selectable markers, such as herbicide resistance. These constructs may be cloned in the Ti plasmid of *Agrobacterium*. Plasmid vector-containing constructs are used to transform commonly used *Agrobacterium* strains, which are subsequently used to transform plants, such as those of the genus *Citrus*. Plasmid vector-containing constructs may be also introduced into plants by microprojectile bombardment. The constructs containing the CSDV nucleic acid molecules are useful for creating CSD resistant plants such as all common types of citrus fruits, including but not limited to sweet oranges, grapefruit, mandarins, tangerines, pummelos, lemons, limes, citrons, bergamots, limequats, meyer lemons, silver limes, key limes, kaffir limes, lavender gems, blood oranges, satsumas, oroblancos, melogolds, bergamots, intrageneric hybrids such as tangelos and tangors, and citrus-type fruit such as calamondins and kumquats (*Fortunella* spp.). For example, CSDV nucleic acid molecules can be introduced into commercially utilized rootstock cultivars, including but not been limited to, Rangpur lime, sour orange, rough lemon, various mandarins, and citrus intrageneric and intergeneric hybrids. CSD resistant citrus plants, composed of genetic modified scions and rootstocks, can then be used by citrus growers to counter CSD disease, and to avoid decreased productivity and/or tree death and replanting costs.

The invention provides purified nucleic acid molecules (polynucleotides) that encode polypeptides having an amino acid sequence such as that of SEQ ID NO.: 2.

The CSDV nucleic acid molecules of the present invention can be obtained from CSDV infected plants. The molecules of the present invention may be in the form of RNA or in the form of cDNA. The cDNA may be double- or single-stranded, and, if single-stranded may be the coding (sense) strand or noncoding (anti-sense) strand. The sequence may be identical to a nucleotide sequence of SEQ ID NO.: 1. It may also be a different coding sequence which, as a result of the redundancy or degeneracy of the genetic code, encodes the same polypeptide as polynucleotides of SEQ ID NO.: 1. Other nucleic acid molecules within the invention are variants of CSDV nucleic acid molecules such as those that encode fragments, analogs and derivatives of native CSDV nucleic acid molecules. Such variants may be, e.g., naturally occurring polymorphic variants of native CSDV nucleic acid molecules, or a non-naturally occurring variant of native CSDV nucleic acid molecules. For example, the nucleotide sequence of such variants can feature a deletion, addition, or substitution of one or more nucleotides of native CSDV nucleic acid molecules. Naturally occurring variants of native CSDV nucleic acid molecules within the invention are nucleic acids isolated from CSDV infected plants that have at least 65% sequence identity with native CSDV nucleic acid molecules, and encode polypeptides having at least one functional activity in common with native CSDV nucleic acid molecules encoded proteins.

Shorter oligonucleotides (e.g., those from 6-200, preferably 12-200, more preferably 20, 30, or 50 to 200 (100, 125, 150 or 200) base pairs in length), e.g., that match perfectly to the CSDV nucleic acid molecules or hybridize with CSDV nucleic acid molecules at stringent conditions as defined herein can be used as probes, primers, or antisense molecules.

Longer polynucleotides (e.g., those of 300 to 800 base pairs) that encode or hybridize with CSDV nucleic acid molecules, can be used in place of a native CSDV nucleic acid molecule in applications where it is desired to modulate the functional activity of a native CSDV nucleic acid molecule.

Nucleic acids molecules that hybridize under stringent conditions as defined herein to CSDV nucleic acid molecules of SEQ ID NO.: 1 or the complement of the SEQ ID NO.: 1 are also within the invention. For example, such nucleic acids can be those that hybridize with the CSDV nucleic acid molecules of SEQ ID NO.: 1 or the complement of the SEQ ID NO.: 1, under low stringency conditions, moderate stringency conditions, or high stringency conditions, and are within the scope of the invention. Preferred nucleic acids molecules are those having a nucleotide sequence that is the complement of all or a portion of the CSDV nucleic acid molecules of SEQ ID NO.: 1. Other variants of nucleic acid molecules within the invention are polynucleotides that share at least 65% sequence identity to the CSDV nucleic acid molecules of SEQ ID NO.: 1 or the complement of SEQ ID NO.: 1.

Other CSDV nucleic acid molecules encoding polypeptides are also within the invention. Such polypeptides can be made by preparing a construct (e.g., an expression vector) that expresses CSDV nucleic acid molecules encoding polypeptides, when introduced into a suitable host. Variant CSDV nucleic acid molecule-encoding polypeptides can be produced by those skilled in molecular biology procedures using standard nucleic acid mutagenesis techniques or chemical synthesis, or the polypeptides can be isolated and purified from CSDV particles isolated and purified from infected plants, as the CSDV particles encoded by nucleic acid molecules of SEQ ID NO.: 1 and polypeptide domains of SEQ ID NO.: 2. Antibodies can be produced against the isolated and purified CSDV particles and can be used for serological diagnosis of the virus.

Another aspect of the invention relates to the use of purified antisense nucleic acids to inhibit expression of CSDV nucleic acid molecules. Antisense nucleic acid molecules within the invention are those that specifically hybridize under cellular conditions to cellular mRNA and/or genomic RNA of CSDV in a manner that inhibits expression of the nucleic acid domains encoded by the CSDV nucleic acid molecules.

The antisense nucleic acid molecules can be delivered into cells that express CSDV genes. For instance, constructs expressing antisense molecules under the control of a strong promoter can be introduced into citrus plants by genetic transformation using *Agrobacterium* or microprojectile bombardment (Ghorbel et al. *Tree Physiology.*, 20. 1183-1189 (2000); Bespalhok et al., *Crop Breed. Appl. Biotech.*, 1. 27-34 (2001); Bespalhok et al., *Braz. Arch. Biol. Technol.*, 46. 1. 1-6 (2003); Molinari et al., *Scientia Horticulturae.*, 99. 34. 379-385 (2004); Jia-Long et al., *Plant Science*, 113. 2. 175-183 (1996)).

The expression of CSDV nucleic acid molecules can be modulated by RNA interference (RNAi) (Lee et al. *Nature Biotech.*, 19. 500-505 (2002); Voinnet, O. *Trends Genet.*, 17. 449-459 (2001)) by which a construct driving the synthesis of sequence-specific double-stranded RNA (dsRNA) is introduced into an organism or cell in order to silence the targeted gene (Hannon, *Nature*, 418. 244-251 (2002)). Selected sequences corresponding to CSDV nucleic acid molecules can be used to create, after expression, a sequence-specific dsRNA that can interfere with accumulation of endogenous RNA encoded by the CSDV nucleic acid molecules.

The CSDV nucleic acid molecule can be altered by using molecular biology techniques to produce a mutant recombinant virus that work as a vaccine. This is well known in the art as cross-protection system, in which a mild, non-infective virus is introduced in a plant and after replication induces in the host plant a defense response against the severe, infective strain (Costa, A. S. and Muller, G. W. 1980, *Plant Dis.*, 64:538-541). Plants inoculated with recombinant CSDV mutant become resistant to the wild-type CSDV infective strains.

The present invention is further illustrated by the following specific examples. The examples are provided for illustration only and are not to be construed as limiting the scope or content of the invention in any way.

EXAMPLES

Example 1

This example describes the identification and cloning of nucleic acid molecules corresponding to the complete genome sequence of CDSV. cDNA libraries were constructed from double strand RNA isolated from citrus plants presenting symptoms of CSD by shotgun cloning of cDNAs generated by RT-PCR. Clones were randomly sequenced using an ABI 3700 sequencer. Sequences were trimmed for vector bases and low quality bases and BLASTX-analyzed against the non-redundant (NR) GenBank database. Two cDNA clones were identified as having nucleotide sequences similar to viral nucleotide sequences of the Tymoviridae family. By primer walking PCR using a cDNA library or total RNA from CSD plants as templates, cDNA clones were identified that, after sequencing on both ends, gave rise to a consensus CSDV nucleic acid sequence of 6820 nucleotides. This consensus sequence contains nucleotide sequence domains that encode the complete set of the viral proteins comprised of: a Major Capsid Protein (Coat Protein 1), a Minor Capsid Protein (Coat Protein 2), a Putative Movement Protein, a Methyltransferase Domain, a Protease Domain, a Helicase Domain and a RNA-dependent RNA polymerase. The gene and protein domains organization of CSDV is similar to that found in several virus strains of the Tymoviridae family, especially to the Oat blue dwarf virus (FIGS. 1 and 2).

Example 2

This example describes RT-PCR analysis of citrus plants to determine if the CSDV nucleic acid molecules of the invention could be used to design oligonucleotide primers that amplify CSDV sequences and could be use in diagnostic assays. Oligonucleotide primers designed on the basis of CSDV nucleic acid molecules of SEQ ID NO.: 1 were used to amplify the CSDV nucleic acid sequences using RT-PCR from RNA isolated from CSD symptomatic or asymptomatic citrus plants. Bark from young citrus branches was peeled and ground to a powder, in liquid nitrogen. Total RNA was purified from 100 mg of bark tissue by using Trizol reagent according to the manufacturer's instructions. The resulting total RNA was suspended in 50 ul of DEPC (diethylpyrocarbonate)-treated sterile water and used for cDNA synthesis. First strand cDNA was synthesized using 8 ul of total RNA (approx. 8 ug) as template. Two microliters of random primers (1 ug) were added to the total RNA that had been denatured at 97° C. for 5 min. The solution was then incubated on ice while adding 1 ul of 10 mM dNTP mix and 3 ul of First Strand buffer (250 mM Tris-HCl, pH 8.3, 375 mM KCl, 15 mM $MgCl_2$) to the tube. The mixture was incubated at room temperature for 2 min, 1 ul (200 U) of the enzyme reverse transcriptase SuperScript II was added and the solution was further incubated at room temperature for 10 min. followed by 60 min. at 42° C. For PCR, 1 ul of the synthesized cDNA was added to a 20 ul reaction containing 0.5 mM of each of primers "TYMOF2" 5'-GTCAGCTGTCCAACCAGTTCC-3' (SEQ ID NO: 4) and "TYMORR": 5'-GTGAAGATCAAT-GAGAGCCTG-3'(SEQ ID NO: 5), 0.125 mM each dNTP, 2.5 mM $MgCl_2$, 1× reaction buffer (20 Mm Tris-HCl, pH 8.4, 50 mM KCl), and 1 U of Taq polymerase. The reaction was heated for 2 min. at 94° C. and subjected to 40 amplification cycles (30 s at 94° C., 30 s at 55° C., 1 min at 72° C.). Ten microliters of the RT-PCR reaction were combined with 10 ul of 2× digestion buffer (100 mM potassium acetate, 40 mM Tris-acetate, 20 mM magnesium acetate, 2 mM DTT and 4 ug BSA, pH 7.9) and 0.5 ul of the restriction enzyme ApaI (5 U). Digestion was carried out for 2 hours at 25° C. DNA fragments were separated in a 1.5% agarose gel, stained with 100 ng/ml ethidium bromide and compared under UV light.

The results are depicted in FIG. 3. Lanes a-f and m-t are from asymptomatic plants, while g to l, and u to z are from symptomatic plants. There is no banding at all in lanes a-f and m-t, while clear banding is evident in the samples from symptomatic plants in lanes g to l and u to z, which generate fragments of 500 and 250 base pairs long when digested with ApaI enzyme. Data was further expanded to 512 plants (351 symptomatic and 161 asymptomatic) and 99.7% of yellow bark plants shows the CSDV nucleic acid fragment amplification.

Example 3

In these experiments, Northern blotting was carried out on samples of RNA taken from asymptomatic and symptomatic plants. A DNA probe taken from CSDV nucleic acid molecules was used. FIG. 4 shows that a band of 6.5 kbp was identified in symptomatic plants, while no banding was identified in any of the asymptomatic material.

Total RNA from bark tissue of symptomatic and asymptomatic plants was extracted using the Trizol Reagent (Invitrogen) according to the manufacturer's protocol. Fifteen micrograms of total RNA from each sample were separated by denaturing electrophoresis on a 1% agarose gel containing 1×MOPS and 0.6M formaldehyde, according to Sambrook and Russell (Molecular Cloning: A Laboratory Manual, 3rd ed., vol. 1-3, ed. Cold Spring Harbor Laboratory Press, Cold Spring Harbor, N.Y., 2001). The gel was subsequently transferred to a Hybond-N+ nylon membrane (Amersham Pharmacia Biotech) by capillary transfer in 10×SSC (1×SSC is 0.15M NaCl; 0.015M sodium citrate) for 16 h. The membrane was baked at 80° C. for 2 h, prehybridized in ExpressHyb hybridization buffer (Clontech) for 2 h at 65° C., followed by hybridization in a fresh aliquot of ExpressHyb solution containing 20 ng/ml of probe ($2\times10^7$ cpm/ml) for 16 h at 65° C. The probe consisted of a 772-bp CSDV nucleic acid fragment amplified by PCR from a plasmid containing part of SEQ ID NO.: 1 using SEQ ID NOS: 4 and 5. The probe was radioactively labeled by random-priming with [α-32P]dCTP (6000 Ci/mmol) using the Random Primers DNA Labeling System (Invitrogen). After hybridization, the membrane was washed at room temperature in 2×SSC, 0.05% SDS for 4×10 min, and then twice at 55° C. for 20 min each in 0.1×SSC; 0.1% SDS. The blot was exposed for three days and analyzed by phosphoimaging on a FLA-3000 Fluorescent Image Analyzer (Fujifilm).

Example 4

This example describes RT-PCR analysis of citrus insect vectors to determine if the CSDV nucleic acid molecules of the invention could be found in insect vectors and therefore determine the kind and species of insects that could act as a vector for transmission and dissemination of CSD in citrus plantations.

A number of insect species including aphids such as *Toxoptera citricida, Aphis spiraecola* and *Aphis gossypii*, and leafhoppers/planthoppers representing, but not limited to, *Deois flavopicta, Xerophloa viridis, Ferrariana trivittata, Hortensia similis, Erytrogonia sexguttata, Macugonalia leucomelas, Dechacona missionum*, and *Copididonus hialipennis* were sampled at citrus plantation areas affected by CSD and at areas without symptoms of CSD. In the areas affected by CSD the insects were collected from individual trees presenting symptoms of CSD. Leafhoppers/planthoppers were separated into 6 groups according to morphological characteristics, while aphids were separated according the respective species. Around fifty individuals of each leafhoppers/planthoppers group or aphids species were used to extract total RNA.

Total RNA from whole bodies of insects was extracted using the Trizol Reagent (Invitrogen) according to the manufacturer's protocol. Eight micrograms of total RNA from each sample were used for RT-PCR analysis using CSDV specific primers designed on the basis of the CSDV nucleic acid molecules of SEQ ID NO: 1.

RT-PCR was carried out on samples of total RNA using SEQ ID NOS: 4 and 5. FIG. 5 shows that a band of 772 Kbp corresponding to part of the CSDV nucleic acid domain encoding the RNA-dependent RNA polymerase was amplified from samples taken from the aphids *Toxoptera citricida, Aphis spiraecola* and *Aphis gossypii* collected from symptomatic trees in the affected areas, while no band was amplified in any of the RNA samples isolated from leafhoppers or planthoppers of CSD affected areas, or from aphids collected in trees from the non-affected areas.

Table 1 presents a summary of the results of the assays for the presence of CSDV in samples of insects collected in CSD affected and non-affected areas. The virus was found only in the aphid samples from citrus trees of CSD affected areas. This suggests that these aphids could act as vectors for CSDV transmission and dissemination.

Example 5

This example illustrate the use of polyclonal antibodies raised against the CSDV Coat Proteins 1 and 2 to determine the presence of CSDV in plant extracts. The polyclonal antibodies was produced using two different sources of immunogens: 1) Peptides were designed based on the deduced amino acid sequences of Coat Proteins 1 and 2 of CSDV, taking into consideration b-turn structure prediction (Chou, P Y and Fasman, Biophys J., 1979 June; 26(3):367-73) and hydrophobicity level (Kyte, J. and Doolittle, R F, J Mol Biol., 1982 May 5; 157(1):105-32). Peptides corresponding to amino acids 7 to 20 (AGPAPSRDDRVDRQ (SEQ ID NO: 8)), 11 to 24 (PSRDDRVDRQPRLP (SEQ ID NO: 9)), 51 to 64 (DGSEAKNLSDDLSG (SEQ ID NO: 10)), 111 to 124 (PASASETSYYGGRL (SEQ ID NO: 11)), and 161 to 175 (RFSYSVYSNGGTKGT (SEQ ID NO: 12)) of the predicted Coat Protein 2 (amino acid positions 1974-2188 of SEQ ID NO: 2) were synthesized, KLH-conjugated (Genscript Corp, USA) and used to immunize rabbits. Polyclonal antibodies were delivered as antisera and used without further treatment for Western blot analyses. 2) Polyclonal antibodies were also obtained against the recombinant Coat Proteins 1 and 2. The CSDV nucleic acid sequences between nucleotide positions 6,028 to 6,672 (Coat Protein 1) and 6,082 to 6,672 (Coat Protein 2) were cloned into the pET-28a(+) expression vector (ClonTech) and expressed in *E. coli* BL21(DE3) strain. Coat Protein 1 was expressed as a fusion with a His-tag and thrombin site in the N-terminal (His-p22.5) and Coat Protein 2 was expressed fused to a His-tag in the C-terminal (p21-His) and also in a non-fused form (NFp21). Large scale expression was conduced under IPTG induction, bacterial cells were disrupted by French press, and the soluble fraction of the fused recombinant proteins were purified using the His-Trap purification Kit (Amersham). Purified p21-His and Hisp22.5 were used to raise polyclonal antibodies in rabbits.

Recombinant CSDV Coat Proteins and crude protein extracts from citrus trees were resolved in a 12% (w/v) acrylamide gel and proteins were transferred to nitrocellulose membrane by semi-dry electroblotting (BioRad apparatus). The membrane was blocked with a Blotto solution (PBS, pH 7.2 containing 0.1% Tween-20 and 5% (w/v) non-fat-milk powder), incubated with the polyclonal antibodies (1:1000 in PBS) against the peptides, washed with PBS-Tween 20 and incubated with anti-rabbit IgG alkaline phosphatase conjugate (BioRad, 1:2000 in PBS). Color development was carried out in freshly prepared substrate solution (1.5 mg NBT, 3 mg BCIP in 20 ml carbonate buffer, pH 9.2). Antisera obtained for the peptides were able to recognize both recombinant Coat Proteins as well as Coat Proteins present in the CSDV-infected plant extracts (FIG. 6). Two protein bands of expected size were evident only in infected plant extracts and may correspond to Coat Proteins 1 and 2, respectively. Similar results were obtained using antibody raised against the recombinant CSDV Coat Proteins.

Example 6

In this example, CSDV particles were purified from CSD-affected citrus plants according to the methodology described by Bar-Joseph et al. (Bar-Joseph, M., D. J. Gumpf, J. A. Dodds A. Rosner, and I. Ginsberg. 1985, *Phytopathology,* 75:195-198.). The purity of virus preparation was determined by electron microscopy using a negative staining methodology with 2% uranyl acetate (Gaméz, R., T. Fukuoka, and Y. Kozuka. 1977, *Rev. Biol. Trop.,* 25:151-157). The electron micrography shows purified virions as expected isometric, non-enveloped, ~30 nm in diameter particles, with a rounded contour, and prominent surface structure. As typical Tymovirus, CSDV present under uranyl acetate staining two types of particles (Boulila, M., D. Boscia, B. Di Terlizzi, M. A. Castellano, A. Minafra, V. Savino, and G. P. Martelli. 1990, *J. Phytopathol.,* 129:151-158), one with a negative stain (T form, represents non-infectious empty shells) and another with positive stain (B form, represents intact particles).

In order to confirm that the purified particles correspond to CSDV, total nucleic acids were purified from a preparation of virus particles by phenol extraction, resolved in a 1% agarose gel, transferred to Hybond-N+ nylon membranes (Amersham) and hybridized with a $P^{32}$-labelled DNA probe from part of the CSDV nucleic acid molecules of SEQ ID NO.: 1. The results of FIG. 8, confirm the presence of the CSDV genomic RNA in the purified sample.

Example 7

This is an example of a construct produced using a CSDV nuclei acid molecule in order to generate transgenic plant resistant to CSDV. A 761pb nucleic acid fragment of the CSDV RNA-dependent RNA Polymerase of SEQ ID NO.: 1, were PCR amplified using the primers TY-Fw (5'-TGGAGCTCCCTGCCCACGACCCAAC-3') (SEQ ID NO: 6), containing a Sac I restriction site and TY-Rv (5'-TCTAGAGCCTGGGGGATGGAGAGC-3') (SEQ ID NO: 7), containing a Xba I restriction site. This fragment was cloned in PGEM-T easy vector (Promega corp, Madison, Wis., USA) and confirmed by sequencing. The RNA-dependent RNA Polymerase fragment was removed from pGEM-T by restriction digestion with Xba I and Sac I and cloned in the antisense direction in pA35S(2×) (Kay, R., Chan, A., Daly, M. & McPherson, J., 1987, *Science,* 236: 1299-1302), restricted with the same enzymes yielding the plasmid pATYMO-AS. The pA35S(2×) plasmid includes a herbicide resistance gene (Christensen A H, Quail P H., 1996, Transgenic Res. 15: 213-218.) under the control of the CaMV35S promoter. FIG. 9 represents a drawing of the TDNA insertion fragment of pATYMO-AS.

In order to produce the transgenic citrus containing the plasmid pATYMO-AS, explants from 'in vitro' germinated *Rangpur lime* were used for transformation experiments with *Agrobacterium tumefaciens* strain EHA105 carrying the plasmid. The explants were inoculated with an overnight bacterial suspension for 20 min, blotted dry and platted onto MS medium containing 2,4D and acetoseringone. The co-cultivation was made in darkness for 3 days and then the explants were platted in MS medium containing BAP, PPT, cefotaxime and vancomycin. The developed shoots were transferred to MS medium containing IBA, PPT, cefotaxime and vancomycin. Transgenic regenerated plants were tested by PCR and Southern blot.

For the southern blot experiment genomic DNA from transgenic and non-transgenic plants were isolated according to Dellaporta et al. (Dellaporta S. L., Wood J., Hicks J. B, 1983, *Plant Mol. Biol. Rep.,* 1:19-21,). Purified DNA was digested with EcoRI, separated by agarose gel electrophoresis (10 ug DNA/lane, 1% agarose) then transferred onto charged nylon membranes according to standard procedures (Sambrook et al., 2001 Molecular Cloning: A Laboratory Manual, 3rd ed., vol. 1-3, ed. Cold Spring Harbor Laboratory Press, Cold Spring Harbor, N.Y.). Probes were labeled using the Genes Images™ AlkPhos Direct™ labelling and detection system from Amersham Biosciences that is based on a dioxetane chemiluminescence system. Blots were hybridized to CSDV specific probes and the citrus chalcone synthase CitCHS2 gene (GenBank 5106368) as a positive control. Membranes were washed at 55° C. according to the instruction manual (Genes Images AlkPhos Direct labeling and detection system—Amersham Biosciences). Chemiluminescent signals were detected using a CDP-Star™ chemiluminescent detection reagent (Amersham Biosciences) according to the protocol recommended.

TABLE 1

RESULTS OF TEST FOR THE PRESENCE OF CSDV IN INSECTS COLLECTED FROM *CITRUS* THREES IN CSD AFFECTED AND NON-AFFECTED AREAS.

| INSECT Leafhoppers/planthoppers | Samples Analyzed[a] | Diagnosis for CSDV |
|---|---|---|
| Group I | 1 (affected area) | Negative |
| | 2 (affected area) | Negative |
| Group II | 1 (affected area) | Negative |
| | 2 (affected area) | Negative |
| Group III | 1 (affected area) | Negative |
| | 2 (affected area) | Negative |
| Group IV | 1 (affected area) | Negative |
| Group V | 1 (affected area) | Negative |
| Group VI | 1 (affected area) | Negative |
| *T. citricida* | 1 (non-affected area) | Negative |
| | 2 (non-affected area) | Negative |
| | 3 (non-affected area) | Negative |
| | 4 (non-affected area) | Negative |
| | 5 (affected area) | Positive |
| | 6 (affected area) | Positive |
| | 7 (affected area) | Positive |
| | 8 (affected area) | Positive |
| | 9 (affected area) | Positive |
| | 10 (affected area) | Positive |
| | 11 (affected area) | Positive |
| | 12 (affected area) | Negative |
| | 13 (affected area) | Positive |
| | 14 (affected area) | Positive |
| | 15 (affected area) | Positive |
| *A. spiraecola* | 6 (non-affected area) | Negative |
| | 7 (affected area) | Positive |
| | 8 (affected area) | Positive |
| | 9 (affected area) | Negative |
| | 10 (affected area) | Negative |
| *A. gossypii* | 5 (non-affected area) | Negative |
| | 6 (non-affected area) | Negative |
| | 7 (affected area) | Positive |
| | 8 (affected area) | Negative |
| | 9 (affected area) | Negative |
| | 10 (affected area) | Negative |

[a]each sample was composed of >50 aphids or around 10 leafhoppers/planthoppers.

The invention claimed is:

1. A recombinant expression vector comprising a cDNA molecule comprising a nucleotide sequence encoding an amino acid sequence having amino acids 1974-2188 of SEQ ID NO: 2, operably linked to a heterologous promoter.

2. An isolated nucleic acid molecule of claim 1, wherein said nucleotide sequence further encodes amino acids 1992-2188 of SEQ ID NO: 2.

3. A recombinant expression vector of claim 1, wherein said nucleotide sequence further encodes amino acids 127-337 of SEQ ID NO: 2.

4. A recombinant expression vector of claim 1, wherein said nucleotide sequence further encodes amino acids 897-1002 of SEQ ID NO: 2.

5. A recombinant expression vector of claim 1, wherein said nucleotide sequence further encodes amino acids 1084-1315 of SEQ ID NO: 2.

6. A recombinant expression vector of claim 1, wherein said nucleotide sequence further encodes amino acids 1-154 of SEQ ID NO: 3.

7. A recombinant expression vector of claim 1, wherein said nucleotide sequence further encodes amino acids 1474-1890 of SEQ ID NO: 2.

8. A cDNA molecule comprising a nucleotide sequence consisting of nucleotides 6028-6675 of SEQ ID NO: 1, operably linked to a heterologous promoter.

* * * * *

SEQUENCE LISTING

<160> NUMBER OF SEQ ID NOS: 19

<210> SEQ ID NO 1
<211> LENGTH: 6821
<212> TYPE: DNA
<213> ORGANISM: Citrus Sudden Death Virus
<220> FEATURE:
<221> NAME/KEY: CDS
<222> LOCATION: (110)..(6673)

<400> SEQUENCE: 1

```
gtccctgtg atcgtctctc ccgccctcca gccggaaaga tatttttgct ttaactttc      60 tttgcactct tacgctcaga tctacgtgcc ttaggtcatc taagccgct atg gat cgc   118
                                                      Met Asp Arg
                                                        1 atc tct gcc cgc att ccc gtc gcg ccc gct tcc gcc ggc ccg acc gag    166
Ile Ser Ala Arg Ile Pro Val Ala Pro Ala Ser Ala Gly Pro Thr Glu
  5                  10                  15 tac act cca tac cca cac act cac cca ctc cta ccc cga ggt gtc ttc    214
Tyr Thr Pro Tyr Pro His Thr His Pro Leu Leu Pro Arg Gly Val Phe
 20                  25                  30                  35 acc tcc ggg cct att caa ccc tgt ctc cac ttt ctt cct cac cat gcc    262
Thr Ser Gly Pro Ile Gln Pro Cys Leu His Phe Leu Pro His His Ala
                 40                  45                  50 caa gat gcc ccc atc cgc tgc tac aga ccc ctc acc ttc gcc aac cat    310
Gln Asp Ala Pro Ile Arg Cys Tyr Arg Pro Leu Thr Phe Ala Asn His
             55                  60                  65 ctc cgc tat gac cgt tcc gcc tca tcg ctc aag act ccg ccc gtc aaa    358
Leu Arg Tyr Asp Arg Ser Ala Ser Ser Leu Lys Thr Pro Pro Val Lys
         70                  75                  80 ctc cca ctg acc ggt ggt acc ctt gcc gat gcc atc ctt tcc ttg gca    406
Leu Pro Leu Thr Gly Gly Thr Leu Ala Asp Ala Ile Leu Ser Leu Ala
     85                  90                  95 ccc acc act cac cgc gac acc atc gcc acc ccc ctc atg gaa gcc ctt    454
Pro Thr Thr His Arg Asp Thr Ile Ala Thr Pro Leu Met Glu Ala Leu
100                 105                 110                 115 gct gaa cct tac cgc caa tcc ttg agc acc tac cca tgg cac att cca    502
Ala Glu Pro Tyr Arg Gln Ser Leu Ser Thr Tyr Pro Trp His Ile Pro
                120                 125                 130 acc aat ctt cag ccc ttc ctc acc tct tgc gga atc acc act gct ggc    550
Thr Asn Leu Gln Pro Phe Leu Thr Ser Cys Gly Ile Thr Thr Ala Gly
            135                 140                 145 caa ggc ttc aag gcc cac cct cac cca gtg cac aag acc atc gag acc    598
Gln Gly Phe Lys Ala His Pro His Pro Val His Lys Thr Ile Glu Thr
        150                 155                 160 aat ctc ctc act aat gtc tgg ccc cac tac gcc acc act cct agt ggc    646
Asn Leu Leu Thr Asn Val Trp Pro His Tyr Ala Thr Thr Pro Ser Gly
    165                 170                 175 gtc atg ttc atg aaa cca tca aag ttt gag aag ctc aaa atc aaa cag    694
Val Met Phe Met Lys Pro Ser Lys Phe Glu Lys Leu Lys Ile Lys Gln
180                 185                 190                 195 ccc aac ttc tcc aag ctc tac aac tac cgc atc aca gcc aag gac acc    742
Pro Asn Phe Ser Lys Leu Tyr Asn Tyr Arg Ile Thr Ala Lys Asp Thr
                200                 205                 210 acc cgt tac ccc tcc act tcc cca gac ttg ccc acc gag gac acc tgc    790
Thr Arg Tyr Pro Ser Thr Ser Pro Asp Leu Pro Thr Glu Asp Thr Cys
            215                 220                 225 ttc atg cac gat gcc ctc atg tac tat tcc cct gga cag atc tgt gac    838
Phe Met His Asp Ala Leu Met Tyr Tyr Ser Pro Gly Gln Ile Cys Asp
        230                 235                 240
```

-continued

| | |
|---|---|
| ctc ttc ctc tcc cgc ccc agc ctc caa aag ctc tat gct tcc ctt gtt<br>Leu Phe Leu Ser Arg Pro Ser Leu Gln Lys Leu Tyr Ala Ser Leu Val<br>245                    250                        255 | 886 |
| gtt cct ccg gag agc gac ttc acc acc atc tcc ctc ttc cca gat ctc<br>Val Pro Pro Glu Ser Asp Phe Thr Thr Ile Ser Leu Phe Pro Asp Leu<br>260                    265                    270                275 | 934 |
| tac cgc tac cgg atc gag aaa gat cag ctc atc tac gag ctc gag cag<br>Tyr Arg Tyr Arg Ile Glu Lys Asp Gln Leu Ile Tyr Glu Leu Glu Gln<br>                    280                    285                    290 | 982 |
| aac ccc gcc cac aac tac atc cag cct cgc tct gcc atc gac tgg ctc<br>Asn Pro Ala His Asn Tyr Ile Gln Pro Arg Ser Ala Ile Asp Trp Leu<br>              295                    300                    305 | 1030 |
| aag acc acc acc atc cgc tgc cag gac ctc act ctc acc atc tcc cgc<br>Lys Thr Thr Thr Ile Arg Cys Gln Asp Leu Thr Leu Thr Ile Ser Arg<br>          310                    315                    320 | 1078 |
| cta gat tcc tgg ggc cca gtc cac tct ctc ctg atc caa aga ggc aag<br>Leu Asp Ser Trp Gly Pro Val His Ser Leu Leu Ile Gln Arg Gly Lys<br>325                    330                    335 | 1126 |
| ccc cct atc cat ctt gag gag gac tcc atc agc ttc cgt gcc cca aaa<br>Pro Pro Ile His Leu Glu Glu Asp Ser Ile Ser Phe Arg Ala Pro Lys<br>340                    345                    350                355 | 1174 |
| gca gtc ctc ctg cct gag cca gct tca ctc tcc caa tca gtc cgc gac<br>Ala Val Leu Leu Pro Glu Pro Ala Ser Leu Ser Gln Ser Val Arg Asp<br>                    360                    365                    370 | 1222 |
| cgc ctg gtc cct gct gat gtt tac cag gct ctc ttc atc tat gtc cgg<br>Arg Leu Val Pro Ala Asp Val Tyr Gln Ala Leu Phe Ile Tyr Val Arg<br>              375                    380                    385 | 1270 |
| gct gtc cgc acc ctc cgt gtg acc gac ccg gct ggc ttc gtt cgc act<br>Ala Val Arg Thr Leu Arg Val Thr Asp Pro Ala Gly Phe Val Arg Thr<br>          390                    395                    400 | 1318 |
| cag atc tct aag ccc gag tac tct tgg gtc act tcc tcc gcc tgg gac<br>Gln Ile Ser Lys Pro Glu Tyr Ser Trp Val Thr Ser Ser Ala Trp Asp<br>405                    410                    415 | 1366 |
| aat ctg gcc cac ttt gcc ttg gcc aca gct ccg cac aga ccc cac acc<br>Asn Leu Ala His Phe Ala Leu Ala Thr Ala Pro His Arg Pro His Thr<br>420                    425                    430                435 | 1414 |
| acc tac ttc ctg ttc aac tca acc gct gct cgg gtg gcc cat tgg ttc<br>Thr Tyr Phe Leu Phe Asn Ser Thr Ala Ala Arg Val Ala His Trp Phe<br>                    440                    445                    450 | 1462 |
| cgc act cat acc ctg gct ccg ctc tct ggc gcc act gct gcc gcc gcg<br>Arg Thr His Thr Leu Ala Pro Leu Ser Gly Ala Thr Ala Ala Ala Ala<br>              455                    460                    465 | 1510 |
| agc ctt ctc atg acc gcc agc tgg gga ttc cgt gcc atg atc tcc tct<br>Ser Leu Leu Met Thr Ala Ser Trp Gly Phe Arg Ala Met Ile Ser Ser<br>          470                    475                    480 | 1558 |
| cat ctt gtc tcc ctc tcc atc tgc aag cgc tgg ctc aaa gct cct cct<br>His Leu Val Ser Leu Ser Ile Cys Lys Arg Trp Leu Lys Ala Pro Pro<br>485                    490                    495 | 1606 |
| cat ctc ctc tgg ccc gag aaa gct ccc tgg ttc cag ctc acc ctg agg<br>His Leu Leu Trp Pro Glu Lys Ala Pro Trp Phe Gln Leu Thr Leu Arg<br>500                    505                    510                515 | 1654 |
| ccc aaa gtc act ggc cct ctg att gac ctg ccc att ctc cga ccc ttt<br>Pro Lys Val Thr Gly Pro Leu Ile Asp Leu Pro Ile Leu Arg Pro Phe<br>                    520                    525                    530 | 1702 |
| agg ctg ttc cct tcc aca tgc gcc aaa ctg ggc gcc aag cac cct gct<br>Arg Leu Phe Pro Ser Thr Cys Ala Lys Leu Gly Ala Lys His Pro Ala<br>              535                    540                    545 | 1750 |
| ctt gcc aca ttg ctt cct gct gct ccc agg ccc aca tgg ccc cta aag<br>Leu Ala Thr Leu Leu Pro Ala Ala Pro Arg Pro Thr Trp Pro Leu Lys<br>550                    555                    560 | 1798 |

```
gtt ggc ctc gca ctc gct gct gtc cca gtc tgc ctg ttc ttg tgg cgg     1846
Val Gly Leu Ala Leu Ala Ala Val Pro Val Cys Leu Phe Leu Trp Arg
    565                 570                 575 aaa ttc att ggt ccc gat tct cca cag gac atg cat gac agc tat cat     1894
Lys Phe Ile Gly Pro Asp Ser Pro Gln Asp Met His Asp Ser Tyr His
580                 585                 590                 595 gcc atg ttt cat cca cag cct tgg ggc ctc act ctc act cgc aag gct     1942
Ala Met Phe His Pro Gln Pro Trp Gly Leu Thr Leu Thr Arg Lys Ala
                600                 605                 610 atc tgc tgc gat agg gcc ccc ttt ctg ccc atc cct gtt gtt ccc agc     1990
Ile Cys Cys Asp Arg Ala Pro Phe Leu Pro Ile Pro Val Val Pro Ser
            615                 620                 625 tct gac ttc aag gcc ccg cca aca cct gcc acc cca cta ttg act tcc     2038
Ser Asp Phe Lys Ala Pro Pro Thr Pro Ala Thr Pro Leu Leu Thr Ser
        630                 635                 640 atc cct att aag ggt gtg gag cct caa gtt tct gga gaa gga gta cct     2086
Ile Pro Ile Lys Gly Val Glu Pro Gln Val Ser Gly Glu Gly Val Pro
    645                 650                 655 ccg cag tcg gct tca tca acc ggc ccg gca tcg gac tcc cgt cgt gcc     2134
Pro Gln Ser Ala Ser Ser Thr Gly Pro Ala Ser Asp Ser Arg Arg Ala
660                 665                 670                 675 ccg caa cca gct tca tca act ggt ccg gat ccg ccc acc cag aac acg     2182
Pro Gln Pro Ala Ser Ser Thr Gly Pro Asp Pro Pro Thr Gln Asn Thr
                680                 685                 690 agt gct gcc ccc caa cct ccc atc gaa tcc aaa gtt acc ttt gcc caa     2230
Ser Ala Ala Pro Gln Pro Pro Ile Glu Ser Lys Val Thr Phe Ala Gln
            695                 700                 705 ccc att gag agt gtg gca cct gta gtt cca gga gca gga gaa cct ccg     2278
Pro Ile Glu Ser Val Ala Pro Val Val Pro Gly Ala Gly Glu Pro Pro
        710                 715                 720 cag tcg gct tca tca acc ggc ccg gca tcg gtc tcc cgt cgt gac ccg     2326
Gln Ser Ala Ser Ser Thr Gly Pro Ala Ser Val Ser Arg Arg Asp Pro
    725                 730                 735 caa gtg gct tca tca acc act ccg gat gct ccc acc ctg gac gtc agc     2374
Gln Val Ala Ser Ser Thr Thr Pro Asp Ala Pro Thr Leu Asp Val Ser
740                 745                 750                 755 gtg acc cct cca aag act atc tat cct att gac cac ctc cag aac gac     2422
Val Thr Pro Pro Lys Thr Ile Tyr Pro Ile Asp His Leu Gln Asn Asp
                760                 765                 770 ttc ggc cct tgc cgt tgc tcc gtc tgt gaa cca ctt cag cct gcc ccc     2470
Phe Gly Pro Cys Arg Cys Ser Val Cys Glu Pro Leu Gln Pro Ala Pro
            775                 780                 785 gtc ccc tcc act cct ctc acc gtc tcg gat cat aaa gaa gcc cag gac     2518
Val Pro Ser Thr Pro Leu Thr Val Ser Asp His Lys Glu Ala Gln Asp
        790                 795                 800 gcc gaa gct ctt tcc tcg gcc ctc caa gcc ctc ggg ctc gct ccc acc     2566
Ala Glu Ala Leu Ser Ser Ala Leu Gln Ala Leu Gly Leu Ala Pro Thr
    805                 810                 815 cca cca gct cca cag tct cag aac ctc act gta gag tcc tca gga gcc     2614
Pro Pro Ala Pro Gln Ser Gln Asn Leu Thr Val Glu Ser Ser Gly Ala
820                 825                 830                 835 atg cat gcc tca tct tgg gat cag ctc tcc tcc cca tca tct gac tgg     2662
Met His Ala Ser Ser Trp Asp Gln Leu Ser Ser Pro Ser Ser Asp Trp
                840                 845                 850 gat cct tcc cct ctg gcc cgt gat agc tcc gcc tct ggt ccc cca ggc     2710
Asp Pro Ser Pro Leu Ala Arg Asp Ser Ser Ala Ser Gly Pro Pro Gly
            855                 860                 865 atg tac tca gat ctc ttt cca gct ccc tac ctt cca ggc acc ggt cag     2758
Met Tyr Ser Asp Leu Phe Pro Ala Pro Tyr Leu Pro Gly Thr Gly Gln
```

```
                870             875             880
ttc atc ttc cgc tcc agg gcc aat ggt cgg gcc aac atc cct tat ccc   2806
Phe Ile Phe Arg Ser Arg Ala Asn Gly Arg Ala Asn Ile Pro Tyr Pro
    885             890             895 gac atg gat tgc ctc ttg ctt tcc atc gag caa gcc acc cgc ctt ccc   2854
Asp Met Asp Cys Leu Leu Leu Ser Ile Glu Gln Ala Thr Arg Leu Pro
900             905             910             915 aag gag gct ctc tgg gac acc ctc tgt gcc aca tgc ccc gac tct ctc   2902
Lys Glu Ala Leu Trp Asp Thr Leu Cys Ala Thr Cys Pro Asp Ser Leu
            920             925             930 ctt gat cct gat acc att cgc cga gtc gga ttg tcc act gac cac ttt   2950
Leu Asp Pro Asp Thr Ile Arg Arg Val Gly Leu Ser Thr Asp His Phe
                935             940             945 gcc atc ctg gcc cac cac tac tcc ctc agg tgc cgc ttt cac acc gcc   2998
Ala Ile Leu Ala His His Tyr Ser Leu Arg Cys Arg Phe His Thr Ala
        950             955             960 cat ggt gtc att gag ctc ggc atg gct gat gcc acc tcc tca ttc gac   3046
His Gly Val Ile Glu Leu Gly Met Ala Asp Ala Thr Ser Ser Phe Asp
    965             970             975 atc gac cac act gct ggc aac ccc ggc cac ttc tcc ctc cgg caa tct   3094
Ile Asp His Thr Ala Gly Asn Pro Gly His Phe Ser Leu Arg Gln Ser
980             985             990             995 gcc act ccg agg cta aat gga gga att gct caa gat ctc gct gtg       3139
Ala Thr Pro Arg Leu Asn Gly Gly Ile Ala Gln Asp Leu Ala Val
            1000            1005            1010 gcc gct ctc agg ttc aac att gat ggc act ctc ctc cca atc cgc       3184
Ala Ala Leu Arg Phe Asn Ile Asp Gly Thr Leu Leu Pro Ile Arg
        1015            1020            1025 tca gtt cat gtc tat tcc act tgg cca aag aga gca aag aac ctg       3229
Ser Val His Val Tyr Ser Thr Trp Pro Lys Arg Ala Lys Asn Leu
    1030            1035            1040 tcg tcg aac atg aag aac ggc ttt gac ggc atc atg gcc aac atc       3274
Ser Ser Asn Met Lys Asn Gly Phe Asp Gly Ile Met Ala Asn Ile
1045            1050            1055 cac ccc acc aag acc aat gaa tcg aga gag aag atc ttg gca ctc       3319
His Pro Thr Lys Thr Asn Glu Ser Arg Glu Lys Ile Leu Ala Leu
            1060            1065            1070 gat tcg cag ctg gac atc gct gtc agg aga tcc gtc cgt ctg atc       3364
Asp Ser Gln Leu Asp Ile Ala Val Arg Arg Ser Val Arg Leu Ile
        1075            1080            1085 cat att gcc ggg ttc cca ggg tgc ggc aag tcc ttt ccc atc tcc       3409
His Ile Ala Gly Phe Pro Gly Cys Gly Lys Ser Phe Pro Ile Ser
    1090            1095            1100 cgc ctc ctc cgc act cca acc ttc agg aac ttt aag gtg gca gtt       3454
Arg Leu Leu Arg Thr Pro Thr Phe Arg Asn Phe Lys Val Ala Val
1105            1110            1115 ccc act gtt gag ctc cga gcc gag tgg aaa acc att act ggt ctc       3499
Pro Thr Val Glu Leu Arg Ala Glu Trp Lys Thr Ile Thr Gly Leu
            1120            1125            1130 ccg gcc tca gaa gcc tgg cgc atc ggc acc tgg gaa tcc tct ctc       3544
Pro Ala Ser Glu Ala Trp Arg Ile Gly Thr Trp Glu Ser Ser Leu
        1135            1140            1145 ctc aag tct gcc cgg gtc ctg gtc att gat gaa atc tac aag atg       3589
Leu Lys Ser Ala Arg Val Leu Val Ile Asp Glu Ile Tyr Lys Met
    1150            1155            1160 cca aga ggc tac att gat ctc gcc atc cac tct gat ccc acc att       3634
Pro Arg Gly Tyr Ile Asp Leu Ala Ile His Ser Asp Pro Thr Ile
1165            1170            1175 gaa atg gtc att gct ctc ggt gat cca ctc caa gga gag tac cac       3679
```

```
        Glu Met Val Ile Ala  Leu Gly Asp Pro Leu  Gln Gly Glu Tyr His
                        1180                 1185                 1190 tcc act cat cct tcc  tct acc aac tcc cgc  ctt ctc tct gag ccc        3724
Ser Thr His Pro Ser  Ser Thr Asn Ser Arg  Leu Leu Ser Glu Pro
                1195                 1200                 1205 cag cat ctc tcc atg  tac ctt gac ttc tac  tgc ttg tgg tcc cac        3769
Gln His Leu Ser Met  Tyr Leu Asp Phe Tyr  Cys Leu Trp Ser His
            1210                     1215                 1220 cgc gtt ccg cag aac  gtg gcc gcc ttc ttc  cat gtc aag acc acc        3814
Arg Val Pro Gln Asn  Val Ala Ala Phe Phe  His Val Lys Thr Thr
                1225                 1230                 1235 tcc aaa cag cct ggc  ttc tgc cgc tac cag  aga gag ctg ccg aac        3859
Ser Lys Gln Pro Gly  Phe Cys Arg Tyr Gln  Arg Glu Leu Pro Asn
                1240                 1245                 1250 tcc aga atc ctg gcc  aac tct cag aat gca  ggc cat acc ctc cag        3904
Ser Arg Ile Leu Ala  Asn Ser Gln Asn Ala  Gly His Thr Leu Gln
                1255                 1260                 1265 cag tgt ggc tac gct  gcc gtc acc att gcc  tcc agt cag ggc tcc        3949
Gln Cys Gly Tyr Ala  Ala Val Thr Ile Ala  Ser Ser Gln Gly Ser
                1270                 1275                 1280 acc tat gaa aat gcg  gcc tgc att cac ctg  gac cga aac agc tcc        3994
Thr Tyr Glu Asn Ala  Ala Cys Ile His Leu  Asp Arg Asn Ser Ser
                1285                 1290                 1295 ttg ctc tcc cct gct  cac tcc atg gtt gct  ctc act cgc tca aag        4039
Leu Leu Ser Pro Ala  His Ser Met Val Ala  Leu Thr Arg Ser Lys
                1300                 1305                 1310 gtt ggt gtc atc ttc  acc ggc gat ccc gcc  cag ctc tcc aat gct        4084
Val Gly Val Ile Phe  Thr Gly Asp Pro Ala  Gln Leu Ser Asn Ala
                1315                 1320                 1325 cca agc tcc aac cga  atg ttc tca gag ttc  ttc tca ggc cgc acc        4129
Pro Ser Ser Asn Arg  Met Phe Ser Glu Phe  Phe Ser Gly Arg Thr
                1330                 1335                 1340 cgc cct ctt cat gac  tgg ttc cac aat gag  ttc cca aag gcc act        4174
Arg Pro Leu His Asp  Trp Phe His Asn Glu  Phe Pro Lys Ala Thr
                1345                 1350                 1355 gtc ctc acc gag ccc  ctc aag act cgg ggg  ccc cgc ctc acc ggt        4219
Val Leu Thr Glu Pro  Leu Lys Thr Arg Gly  Pro Arg Leu Thr Gly
                1360                 1365                 1370 gct gcc tca cca tac  tcc aag gct gtc cca  atc cgc caa gcc tcc        4264
Ala Ala Ser Pro Tyr  Ser Lys Ala Val Pro  Ile Arg Gln Ala Ser
                1375                 1380                 1385 acc cca gct ctc aag  cct gat ttc caa ggg  gac gtc ata atc tca        4309
Thr Pro Ala Leu Lys  Pro Asp Phe Gln Gly  Asp Val Ile Ile Ser
                1390                 1395                 1400 gca ccc ata gtt ctc  ggc tcc ggc gag ctc  aat gcc cct caa gtc        4354
Ala Pro Ile Val Leu  Gly Ser Gly Glu Leu  Asn Ala Pro Gln Val
                1405                 1410                 1415 tcc tct cac ttc ctc  ccc gag act cgc cgt  cct ctc cac tgg gac        4399
Ser Ser His Phe Leu  Pro Glu Thr Arg Arg  Pro Leu His Trp Asp
                1420                 1425                 1430 att cca tct gcc atc  cct gag agt gcc acc  aga ccg gac tcc act        4444
Ile Pro Ser Ala Ile  Pro Glu Ser Ala Thr  Arg Pro Asp Ser Thr
                1435                 1440                 1445 gag ccc acc acc tcc  cat cca gag cca gtc  tac ccc ggg gaa act        4489
Glu Pro Thr Thr Ser  His Pro Glu Pro Val  Tyr Pro Gly Glu Thr
                1450                 1455                 1460 ttt gag aat ctt gct  gcc cac ttt ctc cct  gcc cac gac cca acc        4534
Phe Glu Asn Leu Ala  Ala His Phe Leu Pro  Ala His Asp Pro Thr
                1465                 1470                 1475
```

```
gat cgt gag atc tac tgg cag ggt cag ctg tcc aac cag ttc cca      4579
Asp Arg Glu Ile Tyr Trp Gln Gly Gln Leu Ser Asn Gln Phe Pro
            1480                1485                1490 cac atg gac aag gaa ttc cat ttg gct gca caa ccc atg agt ctc      4624
His Met Asp Lys Glu Phe His Leu Ala Ala Gln Pro Met Ser Leu
            1495                1500                1505 ctg gct gcc gtt cat caa gag aag caa gat ccc act cta ctg cca      4669
Leu Ala Ala Val His Gln Glu Lys Gln Asp Pro Thr Leu Leu Pro
            1510                1515                1520 gct tca atc caa aag aga ctc cgc ttc cgc ccc tcc gac aag ccc      4714
Ala Ser Ile Gln Lys Arg Leu Arg Phe Arg Pro Ser Asp Lys Pro
            1525                1530                1535 tac cag atc acc cca aaa gat gaa atc ctg ggc cag ctc ctc ttt      4759
Tyr Gln Ile Thr Pro Lys Asp Glu Ile Leu Gly Gln Leu Leu Phe
            1540                1545                1550 gaa ggc ctc tgc cga gcc tac cac aga tct cca ttt cac act gag      4804
Glu Gly Leu Cys Arg Ala Tyr His Arg Ser Pro Phe His Thr Glu
            1555                1560                1565 gcc ttt gat ccc gtg ctt ttc gcc gag tgc atc aat ctc aat gag      4849
Ala Phe Asp Pro Val Leu Phe Ala Glu Cys Ile Asn Leu Asn Glu
            1570                1575                1580 ttc gcc cag ctc tcg tcc aag acc cag gct act att atg ggc aat      4894
Phe Ala Gln Leu Ser Ser Lys Thr Gln Ala Thr Ile Met Gly Asn
            1585                1590                1595 gct cgc cgc tca gac cct gat tgg cgg tgg agc gca gtt cgc atc      4939
Ala Arg Arg Ser Asp Pro Asp Trp Arg Trp Ser Ala Val Arg Ile
            1600                1605                1610 ttc tcc aag acc caa cac aag gtg aat gaa ggg tcc att ttc cgc      4984
Phe Ser Lys Thr Gln His Lys Val Asn Glu Gly Ser Ile Phe Arg
            1615                1620                1625 tcc tgg aag gcc tgc caa act ttg gct ctc atg cat gat gct gtt      5029
Ser Trp Lys Ala Cys Gln Thr Leu Ala Leu Met His Asp Ala Val
            1630                1635                1640 gtt cta atc ctg ggc cct gtc aag aag tac cag cga gtc ttt gat      5074
Val Leu Ile Leu Gly Pro Val Lys Lys Tyr Gln Arg Val Phe Asp
            1645                1650                1655 cag aga gac cga ccc cga cac ctt tac atc cat gca ggc aac act      5119
Gln Arg Asp Arg Pro Arg His Leu Tyr Ile His Ala Gly Asn Thr
            1660                1665                1670 cca tca caa atg agc aac tgg tgt caa cag cat ctc act act gcc      5164
Pro Ser Gln Met Ser Asn Trp Cys Gln Gln His Leu Thr Thr Ala
            1675                1680                1685 gtc aag ttg gcc aat gac tac act gcc ttc gac cag tct cag cat      5209
Val Lys Leu Ala Asn Asp Tyr Thr Ala Phe Asp Gln Ser Gln His
            1690                1695                1700 ggt gag gcg gtc gtc ctt gaa aga aag aaa atg gaa aga ctc tcc      5254
Gly Glu Ala Val Val Leu Glu Arg Lys Lys Met Glu Arg Leu Ser
            1705                1710                1715 atc ccc cag gct ctc att gat ctt cac atc cat ctc aaa acc cat      5299
Ile Pro Gln Ala Leu Ile Asp Leu His Ile His Leu Lys Thr His
            1720                1725                1730 gtt tcc acc cag ttt ggc ccc ctc aca tgc atg cgc ctg act ggc      5344
Val Ser Thr Gln Phe Gly Pro Leu Thr Cys Met Arg Leu Thr Gly
            1735                1740                1745 gag cct ggc act tat gat gat aac tct gac tac aat ctt gca gtt      5389
Glu Pro Gly Thr Tyr Asp Asp Asn Ser Asp Tyr Asn Leu Ala Val
            1750                1755                1760 gtc aac tgt gag tac atg gct gcc aac act ccc act atg gtc tca      5434
Val Asn Cys Glu Tyr Met Ala Ala Asn Thr Pro Thr Met Val Ser
            1765                1770                1775
```

```
                                                           -continued ggc gac gac tcc ctc ctg gat cgt gag cct ccc act cgc cct gaa        5479
Gly Asp Asp Ser Leu Leu Asp Arg Glu Pro Pro Thr Arg Pro Glu
                1780             1785             1790 tgg gtc atc ctc cag cct ctt ctc agt ctc cgc ttc aag aaa gaa        5524
Trp Val Ile Leu Gln Pro Leu Leu Ser Leu Arg Phe Lys Lys Glu
        1795             1800             1805 agg ggt cgg tac gcc acc ttc tgt ggc tac tac gcc tcc cat gtc        5569
Arg Gly Arg Tyr Ala Thr Phe Cys Gly Tyr Tyr Ala Ser His Val
    1810             1815             1820 ggc tgt gtc cgc tcc ccc gtg gct ctc ttt gcc aag ctg gcc ata        5614
Gly Cys Val Arg Ser Pro Val Ala Leu Phe Ala Lys Leu Ala Ile
1825             1830             1835 gct gtc gat gac ggc tcc atc tct gac aaa atg gcc tca tac ctc        5659
Ala Val Asp Asp Gly Ser Ile Ser Asp Lys Met Ala Ser Tyr Leu
            1840             1845             1850 tct gaa ttt gct ctt ggc cac tcc ctt gga gac cat ctc tgg gaa        5704
Ser Glu Phe Ala Leu Gly His Ser Leu Gly Asp His Leu Trp Glu
        1855             1860             1865 gct ttg ccc ctc gag gcc gtt ccc ttc caa tct gcc tgc ttt gac        5749
Ala Leu Pro Leu Glu Ala Val Pro Phe Gln Ser Ala Cys Phe Asp
    1870             1875             1880 ttc ttc tgc cgc cgg gcc ccc aga cac ctc aaa ctc tct ctc atg        5794
Phe Phe Cys Arg Arg Ala Pro Arg His Leu Lys Leu Ser Leu Met
1885             1890             1895 ctc ggc gag gtc cca gaa tcc atc att gcc cgc atc ggg tca tcc        5839
Leu Gly Glu Val Pro Glu Ser Ile Ile Ala Arg Ile Gly Ser Ser
            1900             1905             1910 ttg aag tgg gcc tct cat gcc atc tac acc aca ctc tcc tct gcc        5884
Leu Lys Trp Ala Ser His Ala Ile Tyr Thr Thr Leu Ser Ser Ala
        1915             1920             1925 gct cga gtg gcc att ctg aga tcc tcc cgc aac agc aga tcc atg        5929
Ala Arg Val Ala Ile Leu Arg Ser Ser Arg Asn Ser Arg Ser Met
    1930             1935             1940 cca gat gac ccc gac acc act ctg cta caa ggt gaa ttg ctt cag        5974
Pro Asp Asp Pro Asp Thr Thr Leu Leu Gln Gly Glu Leu Leu Gln
1945             1950             1955 cac ttt caa gta cca ttc atg caa tct gac act ctc ctg cct ctc        6019
His Phe Gln Val Pro Phe Met Gln Ser Asp Thr Leu Leu Pro Leu
            1960             1965             1970 act ggt ggt tcc tct gct ccc atc ctc aca cca gaa gcc ttc tcc        6064
Thr Gly Gly Ser Ser Ala Pro Ile Leu Thr Pro Glu Ala Phe Ser
        1975             1980             1985 acc tcc ctc gcc ttc tcc atg gcc agc gat gcc caa gca ggt ccg        6109
Thr Ser Leu Ala Phe Ser Met Ala Ser Asp Ala Gln Ala Gly Pro
    1990             1995             2000 gcc ccc agt cgc gat gat cgc gtt gac cgc cag cct cgc ctt cct        6154
Ala Pro Ser Arg Asp Asp Arg Val Asp Arg Gln Pro Arg Leu Pro
2005             2010             2015 gct gct cct cgc gtt gct gaa gtt ggt ctc aat gcc ccg tcg gtc        6199
Ala Ala Pro Arg Val Ala Glu Val Gly Leu Asn Ala Pro Ser Val
            2020             2025             2030 gac tac ccg ttc cag tgg gtc gtc gcc tcc tac gac gga tca gaa        6244
Asp Tyr Pro Phe Gln Trp Val Val Ala Ser Tyr Asp Gly Ser Glu
        2035             2040             2045 gcc aag aac cta agt gat gat ctc tct ggc tct gcc act ctc acc        6289
Ala Lys Asn Leu Ser Asp Asp Leu Ser Gly Ser Ala Thr Leu Thr
    2050             2055             2060 aaa gtc atg gcc aac tac cga cat gct gag ctc aca tct gtt gag        6334
Lys Val Met Ala Asn Tyr Arg His Ala Glu Leu Thr Ser Val Glu
```

```
                   2065                 2070                 2075
ctg  gag  gtc  tgc  cct  ctt  gct  gca  gcc  ttc  tcc  aag  ccc  atc  tct        6379
Leu  Glu  Val  Cys  Pro  Leu  Ala  Ala  Ala  Phe  Ser  Lys  Pro  Ile  Ser
                   2080                 2085                 2090 gtg  tcg  gcc  gtc  tgg  acc  att  gcc  tcc  atc  tct  cca  gct  tcc  gcc        6424
Val  Ser  Ala  Val  Trp  Thr  Ile  Ala  Ser  Ile  Ser  Pro  Ala  Ser  Ala
                   2095                 2100                 2105 tct  gaa  acc  tcc  tac  tat  ggc  ggt  cga  ctc  ttc  act  gtt  ggc  ggt        6469
Ser  Glu  Thr  Ser  Tyr  Tyr  Gly  Gly  Arg  Leu  Phe  Thr  Val  Gly  Gly
                   2110                 2115                 2120 cct  gtc  ctc  atg  tcc  agc  acc  acc  cat  ctc  cct  gct  gat  ctc  acc        6514
Pro  Val  Leu  Met  Ser  Ser  Thr  Thr  His  Leu  Pro  Ala  Asp  Leu  Thr
                   2125                 2130                 2135 cgc  ctc  aat  cct  gtg  ctc  aag  ggc  ccc  gtc  aag  tac  aca  gac  tgc        6559
Arg  Leu  Asn  Pro  Val  Leu  Lys  Gly  Pro  Val  Lys  Tyr  Thr  Asp  Cys
                   2140                 2145                 2150 ccc  aga  ttc  tcc  tac  tcc  gtc  tac  tcc  aat  ggc  gga  acc  aag  ggc        6604
Pro  Arg  Phe  Ser  Tyr  Ser  Val  Tyr  Ser  Asn  Gly  Gly  Thr  Lys  Gly
                   2155                 2160                 2165 acc  aat  ctc  tgc  acc  atc  atc  ctc  cgg  gga  gtt  gtc  cgc  ctc  agc        6649
Thr  Asn  Leu  Cys  Thr  Ile  Ile  Leu  Arg  Gly  Val  Val  Arg  Leu  Ser
                   2170                 2175                 2180 ggc  ccc  tcc  ggt  aat  ctt  ctc  gct  taggcgagcc  tcttcaggtg  aaggaaaaca       6703
Gly  Pro  Ser  Gly  Asn  Leu  Leu  Ala
                   2185 cctcctggtc tcagccaggt aatgatgcta aacctccccc gctcaagcag caatgcctag              6763 ggttgccggt cgatccaaag accgttttc tttattattt aataaaaaaa aaaaaaaa                 6821

<210> SEQ ID NO 2
<211> LENGTH: 2188
<212> TYPE: PRT
<213> ORGANISM: Citrus Sudden Death Virus

<400> SEQUENCE: 2

Met Asp Arg Ile Ser Ala Arg Ile Pro Val Ala Pro Ala Ser Ala Gly
1               5                   10                  15

Pro Thr Glu Tyr Thr Pro Tyr Pro His Thr His Pro Leu Leu Pro Arg
            20                  25                  30

Gly Val Phe Thr Ser Gly Pro Ile Gln Pro Cys Leu His Phe Leu Pro
        35                  40                  45

His His Ala Gln Asp Ala Pro Ile Arg Cys Tyr Arg Pro Leu Thr Phe
    50                  55                  60

Ala Asn His Leu Arg Tyr Asp Arg Ser Ala Ser Leu Lys Thr Pro
65                  70                  75                  80

Pro Val Lys Leu Pro Leu Thr Gly Gly Thr Leu Ala Asp Ala Ile Leu
            85                  90                  95

Ser Leu Ala Pro Thr Thr His Arg Asp Thr Ile Ala Thr Pro Leu Met
        100                 105                 110

Glu Ala Leu Ala Glu Pro Tyr Arg Gln Ser Leu Ser Thr Tyr Pro Trp
    115                 120                 125

His Ile Pro Thr Asn Leu Gln Pro Phe Leu Thr Ser Cys Gly Ile Thr
130                 135                 140

Thr Ala Gly Gln Gly Phe Lys Ala His Pro His Pro Val His Lys Thr
145                 150                 155                 160

Ile Glu Thr Asn Leu Leu Thr Asn Val Trp Pro His Tyr Ala Thr Thr
            165                 170                 175
```

```
Pro Ser Gly Val Met Phe Met Lys Pro Ser Lys Phe Glu Lys Leu Lys
            180                 185                 190

Ile Lys Gln Pro Asn Phe Ser Lys Leu Tyr Asn Tyr Arg Ile Thr Ala
        195                 200                 205

Lys Asp Thr Thr Arg Tyr Pro Ser Thr Ser Pro Asp Leu Pro Thr Glu
210                 215                 220

Asp Thr Cys Phe Met His Asp Ala Leu Met Tyr Tyr Ser Pro Gly Gln
225                 230                 235                 240

Ile Cys Asp Leu Phe Leu Ser Arg Pro Ser Leu Gln Lys Leu Tyr Ala
                245                 250                 255

Ser Leu Val Val Pro Pro Glu Ser Asp Phe Thr Thr Ile Ser Leu Phe
            260                 265                 270

Pro Asp Leu Tyr Arg Tyr Arg Ile Glu Lys Asp Gln Leu Ile Tyr Glu
        275                 280                 285

Leu Glu Gln Asn Pro Ala His Asn Tyr Ile Gln Pro Arg Ser Ala Ile
    290                 295                 300

Asp Trp Leu Lys Thr Thr Thr Ile Arg Cys Gln Asp Leu Thr Leu Thr
305                 310                 315                 320

Ile Ser Arg Leu Asp Ser Trp Gly Pro Val His Ser Leu Leu Ile Gln
                325                 330                 335

Arg Gly Lys Pro Pro Ile His Leu Glu Glu Asp Ser Ile Ser Phe Arg
            340                 345                 350

Ala Pro Lys Ala Val Leu Leu Pro Glu Pro Ala Ser Leu Ser Gln Ser
        355                 360                 365

Val Arg Asp Arg Leu Val Pro Ala Asp Val Tyr Gln Ala Leu Phe Ile
370                 375                 380

Tyr Val Arg Ala Val Arg Thr Leu Arg Val Thr Asp Pro Ala Gly Phe
385                 390                 395                 400

Val Arg Thr Gln Ile Ser Lys Pro Glu Tyr Ser Trp Val Thr Ser Ser
                405                 410                 415

Ala Trp Asp Asn Leu Ala His Phe Ala Leu Ala Thr Ala Pro His Arg
            420                 425                 430

Pro His Thr Thr Tyr Phe Leu Phe Asn Ser Thr Ala Ala Arg Val Ala
        435                 440                 445

His Trp Phe Arg Thr His Thr Leu Ala Pro Leu Ser Gly Ala Thr Ala
    450                 455                 460

Ala Ala Ala Ser Leu Leu Met Thr Ala Ser Trp Gly Phe Arg Ala Met
465                 470                 475                 480

Ile Ser Ser His Leu Val Ser Leu Ser Ile Cys Lys Arg Trp Leu Lys
                485                 490                 495

Ala Pro Pro His Leu Leu Trp Pro Glu Lys Ala Pro Trp Phe Gln Leu
            500                 505                 510

Thr Leu Arg Pro Lys Val Thr Gly Pro Leu Ile Asp Leu Pro Ile Leu
        515                 520                 525

Arg Pro Phe Arg Leu Phe Pro Ser Thr Cys Ala Lys Leu Gly Ala Lys
    530                 535                 540

His Pro Ala Leu Ala Thr Leu Pro Ala Ala Pro Arg Pro Thr Trp
545                 550                 555                 560

Pro Leu Lys Val Gly Leu Ala Leu Ala Ala Val Pro Val Cys Leu Phe
                565                 570                 575

Leu Trp Arg Lys Phe Ile Gly Pro Asp Ser Pro Gln Asp Met His Asp
            580                 585                 590

Ser Tyr His Ala Met Phe His Pro Gln Pro Trp Gly Leu Thr Leu Thr
```

-continued

```
                595                 600                 605
    Arg Lys Ala Ile Cys Cys Asp Arg Ala Pro Phe Leu Pro Ile Pro Val
        610                 615                 620

Val Pro Ser Ser Asp Phe Lys Ala Pro Thr Pro Ala Thr Pro Leu
    625                 630                 635                 640

Leu Thr Ser Ile Pro Ile Lys Gly Val Glu Pro Gln Val Ser Gly Glu
                    645                 650                 655

Gly Val Pro Pro Gln Ser Ala Ser Ser Thr Gly Pro Ala Ser Asp Ser
                    660                 665                 670

Arg Arg Ala Pro Gln Pro Ala Ser Ser Thr Gly Pro Asp Pro Pro Thr
                    675                 680                 685

Gln Asn Thr Ser Ala Ala Pro Gln Pro Pro Ile Glu Ser Lys Val Thr
    690                 695                 700

Phe Ala Gln Pro Ile Glu Ser Val Ala Pro Val Pro Gly Ala Gly
    705                 710                 715                 720

Glu Pro Pro Gln Ser Ala Ser Ser Thr Gly Pro Ala Ser Val Ser Arg
                    725                 730                 735

Arg Asp Pro Gln Val Ala Ser Ser Thr Thr Pro Asp Ala Pro Thr Leu
                    740                 745                 750

Asp Val Ser Val Thr Pro Pro Lys Thr Ile Tyr Pro Ile Asp His Leu
                    755                 760                 765

Gln Asn Asp Phe Gly Pro Cys Arg Cys Ser Val Cys Glu Pro Leu Gln
    770                 775                 780

Pro Ala Pro Val Pro Ser Thr Pro Leu Thr Val Ser Asp His Lys Glu
    785                 790                 795                 800

Ala Gln Asp Ala Glu Ala Leu Ser Ser Ala Leu Gln Ala Leu Gly Leu
                    805                 810                 815

Ala Pro Thr Pro Pro Ala Pro Gln Ser Gln Asn Leu Thr Val Glu Ser
                    820                 825                 830

Ser Gly Ala Met His Ala Ser Ser Trp Asp Gln Leu Ser Ser Pro Ser
                    835                 840                 845

Ser Asp Trp Asp Pro Ser Pro Leu Ala Arg Asp Ser Ser Ala Ser Gly
                    850                 855                 860

Pro Pro Gly Met Tyr Ser Asp Leu Phe Pro Ala Pro Tyr Leu Pro Gly
    865                 870                 875                 880

Thr Gly Gln Phe Ile Phe Arg Ser Arg Ala Asn Gly Arg Ala Asn Ile
                    885                 890                 895

Pro Tyr Pro Asp Met Asp Cys Leu Leu Leu Ser Ile Glu Gln Ala Thr
                    900                 905                 910

Arg Leu Pro Lys Glu Ala Leu Trp Asp Thr Leu Cys Ala Thr Cys Pro
        915                 920                 925

Asp Ser Leu Leu Asp Pro Asp Thr Ile Arg Arg Val Gly Leu Ser Thr
        930                 935                 940

Asp His Phe Ala Ile Leu Ala His His Tyr Ser Leu Arg Cys Arg Phe
    945                 950                 955                 960

His Thr Ala His Gly Val Ile Glu Leu Gly Met Ala Asp Ala Thr Ser
                    965                 970                 975

Ser Phe Asp Ile Asp His Thr Ala Gly Asn Pro Gly His Phe Ser Leu
                    980                 985                 990

Arg Gln Ser Ala Thr Pro Arg Leu  Asn Gly Gly Ile Ala  Gln Asp Leu
                    995                 1000                1005

Ala Val  Ala Ala Leu Arg Phe  Asn Ile Asp Gly Thr  Leu Leu Pro
        1010                1015                1020
```

```
Ile Arg Ser Val His Val Tyr Ser Thr Trp Pro Lys Arg Ala Lys
1025                1030                1035

Asn Leu Ser Ser Asn Met Lys Asn Gly Phe Asp Gly Ile Met Ala
1040                1045                1050

Asn Ile His Pro Thr Lys Thr Asn Glu Ser Arg Glu Lys Ile Leu
1055                1060                1065

Ala Leu Asp Ser Gln Leu Asp Ile Ala Val Arg Arg Ser Val Arg
1070                1075                1080

Leu Ile His Ile Ala Gly Phe Pro Gly Cys Gly Lys Ser Phe Pro
1085                1090                1095

Ile Ser Arg Leu Leu Arg Thr Pro Thr Phe Arg Asn Phe Lys Val
1100                1105                1110

Ala Val Pro Thr Val Glu Leu Arg Ala Glu Trp Lys Thr Ile Thr
1115                1120                1125

Gly Leu Pro Ala Ser Glu Ala Trp Arg Ile Gly Thr Trp Glu Ser
1130                1135                1140

Ser Leu Leu Lys Ser Ala Arg Val Leu Val Ile Asp Glu Ile Tyr
1145                1150                1155

Lys Met Pro Arg Gly Tyr Ile Asp Leu Ala Ile His Ser Asp Pro
1160                1165                1170

Thr Ile Glu Met Val Ile Ala Leu Gly Asp Pro Leu Gln Gly Glu
1175                1180                1185

Tyr His Ser Thr His Pro Ser Ser Thr Asn Ser Arg Leu Leu Ser
1190                1195                1200

Glu Pro Gln His Leu Ser Met Tyr Leu Asp Phe Tyr Cys Leu Trp
1205                1210                1215

Ser His Arg Val Pro Gln Asn Val Ala Ala Phe Phe His Val Lys
1220                1225                1230

Thr Thr Ser Lys Gln Pro Gly Phe Cys Arg Tyr Gln Arg Glu Leu
1235                1240                1245

Pro Asn Ser Arg Ile Leu Ala Asn Ser Gln Asn Ala Gly His Thr
1250                1255                1260

Leu Gln Gln Cys Gly Tyr Ala Ala Val Thr Ile Ala Ser Ser Gln
1265                1270                1275

Gly Ser Thr Tyr Glu Asn Ala Ala Cys Ile His Leu Asp Arg Asn
1280                1285                1290

Ser Ser Leu Leu Ser Pro Ala His Ser Met Val Ala Leu Thr Arg
1295                1300                1305

Ser Lys Val Gly Val Ile Phe Thr Gly Asp Pro Ala Gln Leu Ser
1310                1315                1320

Asn Ala Pro Ser Ser Asn Arg Met Phe Ser Glu Phe Phe Ser Gly
1325                1330                1335

Arg Thr Arg Pro Leu His Asp Trp Phe His Asn Glu Phe Pro Lys
1340                1345                1350

Ala Thr Val Leu Thr Glu Pro Leu Lys Thr Arg Gly Pro Arg Leu
1355                1360                1365

Thr Gly Ala Ala Ser Pro Tyr Ser Lys Ala Val Pro Ile Arg Gln
1370                1375                1380

Ala Ser Thr Pro Ala Leu Lys Pro Asp Phe Gln Gly Asp Val Ile
1385                1390                1395

Ile Ser Ala Pro Ile Val Leu Gly Ser Gly Glu Leu Asn Ala Pro
1400                1405                1410
```

```
Gln Val Ser Ser His Phe Leu Pro Glu Thr Arg Arg Pro Leu His
1415                1420                1425

Trp Asp Ile Pro Ser Ala Ile Pro Glu Ser Ala Thr Arg Pro Asp
1430                1435                1440

Ser Thr Glu Pro Thr Thr Ser His Pro Glu Pro Val Tyr Pro Gly
1445                1450                1455

Glu Thr Phe Glu Asn Leu Ala Ala His Phe Leu Pro Ala His Asp
1460                1465                1470

Pro Thr Asp Arg Glu Ile Tyr Trp Gln Gly Gln Leu Ser Asn Gln
1475                1480                1485

Phe Pro His Met Asp Lys Glu Phe His Leu Ala Ala Gln Pro Met
1490                1495                1500

Ser Leu Leu Ala Ala Val His Gln Glu Lys Gln Asp Pro Thr Leu
1505                1510                1515

Leu Pro Ala Ser Ile Gln Lys Arg Leu Arg Phe Arg Pro Ser Asp
1520                1525                1530

Lys Pro Tyr Gln Ile Thr Pro Lys Asp Glu Ile Leu Gly Gln Leu
1535                1540                1545

Leu Phe Glu Gly Leu Cys Arg Ala Tyr His Arg Ser Pro Phe His
1550                1555                1560

Thr Glu Ala Phe Asp Pro Val Leu Phe Ala Glu Cys Ile Asn Leu
1565                1570                1575

Asn Glu Phe Ala Gln Leu Ser Ser Lys Thr Gln Ala Thr Ile Met
1580                1585                1590

Gly Asn Ala Arg Arg Ser Asp Pro Asp Trp Arg Trp Ser Ala Val
1595                1600                1605

Arg Ile Phe Ser Lys Thr Gln His Lys Val Asn Glu Gly Ser Ile
1610                1615                1620

Phe Arg Ser Trp Lys Ala Cys Gln Thr Leu Ala Leu Met His Asp
1625                1630                1635

Ala Val Val Leu Ile Leu Gly Pro Val Lys Lys Tyr Gln Arg Val
1640                1645                1650

Phe Asp Gln Arg Asp Arg Pro Arg His Leu Tyr Ile His Ala Gly
1655                1660                1665

Asn Thr Pro Ser Gln Met Ser Asn Trp Cys Gln Gln His Leu Thr
1670                1675                1680

Thr Ala Val Lys Leu Ala Asn Asp Tyr Thr Ala Phe Asp Gln Ser
1685                1690                1695

Gln His Gly Glu Ala Val Val Leu Glu Arg Lys Lys Met Glu Arg
1700                1705                1710

Leu Ser Ile Pro Gln Ala Leu Ile Asp Leu His Ile His Leu Lys
1715                1720                1725

Thr His Val Ser Thr Gln Phe Gly Pro Leu Thr Cys Met Arg Leu
1730                1735                1740

Thr Gly Glu Pro Gly Thr Tyr Asp Asp Asn Ser Asp Tyr Asn Leu
1745                1750                1755

Ala Val Val Asn Cys Glu Tyr Met Ala Ala Asn Thr Pro Thr Met
1760                1765                1770

Val Ser Gly Asp Asp Ser Leu Leu Asp Arg Glu Pro Pro Thr Arg
1775                1780                1785

Pro Glu Trp Val Ile Leu Gln Pro Leu Leu Ser Leu Arg Phe Lys
1790                1795                1800

Lys Glu Arg Gly Arg Tyr Ala Thr Phe Cys Gly Tyr Tyr Ala Ser
```

1805                1810                1815

His Val Gly Cys Val Arg Ser Pro Val Ala Leu Phe Ala Lys Leu
    1820                1825                1830

Ala Ile Ala Val Asp Asp Gly Ser Ile Ser Asp Lys Met Ala Ser
    1835                1840                1845

Tyr Leu Ser Glu Phe Ala Leu Gly His Ser Leu Gly Asp His Leu
    1850                1855                1860

Trp Glu Ala Leu Pro Leu Glu Ala Val Pro Phe Gln Ser Ala Cys
    1865                1870                1875

Phe Asp Phe Phe Cys Arg Arg Ala Pro Arg His Leu Lys Leu Ser
    1880                1885                1890

Leu Met Leu Gly Glu Val Pro Glu Ser Ile Ile Ala Arg Ile Gly
    1895                1900                1905

Ser Ser Leu Lys Trp Ala Ser His Ala Ile Tyr Thr Thr Leu Ser
    1910                1915                1920

Ser Ala Ala Arg Val Ala Ile Leu Arg Ser Ser Arg Asn Ser Arg
    1925                1930                1935

Ser Met Pro Asp Asp Pro Asp Thr Thr Leu Leu Gln Gly Glu Leu
    1940                1945                1950

Leu Gln His Phe Gln Val Pro Phe Met Gln Ser Asp Thr Leu Leu
    1955                1960                1965

Pro Leu Thr Gly Gly Ser Ser Ala Pro Ile Leu Thr Pro Glu Ala
    1970                1975                1980

Phe Ser Thr Ser Leu Ala Phe Ser Met Ala Ser Asp Ala Gln Ala
    1985                1990                1995

Gly Pro Ala Pro Ser Arg Asp Asp Arg Val Asp Arg Gln Pro Arg
    2000                2005                2010

Leu Pro Ala Ala Pro Arg Val Ala Glu Val Gly Leu Asn Ala Pro
    2015                2020                2025

Ser Val Asp Tyr Pro Phe Gln Trp Val Val Ala Ser Tyr Asp Gly
    2030                2035                2040

Ser Glu Ala Lys Asn Leu Ser Asp Asp Leu Ser Gly Ser Ala Thr
    2045                2050                2055

Leu Thr Lys Val Met Ala Asn Tyr Arg His Ala Glu Leu Thr Ser
    2060                2065                2070

Val Glu Leu Glu Val Cys Pro Leu Ala Ala Ala Phe Ser Lys Pro
    2075                2080                2085

Ile Ser Val Ser Ala Val Trp Thr Ile Ala Ser Ile Ser Pro Ala
    2090                2095                2100

Ser Ala Ser Glu Thr Ser Tyr Tyr Gly Gly Arg Leu Phe Thr Val
    2105                2110                2115

Gly Gly Pro Val Leu Met Ser Ser Thr Thr His Leu Pro Ala Asp
    2120                2125                2130

Leu Thr Arg Leu Asn Pro Val Leu Lys Gly Pro Val Lys Tyr Thr
    2135                2140                2145

Asp Cys Pro Arg Phe Ser Tyr Ser Val Tyr Ser Asn Gly Gly Thr
    2150                2155                2160

Lys Gly Thr Asn Leu Cys Thr Ile Ile Leu Arg Gly Val Val Arg
    2165                2170                2175

Leu Ser Gly Pro Ser Gly Asn Leu Leu Ala
    2180                2185

<210> SEQ ID NO 3

```
<211> LENGTH: 154
<212> TYPE: PRT
<213> ORGANISM: Citrus Sudden Death Virus

<400> SEQUENCE: 3

Met Ile Ser Leu Ala Leu Pro Leu Ser Pro Lys Ser Trp Pro Thr Thr
1               5                   10                  15

Asp Met Leu Ser Ser His Leu Leu Ser Trp Arg Ser Ala Leu Leu Leu
            20                  25                  30

Gln Pro Ser Pro Ser Pro Ser Leu Cys Arg Pro Ser Gly Pro Leu Pro
        35                  40                  45

Pro Ser Leu Gln Leu Pro Pro Leu Lys Pro Pro Thr Met Ala Val Asp
    50                  55                  60

Ser Ser Leu Leu Ala Val Leu Ser Ser Cys Pro Ala Pro Pro Ile Ser
65                  70                  75                  80

Leu Leu Ile Ser Pro Ala Ser Ile Leu Cys Ser Arg Ala Pro Ser Ser
                85                  90                  95

Thr Gln Thr Ala Pro Asp Ser Pro Thr Pro Ser Thr Pro Met Ala Glu
            100                 105                 110

Pro Arg Ala Pro Ile Ser Ala Pro Ser Ser Ser Gly Glu Leu Ser Ala
        115                 120                 125

Ser Ala Ala Pro Pro Val Ile Phe Ser Leu Arg Arg Ala Ser Ser Gly
    130                 135                 140

Glu Gly Lys His Leu Leu Val Ser Ala Arg
145                 150

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtcagctgtc caaccagttc c                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtgaagatca atgagagcct g                                              21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tggagctccc tgcccacgac ccaac                                          25

<210> SEQ ID NO 7
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 7
tctagagcct gggggatgga gagc                                              24

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Gly Pro Ala Pro Ser Arg Asp Asp Arg Val Asp Arg Gln
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Ser Arg Asp Asp Arg Val Asp Arg Gln Pro Arg Leu Pro
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Gly Ser Glu Ala Lys Asn Leu Ser Asp Asp Leu Ser Gly
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Ala Ser Ala Ser Glu Thr Ser Tyr Tyr Gly Gly Arg Leu
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Phe Ser Tyr Ser Val Tyr Ser Asn Gly Gly Thr Lys Gly Thr
1               5                   10                  15
```

<210> SEQ ID NO 13
<211> LENGTH: 6509
<212> TYPE: DNA
<213> ORGANISM: Oat Blue Dwarf Virus

<400> SEQUENCE: 13

| | | | | | | |
|---|---|---|---|---|---|---|
| gtgtcccagt | gtcattattc | cgctcagttt | cagatctgcc | ggaattctcc | aagcatcccg | 60 |
| ccccaaaagc | cggctgctta | aaatctgatc | ttctccatct | tgtcaagtgt | cgttatgacc | 120 |
| acatacgcct | ccacccgct | gctccccacc | ccgacctcct | tcgccactat | cactgggggt | 180 |
| ggtttgaagg | atgttatcga | aaccctctcg | tccaccatcc | acagagacac | gatcgcagca | 240 |
| cccctcatgg | agaccctcgc | ctcgccttac | cgagactccc | ttcgcgactt | cccttgggcc | 300 |
| gtccccgcct | ccgccctgcc | cttcctccag | gaatgtggca | tcacggtcgc | cggccacggt | 360 |
| ttcaaagctc | atccccaccc | tgtccacaaa | accatcgaga | cccacctcct | ccacaaggtt | 420 |
| tggcctcact | atgcccaagt | cccttcttcc | gtcctcttca | tgaagccctc | gaagttcgcc | 480 |
| aaactccagc | ggggcaacgc | caacttctcc | gcactccaca | actatcgcct | caccgccaaa | 540 |
| gacaccccgc | ggtatcctaa | cacttcaacc | tctctcccg | acaccgagac | cgccttcatg | 600 |
| catgacgccc | tcatgtatta | cacccccgct | caaattgttg | acctgttcct | ttcctgcccg | 660 |
| aagctcgaga | aactgtacgc | ctcccttgtc | gtccccccg | agtcctcctt | cacctctatc | 720 |
| tctctccatc | cagatcttta | ccgctttcgc | tttgacgggg | accgtttgat | ttatgagttg | 780 |
| gagggcaacc | ccgcccacaa | ctacacccaa | cctcgatccg | ccctcgactg | gctccgcaca | 840 |
| accaccatcc | gcggaccagg | cgtttctctc | accgtgtcca | ggctcgactc | gtggggtccc | 900 |
| tgccattccc | tcctcatcca | gcgcggcatt | cccccatgc | acgccgagca | cgactccatc | 960 |
| tcgttcaggg | gtccacgcgc | cgtcgccatt | cccgagccct | cctccctcca | ccaggatctg | 1020 |
| cgccaccgtc | tcgttccaga | ggacgtgtat | aacgccctct | tcctctacgt | ccgcgctgtc | 1080 |
| cgcacgctcc | gcgtaaccga | tcccgccggc | tttgtccgca | cccagtgctc | taagcccgag | 1140 |
| tacgcttggg | tcacttcctc | cgcttgggac | aacttggccc | acttcgccct | cctcaccgct | 1200 |
| ccacaccggc | cccgcacctc | gttctaccta | ttctcctcta | ccttccagcg | ccttgagcac | 1260 |
| tgggtccgcc | atcacaccct | cctcctcgcc | ggcctcacca | cagcctttgc | tctcccgccg | 1320 |
| tctgcctggc | tcgcgaacct | cgtcgcccgc | gcctccgctt | cacacatcca | aggcctcgcg | 1380 |
| ctagcccgcc | ggtggctcat | cactcccct | catctcttcc | gccccctcc | accccaagc | 1440 |
| ttcgctcttc | ttctccagcg | caactccacc | ggcccggtcc | ttctccgtgg | ctcccgcctc | 1500 |
| gagtttgagg | ccttccctc | tctcgcccca | caactcgccc | gtcgctttcc | attcctcgct | 1560 |
| cgccttctcc | cccagaaacc | catcgacccc | tgggtcgtcg | cgagcctcgc | tgtcgccgtt | 1620 |
| gctataccg | ccgcctccct | cgccgttcgc | tggttcttcg | gccccgacac | cccccaagcc | 1680 |
| atgcacgacc | gataccacac | catgttccac | cccagagagt | ggcgcctcac | cctgcccagg | 1740 |
| ggccccatct | catgtggccg | ctccagcttc | tccccccttc | cccaccccacc | ttcgcccact | 1800 |
| cccgctcccg | actcccgagc | tgaaccctc | cagccaccct | ccgctccacc | ctcgacccac | 1860 |
| gagccggctc | ccgccgatct | cgagcccaa | gctcctccgg | ccacgcccc | ccagaccgag | 1920 |
| cctccgagtc | ccgtgatcga | gcaagaagcg | cgtccgaatc | cccttccgc | tcctgccccg | 1980 |
| ctttctgctc | ccaccccctc | cgcttccgcg | ccttcacttg | cccaacacc | ctcggccccc | 2040 |
| gagcctccct | cgccgaccgc | ttccgagcag | gccgcgtccc | tcatccctgc | tccctcttcc | 2100 |
| gccctcgtcg | tggagccatc | cggcgtcgtc | tctgcctcat | cttggggcgc | caccaaccag | 2160 |

```
ccggccgatc aagtcgatga ctcccctctc gctcgcgatc ccagcgcctc cggccccgtc    2220
cgcttctatc gagacctctt ccccgccaac tacgcgggtg attccggcac cttcgacttc    2280
cgcgcccgcg cctcaggccg ctctcccacc ccatacccg ccatggattg cctcctcgtc     2340
gccaccgagc aagccacccg catctctcga gaggccctct gggactgcct cacagccacc    2400
tgccccgact cattcctcga ccccaagagc atcgcccagc atggcctcag caccgatcac    2460
ttcgtcatcc tcgctcatcg cttttcccta tgtgccaact tccactccgc cgagcacgtc    2520
attcagctcg ggatggccga tgccacctcc attttcatga tcaaccacac ggctggctcc    2580
gcgggcctcc cgggccactt ctccctccgc ctgggtgacc agccccgtgc cctcaacggt    2640
ggcctcgctc aggacctcgc cgtcgccgcc ctccgattca acatctccgg tgatctcctc    2700
ccaacccgat ccgttcacac ttacaggtct tggccaaagc gcgccaagaa ccttgtgtcc    2760
aacatgaaga acggctttga cggagtcatg gccagcatca acccgatccg acccagcgat    2820
gctcgcgaga agatcgtcgc cctcgacggt ctcctagaca ttgcccgacc ccgatccgtc    2880
cgcctcatcc acattgctgg tttcccaggc tgcggaaaaa cacatccgat caccaagctc    2940
ctccacaccg ccgccttccg cgacttcaaa ctcgccgtcc cgaccaccga gctccggtct    3000
gagtggaaag agctcatgaa gctctcaccc tctcaggcct ggcgcttcgg cacctgggag    3060
tcctcccttc tcaagagcgc caggatcctc gtgatcgatg agatctacaa gttgccccga    3120
gggtacctcg acctagccat ccactccgac tcgtccatcg agtttgttat cgccctggga    3180
gatcctctgc aaggcgagta tcactccact catcccagct cctccaactc tcgcctcatt    3240
cccgaagtca gccatctcgc tccctacctc gactactact gcctctggag ttaccgcgtc    3300
ccccaagacg tcgccgcttt cttccaggtt cagagccaca ccctgctct  cgggtttgcc    3360 cgtctctcga agcagtttcc cacgaccggg cgcgtcctca ccaactcaca gaactcgatg    3420
cttaccatga cgcagtgcgg ctactctgcc gtcaccattg cctcaagcca gggttccacc    3480
tacagcggcg ccacgcacat ccaccttgac cgcaactcat cgctcctctc cccttcgaac    3540
tccctcgtcg ccctcactcg ctcgagaacc ggcgtgttct ctccggggga ccctgctctt    3600
ctcaacggtg gtcccaactc caacctcatg ttctctgcct tctttcaggg caagtctcgc    3660
cacattcgcg cctggttccc caccctttc cctacggcca ctctcctctt ctcccccctc    3720
cgccaacgcc acaaccgcct cactggcgcc ctcgctcccg cccaaccttc ccacctcctg    3780
ctccctgacc ttccgagcct ccctcctctc cccgcctccg gtccctactc ccgctcattc    3840
ccagttcgat ctcgcttcgc cgcggccgtc aagccttccg accggtcaga cgtcctctcg    3900
tgggccccta tcgccgtcgg tgacggggaa accaacgccc ctcgcattga cacctccttc    3960
ctgcccgaaa ctcgccgccc gcttcatttt gatcttccct cgttccgccc ccaagcccca    4020
ccgcctccct ctgacccagc cccttctggg accgcctttg agcccgttta ccccggcgaa    4080
accttcgaaa atttggtcgc ccacttcctt ccggctcacg accccactga ccgcgaaatc    4140
cactggcgtc ggcagctttc caaccagttt ccccatgtcg ataaggagta ccacctcgcg    4200
gctcagccaa tgacgctcct cgctcccatc cacgactcca agcacgaccc caccctcctt    4260
gccgcctcca tccagaaacg acttcgattt cgaccctccg cctctcccta ccgaatctcc    4320
cctcgtgacg agctgcttgg ccagctcctc tacgagagtc tctgccgcgc gtatcatcgt    4380
tccccaacca ccaccaccc tttcgatgag gccctcttcg tcgagtgtat cgacctgaac    4440
gaattcgctc aactcaccag caaaactcag gccgtcatca tgggcaacgc ccgccgctct    4500
```

-continued

| | |
|---|---|
| gacccagact ggcgctggtc cgccgtccgg atcttcagca aaacccagca caaggtcaac | 4560 |
| gaaggttcga tctttggagc ctggaaagct tgccagaccc tcgctctcat gcacgacgcc | 4620 |
| gtcgttctgc tccttggccc cgtcaagaag tatcaacgcg tcttcgatgc tcgagaccgc | 4680 |
| cccgccacc tctacatcca cgccggccag acgccctctt ccatgagcct gtggtgccag | 4740 |
| acccacctca ccccgctgt caagctcgcg aacgactaca ccgctttcga ccagtctcag | 4800 |
| catggcgagg ccgtcgtcct cgagagaaag aagatggaac gcctttccat cccggatcac | 4860 |
| ctcatctccc tccacgttca ccttaagacc catgtcgaaa cccagtttgg ccctctcacc | 4920 |
| tgcatgcgcc taaccggcga gcctggcacc tacgacgaca cactgactga taacctcgcc | 4980 |
| gtcatcaacc tcgagtacgc ggctgcccac gtcccgacca tggtctcggg cgacgattca | 5040 |
| ctccttgact cgagcccccc acgccgccca gagtgggtcg ccatcgaacc tcttttagcc | 5100 |
| ctccgcttca agaaggagcg cggtctgtat gccaccttct gcggctacta cgcctcgcga | 5160 |
| gttggctgcg tccgatctcc catcgccctc ttcgctaagc tcgccatcgc cgtcgacgac | 5220 |
| tcatccatct ccgacaagct cgccgcatac ctcatggagt tcgcggtcgg tcactctctc | 5280 |
| ggcgactctc tttggtccgc cctcccccctg tccgccgtcc cctttcagtc agcctgtttc | 5340 |
| gatttcttct gccgccgcgc tccccgcgat ctaaagctcg cccttcacct gggcgaagtc | 5400 |
| cctgaaacca tcatccaacg cctctcccac ctctcctggc tatcccacgc cgtctacagc | 5460 |
| ctcctcccat ctcgccttcg cctcgccatc cttcacagct cacgcagca ccgttccctc | 5520 |
| cccgaagacc cagccgtttc ttcgcttcag ggtgaattgc ttcagacgtt ccatgctcca | 5580 |
| atgccctctc tcccttcact cccactcttc ggcggtctat ctcccgacaa catcctcact | 5640 |
| ccccacgagt tccgcaccgc cctctacgaa agctccgcct accctactcc tcccaactct | 5700 |
| ccgacctcca tgtcaggaat ccatgcctcg caagttggtc cgccccccgc cagcgatgat | 5760 |
| cgcactgacc gccagccttc tcttcctctt gctcctcgta ttgtggagag ctctctcgcc | 5820 |
| gtgccgcacg tcgacgtccc gttccaatgg ccgtcgcgt cgtacgccgg agactccgcc | 5880 |
| aagttcctca ccgacgacct ctcaggatcc tctcacctga gccgcctcac catcggctat | 5940 |
| cgccacgccg agctcatctc cgccgagctc gagttcgccc ccttgccgc cgccttcgcc | 6000 |
| aagcccatct ccgtcaccgc cgtctggacc atagcctcca tcgccccagc caccaccacc | 6060 |
| gagctccagt actacggtgg ccgactcctc accctcggag gccccgtcct catgggctcc | 6120 |
| gtcacccgca tcccagccga cctcacccgc ctcaaccccg tcatcaagac cgccgtgggc | 6180 |
| ttcactgact gcccccgctt cacctactcc gtctatgcca acggcgggtc cgccaacact | 6240 |
| cctctcatca ccgtcatggt gcgaggagtt atccgcctct ccggcccttc gggcaacacc | 6300 |
| gtcaccgcca cctaagccct ctcaccggtt tcaacaggag tttcttcctc gttcttctcc | 6360 |
| tgacgaccaa tgaacgttgc ttatccccc ttcacatccc tccgtttccc cctccgtttt | 6420 |
| cctctctgtt ccattccccc tctccctccc cgtctcagca atgagtaagg ttccaggtcg | 6480 |
| attcaaagac ctgatgggat tttcctcgg | 6509 |

<210> SEQ ID NO 14
<211> LENGTH: 2066
<212> TYPE: PRT
<213> ORGANISM: Oat Blue Dwarf Virus

<400> SEQUENCE: 14

Met Thr Thr Tyr Ala Phe His Pro Leu Leu Pro Thr Pro Thr Ser Phe
1               5                   10                  15

```
Ala Thr Ile Thr Gly Gly Gly Leu Lys Asp Val Ile Glu Thr Leu Ser
            20                  25                  30

Ser Thr Ile His Arg Asp Thr Ile Ala Ala Pro Leu Met Glu Thr Leu
            35                  40                  45

Ala Ser Pro Tyr Arg Asp Ser Leu Arg Asp Phe Pro Trp Ala Val Pro
        50                  55                  60

Ala Ser Ala Leu Pro Phe Leu Gln Glu Cys Gly Ile Thr Val Ala Gly
65                  70                  75                  80

His Gly Phe Lys Ala His Pro His Pro Val His Lys Thr Ile Glu Thr
                85                  90                  95

His Leu Leu His Lys Val Trp Pro His Tyr Ala Gln Val Pro Ser Ser
            100                 105                 110

Val Leu Phe Met Lys Pro Ser Lys Phe Ala Lys Leu Gln Arg Gly Asn
            115                 120                 125

Ala Asn Phe Ser Ala Leu His Asn Tyr Arg Leu Thr Ala Lys Asp Thr
130                 135                 140

Pro Arg Tyr Pro Asn Thr Ser Ser Leu Pro Asp Thr Glu Thr Ala
145                 150                 155                 160

Phe Met His Asp Ala Leu Met Tyr Tyr Thr Pro Ala Gln Ile Val Asp
                165                 170                 175

Leu Phe Leu Ser Cys Pro Lys Leu Glu Lys Leu Tyr Ala Ser Leu Val
            180                 185                 190

Val Pro Pro Glu Ser Ser Phe Thr Ser Ile Ser Leu His Pro Asp Leu
            195                 200                 205

Tyr Arg Phe Arg Phe Asp Gly Asp Arg Leu Ile Tyr Glu Leu Glu Gly
            210                 215                 220

Asn Pro Ala His Asn Tyr Thr Gln Pro Arg Ser Ala Leu Asp Trp Leu
225                 230                 235                 240

Arg Thr Thr Thr Ile Arg Gly Pro Gly Val Ser Leu Thr Val Ser Arg
                245                 250                 255

Leu Asp Ser Trp Gly Pro Cys His Ser Leu Leu Ile Gln Arg Gly Ile
            260                 265                 270

Pro Pro Met His Ala Glu His Asp Ser Ile Ser Phe Arg Gly Pro Arg
            275                 280                 285

Ala Val Ala Ile Pro Glu Pro Ser Ser Leu His Gln Asp Leu Arg His
            290                 295                 300

Arg Leu Val Pro Glu Asp Val Tyr Asn Ala Leu Phe Leu Tyr Val Arg
305                 310                 315                 320

Ala Val Arg Thr Leu Arg Val Thr Asp Pro Ala Gly Phe Val Arg Thr
                325                 330                 335

Gln Cys Ser Lys Pro Glu Tyr Ala Trp Val Thr Ser Ser Ala Trp Asp
            340                 345                 350

Asn Leu Ala His Phe Ala Leu Leu Thr Ala Pro His Arg Pro Arg Thr
            355                 360                 365

Ser Phe Tyr Leu Phe Ser Ser Thr Phe Gln Arg Leu Glu His Trp Val
            370                 375                 380

Arg His His Thr Phe Leu Leu Ala Gly Leu Thr Thr Ala Phe Ala Leu
385                 390                 395                 400

Pro Pro Ser Ala Trp Leu Ala Asn Leu Val Ala Arg Ala Ser Ala Ser
                405                 410                 415

His Ile Gln Gly Leu Ala Leu Ala Arg Arg Trp Leu Ile Thr Pro Pro
            420                 425                 430

His Leu Phe Arg Pro Pro Pro Pro Ser Phe Ala Leu Leu Leu Gln
```

-continued

```
            435                 440                 445
Arg Asn Ser Thr Gly Pro Val Leu Leu Arg Gly Ser Arg Leu Glu Phe
    450                 455                 460

Glu Ala Phe Pro Ser Leu Ala Pro Gln Leu Ala Arg Arg Phe Pro Phe
465                 470                 475                 480

Leu Ala Arg Leu Leu Pro Gln Lys Pro Ile Asp Pro Trp Val Val Ala
                485                 490                 495

Ser Leu Ala Val Ala Val Ala Ile Pro Ala Ala Ser Leu Ala Val Arg
                500                 505                 510

Trp Phe Phe Gly Pro Asp Thr Pro Gln Ala Met His Asp Arg Tyr His
            515                 520                 525

Thr Met Phe His Pro Arg Glu Trp Arg Leu Thr Leu Pro Arg Gly Pro
        530                 535                 540

Ile Ser Cys Gly Arg Ser Ser Phe Ser Pro Leu Pro His Pro Pro Ser
545                 550                 555                 560

Pro Thr Pro Ala Pro Asp Ser Arg Ala Glu Pro Leu Gln Pro Pro Ser
                565                 570                 575

Ala Pro Pro Ser Thr His Glu Pro Ala Pro Ala Asp Leu Glu Pro Gln
            580                 585                 590

Ala Pro Pro Ala His Ala Pro Gln Thr Glu Pro Pro Ser Pro Val Ile
        595                 600                 605

Glu Gln Glu Ala Arg Pro Asn Pro Leu Pro Ala Pro Ala Pro Leu Ser
610                 615                 620

Ala Pro Thr Pro Ser Ala Ser Ala Pro Ser Leu Ala Pro Thr Pro Ser
625                 630                 635                 640

Ala Pro Glu Pro Pro Ser Pro Thr Ala Ser Glu Gln Ala Ala Ser Leu
                645                 650                 655

Ile Pro Ala Pro Ser Ser Ala Leu Val Val Glu Pro Ser Gly Val Val
            660                 665                 670

Ser Ala Ser Ser Trp Gly Ala Thr Asn Gln Pro Ala Asp Gln Val Asp
        675                 680                 685

Asp Ser Pro Leu Ala Arg Asp Pro Ser Ala Ser Gly Pro Val Arg Phe
    690                 695                 700

Tyr Arg Asp Leu Phe Pro Ala Asn Tyr Ala Gly Asp Ser Gly Thr Phe
705                 710                 715                 720

Asp Phe Arg Ala Arg Ala Ser Gly Arg Ser Pro Thr Pro Tyr Pro Ala
                725                 730                 735

Met Asp Cys Leu Leu Val Ala Thr Glu Gln Ala Thr Arg Ile Ser Arg
            740                 745                 750

Glu Ala Leu Trp Asp Cys Leu Thr Ala Thr Cys Pro Asp Ser Phe Leu
        755                 760                 765

Asp Pro Lys Ser Ile Ala Gln His Gly Leu Ser Thr Asp His Phe Val
    770                 775                 780

Ile Leu Ala His Arg Phe Ser Leu Cys Ala Asn Phe His Ser Ala Glu
785                 790                 795                 800

His Val Ile Gln Leu Gly Met Ala Asp Ala Thr Ser Ile Phe Met Ile
                805                 810                 815

Asn His Thr Ala Gly Ser Ala Gly Leu Pro Gly His Pro Ser Leu Arg
            820                 825                 830

Leu Gly Asp Gln Pro Arg Ala Leu Asn Gly Gly Leu Ala Gln Asp Leu
        835                 840                 845

Ala Val Ala Ala Leu Arg Phe Asn Ile Ser Gly Asp Leu Leu Pro Thr
    850                 855                 860
```

-continued

```
Arg Ser Val His Thr Tyr Arg Ser Trp Pro Lys Arg Ala Lys Asn Leu
865                 870                 875                 880

Val Ser Asn Met Lys Asn Gly Phe Asp Gly Val Met Ala Ser Ile Asn
                885                 890                 895

Pro Ile Arg Pro Ser Asp Ala Arg Glu Lys Ile Val Ala Leu Asp Gly
            900                 905                 910

Leu Leu Asp Ile Ala Arg Pro Arg Ser Val Arg Leu Ile His Ile Ala
        915                 920                 925

Gly Phe Pro Gly Cys Gly Lys Thr His Pro Ile Thr Lys Leu Leu His
    930                 935                 940

Thr Ala Ala Phe Arg Asp Phe Lys Leu Ala Val Pro Thr Thr Glu Leu
945                 950                 955                 960

Arg Ser Glu Trp Lys Glu Leu Met Lys Leu Ser Pro Ser Gln Ala Trp
                965                 970                 975

Arg Phe Gly Thr Trp Glu Ser Ser Leu Leu Lys Ser Ala Arg Ile Leu
            980                 985                 990

Val Ile Asp Glu Ile Tyr Lys Leu Pro Arg Gly Tyr Leu Asp Leu Ala
        995                 1000                1005

Ile His Ser Asp Ser Ser Ile Glu Phe Val Ile Ala Leu Gly Asp
    1010                1015                1020

Pro Leu Gln Gly Glu Tyr His Ser Thr His Pro Ser Ser Ser Asn
    1025                1030                1035

Ser Arg Leu Ile Pro Glu Val Ser His Leu Ala Pro Tyr Leu Asp
    1040                1045                1050

Tyr Tyr Cys Leu Trp Ser Tyr Arg Val Pro Gln Asp Val Ala Ala
    1055                1060                1065

Phe Phe Gln Val Gln Ser His Asn Pro Ala Leu Gly Phe Ala Arg
    1070                1075                1080

Leu Ser Lys Gln Phe Pro Thr Thr Gly Arg Val Leu Thr Asn Ser
    1085                1090                1095

Gln Asn Ser Met Leu Thr Met Thr Gln Cys Gly Tyr Ser Ala Val
    1100                1105                1110

Thr Ile Ala Ser Ser Gln Gly Ser Thr Tyr Ser Gly Ala Thr His
    1115                1120                1125

Ile His Leu Asp Arg Asn Ser Ser Leu Leu Ser Pro Ser Asn Ser
    1130                1135                1140

Leu Val Ala Leu Thr Arg Ser Arg Thr Gly Val Phe Phe Ser Gly
    1145                1150                1155

Asp Pro Ala Leu Leu Asn Gly Gly Pro Asn Ser Asn Leu Met Phe
    1160                1165                1170

Ser Ala Phe Phe Gln Gly Lys Ser Arg His Ile Arg Ala Trp Phe
    1175                1180                1185

Pro Thr Leu Phe Pro Thr Ala Thr Leu Leu Phe Ser Pro Leu Arg
    1190                1195                1200

Gln Arg His Asn Arg Leu Thr Gly Ala Leu Ala Pro Ala Gln Pro
    1205                1210                1215

Ser His Leu Leu Leu Pro Asp Leu Pro Ser Leu Pro Pro Leu Pro
    1220                1225                1230

Ala Ser Gly Pro Tyr Ser Arg Ser Phe Pro Val Arg Ser Arg Phe
    1235                1240                1245

Ala Ala Ala Val Lys Pro Ser Asp Arg Ser Asp Val Leu Ser Trp
    1250                1255                1260
```

```
Ala Pro Ile Ala Val Gly Asp Gly Glu Thr Asn Ala Pro Arg Ile
1265                1270                1275

Asp Thr Ser Phe Leu Pro Glu Thr Arg Arg Pro Leu His Phe Asp
1280                1285                1290

Leu Pro Ser Phe Arg Pro Gln Ala Pro Pro Pro Ser Asp Pro
1295                1300                1305

Ala Pro Ser Gly Thr Ala Phe Glu Pro Val Tyr Pro Gly Glu Thr
1310                1315                1320

Phe Glu Asn Leu Val Ala His Phe Leu Pro Ala His Asp Pro Thr
1325                1330                1335

Asp Arg Glu Ile His Trp Arg Arg Gln Leu Ser Asn Gln Phe Pro
1340                1345                1350

His Val Asp Lys Glu Tyr His Leu Ala Ala Gln Pro Met Thr Leu
1355                1360                1365

Leu Ala Pro Ile His Asp Ser Lys His Asp Pro Thr Leu Leu Ala
1370                1375                1380

Ala Ser Ile Gln Lys Arg Leu Arg Phe Arg Pro Ser Ala Ser Pro
1385                1390                1395

Tyr Arg Ile Ser Pro Arg Asp Glu Leu Leu Gly Gln Leu Leu Tyr
1400                1405                1410

Glu Ser Leu Cys Arg Ala Tyr His Arg Ser Pro Thr Thr Thr His
1415                1420                1425

Pro Phe Asp Glu Ala Leu Phe Val Glu Cys Ile Asp Leu Asn Glu
1430                1435                1440

Phe Ala Gln Leu Thr Ser Lys Thr Gln Ala Val Ile Met Gly Asn
1445                1450                1455

Ala Arg Arg Ser Asp Pro Asp Trp Arg Trp Ser Ala Val Arg Ile
1460                1465                1470

Phe Ser Lys Thr Gln His Lys Val Asn Glu Gly Ser Ile Phe Gly
1475                1480                1485

Ala Trp Lys Ala Cys Gln Thr Leu Ala Leu Met His Asp Ala Val
1490                1495                1500

Val Leu Leu Leu Gly Pro Val Lys Lys Tyr Gln Arg Val Phe Asp
1505                1510                1515

Ala Arg Asp Arg Pro Ala His Leu Tyr Ile His Ala Gly Gln Thr
1520                1525                1530

Pro Ser Ser Met Ser Leu Trp Cys Gln Thr His Leu Thr Pro Ala
1535                1540                1545

Val Lys Leu Ala Asn Asp Tyr Thr Ala Phe Asp Gln Ser Gln His
1550                1555                1560

Gly Glu Ala Val Val Leu Glu Arg Lys Lys Met Glu Arg Leu Ser
1565                1570                1575

Ile Pro Asp His Leu Ile Ser Leu His Val His Leu Lys Thr His
1580                1585                1590

Val Glu Thr Gln Phe Gly Pro Leu Thr Cys Met Arg Leu Thr Gly
1595                1600                1605

Glu Pro Gly Thr Tyr Asp Asp Asn Thr Asp Tyr Asn Leu Ala Val
1610                1615                1620

Ile Asn Leu Glu Tyr Ala Ala Ala His Val Pro Thr Met Val Ser
1625                1630                1635

Gly Asp Asp Ser Leu Leu Asp Phe Glu Pro Pro Arg Arg Pro Glu
1640                1645                1650

Trp Val Ala Ile Glu Pro Leu Leu Ala Leu Arg Phe Lys Lys Glu
```

-continued

```
            1655                1660                1665
Arg Gly Leu Tyr Ala Thr Phe Cys Gly Tyr Tyr Ala Ser Arg Val
    1670                1675                1680
Gly Cys Val Arg Ser Pro Ile Ala Leu Phe Ala Lys Leu Ala Ile
    1685                1690                1695
Ala Val Asp Asp Ser Ser Ile Ser Asp Lys Leu Ala Ala Tyr Leu
    1700                1705                1710
Met Glu Phe Ala Val Gly His Ser Leu Gly Asp Ser Leu Trp Ser
    1715                1720                1725
Ala Leu Pro Leu Ser Ala Val Pro Phe Gln Ser Ala Cys Phe Asp
    1730                1735                1740
Phe Phe Cys Arg Arg Ala Pro Arg Asp Leu Lys Leu Ala Leu His
    1745                1750                1755
Leu Gly Glu Val Pro Glu Thr Ile Ile Gln Arg Leu Ser His Leu
    1760                1765                1770
Ser Trp Leu Ser His Ala Val Tyr Ser Leu Leu Pro Ser Arg Leu
    1775                1780                1785
Arg Leu Ala Ile Leu His Ser Ser Arg Gln His Arg Ser Leu Pro
    1790                1795                1800
Glu Asp Pro Ala Val Ser Ser Leu Gln Gly Glu Leu Leu Gln Thr
    1805                1810                1815
Phe His Ala Pro Met Pro Ser Leu Pro Ser Leu Pro Leu Phe Gly
    1820                1825                1830
Gly Leu Ser Pro Asp Asn Ile Leu Thr Pro His Glu Phe Arg Thr
    1835                1840                1845
Ala Leu Tyr Glu Ser Ser Ala Tyr Pro Thr Pro Pro Asn Ser Pro
    1850                1855                1860
Thr Ser Met Ser Gly Ile His Ala Ser Gln Val Gly Pro Pro Pro
    1865                1870                1875
Ala Ser Asp Asp Arg Thr Asp Arg Gln Pro Ser Leu Pro Leu Ala
    1880                1885                1890
Pro Arg Ile Val Glu Ser Ser Leu Ala Val Pro His Val Asp Val
    1895                1900                1905
Pro Phe Gln Trp Ala Val Ala Ser Tyr Ala Gly Asp Ser Ala Lys
    1910                1915                1920
Phe Leu Thr Asp Asp Leu Ser Gly Ser Ser His Leu Ser Arg Leu
    1925                1930                1935
Thr Ile Gly Tyr Arg His Ala Glu Leu Ile Ser Ala Glu Leu Glu
    1940                1945                1950
Phe Ala Pro Leu Ala Ala Ala Phe Ala Lys Pro Ile Ser Val Thr
    1955                1960                1965
Ala Val Trp Thr Ile Ala Ser Ile Ala Pro Ala Thr Thr Thr Glu
    1970                1975                1980
Leu Gln Tyr Tyr Gly Gly Arg Leu Leu Thr Leu Gly Gly Pro Val
    1985                1990                1995
Leu Met Gly Ser Val Thr Arg Ile Pro Ala Asp Leu Thr Arg Leu
    2000                2005                2010
Asn Pro Val Ile Lys Thr Ala Val Gly Phe Thr Asp Cys Pro Arg
    2015                2020                2025
Phe Thr Tyr Ser Val Tyr Ala Asn Gly Gly Ser Ala Asn Thr Pro
    2030                2035                2040
Leu Ile Thr Val Met Val Arg Gly Val Ile Arg Leu Ser Gly Pro
    2045                2050                2055
```

```
Ser Gly Asn Thr Val Thr Ala Thr
    2060                2065
```

```
<210> SEQ ID NO 15
<211> LENGTH: 216
<212> TYPE: PRT
<213> ORGANISM: Grapevine Asteroid Mosaic-Associated Virus

<400> SEQUENCE: 15
```

```
Ser Ser Ala Pro Gln Leu Thr Ser Glu Ala Phe Ser Leu Thr Leu Ala
1               5                   10                  15

Gln Ser Met Ala Ser Pro Asn Val Gln Ala Gly Pro Pro Pro Pro Ser
            20                  25                  30

Asp Asp Arg Thr Asp Arg Gln Pro Pro Leu Pro Arg Ala Pro Arg Leu
        35                  40                  45

Val Glu Asp Ala Ser Ala Ile Pro Phe Val Asp Tyr Pro Phe Gln Trp
    50                  55                  60

Val Val Ala Ser Tyr Asp Gly Ser Thr Ala Lys Asn Leu Thr Asp Val
65                  70                  75                  80

Leu Ser Gly Ser Lys Thr Leu Ser Thr Ile Thr Ala Asn Tyr Arg His
                85                  90                  95

Ala Glu Leu Leu Ser Val Glu Leu Glu Phe Ala Pro Leu Ala Gly Ser
            100                 105                 110

Phe Ser Lys Pro Ile Thr Leu Ser Ala Val Trp Thr Val Gly Ser Ile
        115                 120                 125

Thr Pro Ala Thr Thr Thr Glu Thr Ser Tyr Tyr Gly Gly Arg Val Ile
    130                 135                 140

Thr Ile Gly Gly Pro Val Leu Met Asn Ser Thr Thr Ala Val Pro Ala
145                 150                 155                 160

Asp Leu Arg Arg Leu Asn Pro Ile Ile Lys Asp Gln Ile Ser Tyr Thr
                165                 170                 175

Asp Cys Pro Arg Phe Ser Tyr Ser Val Tyr Ala Asn Gly Gly Thr Ala
            180                 185                 190

Gly Thr Asn Leu Val Thr Val Leu Ile Arg Gly Val Val Arg Leu Arg
        195                 200                 205

Ser Pro Ser Gly Asn Leu Leu Ala
    210                 215
```

```
<210> SEQ ID NO 16
<211> LENGTH: 215
<212> TYPE: PRT
<213> ORGANISM: Citrus Sudden Death Virus

<400> SEQUENCE: 16
```

```
Ser Ser Ala Pro Ile Leu Thr Pro Glu Ala Phe Ser Thr Ser Leu Ala
1               5                   10                  15

Phe Ser Met Ala Ser Asp Ala Gln Ala Gly Pro Ala Pro Ser Arg Asp
            20                  25                  30

Asp Arg Val Asp Arg Gln Pro Arg Leu Pro Ala Ala Pro Arg Val Ala
        35                  40                  45

Glu Val Gly Leu Asn Ala Pro Ser Val Asp Tyr Pro Phe Gln Trp Val
    50                  55                  60

Val Ala Ser Tyr Asp Gly Ser Glu Ala Lys Asn Leu Ser Asp Asp Leu
65                  70                  75                  80

Ser Gly Ser Ala Thr Leu Thr Lys Val Met Ala Asn Tyr Arg His Ala
                85                  90                  95
```

```
Glu Leu Thr Ser Val Glu Leu Glu Val Cys Pro Leu Ala Ala Ala Phe
            100                 105                 110

Ser Lys Pro Ile Ser Val Ser Ala Val Trp Thr Ile Ala Ser Ile Ser
        115                 120                 125

Pro Ala Ser Ala Ser Glu Thr Ser Tyr Tyr Gly Gly Arg Leu Phe Thr
    130                 135                 140

Val Gly Gly Pro Val Leu Met Ser Ser Thr His Leu Pro Ala Asp
145                 150                 155                 160

Leu Thr Arg Leu Asn Pro Val Leu Lys Gly Pro Val Lys Tyr Thr Asp
                165                 170                 175

Cys Pro Arg Phe Ser Tyr Ser Val Tyr Ser Asn Gly Thr Lys Gly
            180                 185                 190

Thr Asn Leu Cys Thr Ile Ile Leu Arg Gly Val Val Arg Leu Ser Gly
            195                 200                 205

Pro Ser Gly Asn Leu Leu Ala
    210                 215

<210> SEQ ID NO 17
<211> LENGTH: 198
<212> TYPE: PRT
<213> ORGANISM: Grapevine Asteroid Mosaic-Associated Virus

<400> SEQUENCE: 17

Met Ala Ser Pro Asn Val Gln Ala Gly Pro Pro Pro Ser Asp Asp
1               5                   10                  15

Arg Thr Asp Arg Gln Pro Pro Leu Pro Arg Ala Pro Arg Leu Val Glu
            20                  25                  30

Asp Ala Ser Ala Ile Pro Phe Val Asp Tyr Pro Phe Gln Trp Val Val
        35                  40                  45

Ala Ser Tyr Asp Gly Ser Thr Ala Lys Asn Leu Thr Asp Val Leu Ser
    50                  55                  60

Gly Ser Lys Thr Leu Ser Thr Ile Thr Ala Asn Tyr Arg His Ala Glu
65                  70                  75                  80

Leu Leu Ser Val Glu Leu Glu Phe Ala Pro Leu Ala Gly Ser Phe Ser
                85                  90                  95

Lys Pro Ile Thr Leu Ser Ala Val Trp Thr Val Gly Ser Ile Thr Pro
            100                 105                 110

Ala Thr Thr Thr Glu Thr Ser Tyr Tyr Gly Gly Arg Val Ile Thr Ile
        115                 120                 125

Gly Gly Pro Val Leu Met Asn Ser Thr Ala Val Pro Ala Asp Leu
    130                 135                 140

Arg Arg Leu Asn Pro Ile Ile Lys Asp Gln Ile Ser Tyr Thr Asp Cys
145                 150                 155                 160

Pro Arg Phe Ser Tyr Ser Val Tyr Ala Asn Gly Gly Thr Ala Gly Thr
                165                 170                 175

Asn Leu Val Thr Val Leu Ile Arg Gly Val Val Arg Leu Arg Ser Pro
            180                 185                 190

Ser Gly Asn Leu Leu Ala
        195

<210> SEQ ID NO 18
<211> LENGTH: 197
<212> TYPE: PRT
<213> ORGANISM: Citrus Sudden Death Virus

<400> SEQUENCE: 18
```

```
Met Ala Ser Asp Ala Gln Ala Gly Pro Ala Pro Ser Arg Asp Asp Arg
1               5                   10                  15

Val Asp Arg Gln Pro Arg Leu Pro Ala Ala Pro Arg Val Ala Glu Val
            20                  25                  30

Gly Leu Asn Ala Pro Ser Val Asp Tyr Pro Phe Gln Trp Val Val Ala
            35                  40                  45

Ser Tyr Asp Gly Ser Glu Ala Lys Asn Leu Ser Asp Asp Leu Ser Gly
        50                  55                  60

Ser Ala Thr Leu Thr Lys Val Met Ala Asn Tyr Arg His Ala Glu Leu
65                  70                  75                  80

Thr Ser Val Glu Leu Glu Val Cys Pro Leu Ala Ala Phe Ser Lys
                85                  90                  95

Pro Ile Ser Val Ser Ala Val Trp Thr Ile Ala Ser Ile Ser Pro Ala
                100                 105                 110

Ser Ala Ser Glu Thr Ser Tyr Tyr Gly Gly Arg Leu Phe Thr Val Gly
                115                 120                 125

Gly Pro Val Leu Met Ser Ser Thr His Leu Pro Ala Asp Leu Thr
130                 135                 140

Arg Leu Asn Pro Val Leu Lys Gly Pro Val Lys Tyr Thr Asp Cys Pro
145                 150                 155                 160

Arg Phe Ser Tyr Ser Val Tyr Ser Asn Gly Gly Thr Lys Gly Thr Asn
                165                 170                 175

Leu Cys Thr Ile Ile Leu Arg Gly Val Val Arg Leu Ser Gly Pro Ser
                180                 185                 190

Gly Asn Leu Leu Ala
            195

<210> SEQ ID NO 19
<211> LENGTH: 309
<212> TYPE: PRT
<213> ORGANISM: Grapevine Fleck Virus

<400> SEQUENCE: 19

Met Thr Ser Arg Ala Pro Ser Pro Pro Thr Pro Pro Cys Pro Ser Pro
1               5                   10                  15

Pro Ala Leu Lys Ser Ser Pro Ser Pro Val Pro Thr Ala Thr Pro Ala
            20                  25                  30

Ser Pro Pro Leu Lys Pro Leu Ser Asn Pro Leu Pro Pro Pro Pro Pro
        35                  40                  45

Thr Pro Arg Pro Ser Thr Ser Ala Gly Pro Ser Thr Pro Leu Pro Pro
    50                  55                  60

Pro Ala Leu Arg Ser Ser Pro Ser Ser Ala Leu Asn Ala Ser Arg Gly
65                  70                  75                  80

Ala Pro Ser Thr Ser Pro Pro Ser Ser Pro Ser Ser Pro
                85                  90                  95

Ala Ser Thr Pro Pro Ser Arg Thr Pro Ser Pro Thr Thr Ala Pro
                100                 105                 110

Ala Ser Pro Val Ala Ser Thr Ala Met Thr Pro Ala Ser Pro Ser Val
                115                 120                 125

Pro Pro Pro Pro Ser Ala Ala Pro Ser Ser Ala Ala Leu Ser Ser
                130                 135                 140

Ala Pro Pro Pro Ser Thr Ala Pro Leu Pro Arg His Glu Pro Arg Pro
145                 150                 155                 160

Pro Pro Pro Leu Pro Pro Pro Leu Gln Pro Pro Pro Gly Val Arg Val
```

```
                    165                 170                 175
Pro Arg Ser Val Ala Phe Pro Leu Pro Leu Ala Arg Glu Leu Pro Pro
            180                 185                 190

Leu Arg Leu Pro Pro Ala Pro Tyr Leu His Pro Leu Leu Ala Arg Leu
        195                 200                 205

Ala Pro Leu Arg Leu Arg Pro Pro Asp Leu Pro Ser Pro Pro Leu
    210                 215                 220

Ser Pro Pro Leu Ser Pro Pro Leu Ser Pro Ile Ser Pro Leu His Ala
225                 230                 235                 240

Pro Ala Pro Pro Pro His Pro Asp Pro Val Leu Leu Pro Ala Leu Ser
                245                 250                 255

Leu Ala Ile Ser Arg Ala Ala Pro Asp Leu Leu Arg Leu Leu Ser Leu
            260                 265                 270

Leu Ser Pro Pro Ser Leu Phe Leu Leu Phe Thr Leu Leu Ser Ile His
        275                 280                 285

Phe Ser Pro Phe Pro Ile Phe Ile Leu Leu Ser Leu Leu Leu Leu Leu
    290                 295                 300

Gln Phe Pro Arg Thr
305
```